US012752053B2

(12) United States Patent
O'Connor et al.

(10) Patent No.: US 12,752,053 B2
(45) Date of Patent: Oct. 6, 2026

(54) MEDICATION DELIVERY SYSTEM WITH GRAPHICAL USER INTERFACE

(71) Applicant: Insulet Corporation, Acton, MA (US)

(72) Inventors: Jason O'Connor, Acton, MA (US); Joon Bok Lee, Acton, MA (US); David Nazzaro, Groveland, MA (US); Yibin Zheng, Hartland, WI (US); Pauline Tandon, Hopkinton, MA (US)

(73) Assignee: INSULET CORPORATION, Acton, MA (US)

( * ) Notice: Subject to any disclaimer, the term of this patent is extended or adjusted under 35 U.S.C. 154(b) by 58 days.

(21) Appl. No.: 17/514,336

(22) Filed: Oct. 29, 2021

(65) Prior Publication Data

US 2022/0203023 A1 Jun. 30, 2022

Related U.S. Application Data

(60) Provisional application No. 63/132,694, filed on Dec. 31, 2020.

(51) Int. Cl.

| | |
|---|---|
| ***G06F 3/048*** | (2013.01) |
| ***A61M 5/142*** | (2006.01) |
| ***A61M 5/168*** | (2006.01) |

(52) U.S. Cl.

CPC ........ *A61M 5/168* (2013.01); *A61M 5/14244* (2013.01); *G06F 3/048* (2013.01); *A61M 2205/3553* (2013.01); *A61M 2205/502* (2013.01); *A61M 2205/583* (2013.01); *A61M 2230/201* (2013.01)

(58) Field of Classification Search

CPC .... A61M 5/168; A61M 5/14244; G06F 3/048

See application file for complete search history.

(56) References Cited

U.S. PATENT DOCUMENTS

| | | | |
|---|---|---|---|
| 445,545 | A | 2/1891 | Crane |
| 588,583 | A | 8/1897 | Lade |

(Continued)

FOREIGN PATENT DOCUMENTS

| | | | |
|---|---|---|---|
| CN | 101208699 | A | 6/2008 |
| DE | 4200595 | A1 | 7/1993 |

(Continued)

OTHER PUBLICATIONS

Andrenko et al., "EM Analysis of PBG Substrate Microstrip Circuits for Integrated Transmitter Front End" MMET Proceedings, 295-297 (2000).

(Continued)

*Primary Examiner* — William L Bashore
*Assistant Examiner* — Gregory A Distefano
(74) *Attorney, Agent, or Firm* — Goodwin Procter LLP

(57) ABSTRACT

A system for automatically delivering medication to a user is disclosed. A sensor worn by the user can collect information regarding the user. A user device, for example, a smartphone, executes a user application that uses the collected information to determine an amount of medication to provide to the user. The user application includes a graphical user interface that allows the user to easily interact with the user application to specify various aspects of the delivery of the medication. The user application controls a wearable drug delivery device to dispense the medication to the user.

23 Claims, 51 Drawing Sheets

400

(56) References Cited

U.S. PATENT DOCUMENTS

| | | | |
|---|---|---|---|
| 1,441,508 | A | 1/1923 | Marius |
| 2,283,925 | A | 5/1942 | Harvey |
| 2,886,529 | A | 5/1959 | Guillaud |
| 3,574,114 | A | 4/1971 | Monforte |
| 3,614,554 | A | 10/1971 | Shield |
| 3,885,662 | A | 5/1975 | Schaefer |
| 3,983,077 | A | 9/1976 | Fuller et al. |
| 4,108,177 | A | 8/1978 | Pistor |
| 4,268,150 | A | 5/1981 | Chen |
| 4,313,439 | A | 2/1982 | Babb et al. |
| 4,400,683 | A | 8/1983 | Eda et al. |
| 4,424,720 | A | 1/1984 | Bucchianeri |
| 4,435,173 | A | 3/1984 | Siposs et al. |
| 4,498,843 | A | 2/1985 | Schneider et al. |
| 4,507,115 | A | 3/1985 | Kambara et al. |
| 4,523,170 | A | 6/1985 | Huth, III |
| 4,551,134 | A | 11/1985 | Slavik et al. |
| 4,562,751 | A | 1/1986 | Nason et al. |
| 4,585,439 | A | 4/1986 | Michel |
| 4,601,707 | A | 7/1986 | Albisser et al. |
| 4,634,427 | A | 1/1987 | Hannula et al. |
| 4,646,038 | A | 2/1987 | Wanat |
| 4,678,408 | A | 7/1987 | Nason et al. |
| 4,684,368 | A | 8/1987 | Kenyon |
| 4,755,169 | A | 7/1988 | Sarnoff et al. |
| 4,759,120 | A | 7/1988 | Bernstein |
| 4,859,492 | A | 8/1989 | Rogers, Jr. et al. |
| 4,880,770 | A | 11/1989 | Mir et al. |
| 4,898,578 | A | 2/1990 | Rubalcaba, Jr. |
| 4,898,579 | A | 2/1990 | Groshong et al. |
| 4,944,659 | A | 7/1990 | Labbe et al. |
| 4,967,201 | A | 10/1990 | Rich, III |
| 4,969,874 | A | 11/1990 | Michel et al. |
| 5,007,458 | A | 4/1991 | Marcus et al. |
| 5,062,841 | A | 11/1991 | Siegel |
| 5,084,749 | A | 1/1992 | Losee et al. |
| 5,130,675 | A | 7/1992 | Sugawara |
| 5,139,999 | A | 8/1992 | Gordon et al. |
| 5,154,973 | A | 10/1992 | Imagawa et al. |
| 5,189,609 | A | 2/1993 | Tivig et al. |
| 5,198,824 | A | 3/1993 | Poradish |
| 5,205,819 | A | 4/1993 | Ross et al. |
| 5,213,483 | A | 5/1993 | Flaherty et al. |
| 5,217,754 | A | 6/1993 | Santiago-Aviles et al. |
| 5,219,377 | A | 6/1993 | Poradish |
| 5,254,096 | A | 10/1993 | Rondelet et al. |
| 5,261,882 | A | 11/1993 | Sealfon |
| 5,263,198 | A | 11/1993 | Geddes et al. |
| 5,272,485 | A | 12/1993 | Mason et al. |
| 5,281,202 | A | 1/1994 | Weber et al. |
| 5,346,476 | A | 9/1994 | Elson |
| 5,364,342 | A | 11/1994 | Beuchat et al. |
| 5,403,797 | A | 4/1995 | Ohtani et al. |
| 5,427,988 | A | 6/1995 | Sengupta et al. |
| 5,433,710 | A | 7/1995 | VanAntwerp et al. |
| 5,456,945 | A | 10/1995 | McMillan et al. |
| 5,478,610 | A | 12/1995 | Desu et al. |
| 5,513,382 | A | 4/1996 | Agahi-Kesheh et al. |
| 5,535,445 | A | 7/1996 | Gunton |
| 5,540,772 | A | 7/1996 | McMillan et al. |
| 5,543,773 | A | 8/1996 | Evans et al. |
| 5,582,593 | A | 12/1996 | Hultman |
| 5,584,053 | A | 12/1996 | Kommrusch et al. |
| 5,590,387 | A | 12/1996 | Schmidt et al. |
| 5,614,252 | A | 3/1997 | McMillan et al. |
| 5,625,365 | A | 4/1997 | Tom et al. |
| 5,635,433 | A | 6/1997 | Sengupta |
| 5,637,095 | A | 6/1997 | Nason et al. |
| 5,665,070 | A | 9/1997 | McPhee |
| 5,707,459 | A | 1/1998 | Itoyama et al. |
| 5,707,715 | A | 1/1998 | deRochemont et al. |
| 5,713,875 | A | 2/1998 | Tanner, II |
| 5,747,350 | A | 5/1998 | Sattler |
| 5,747,870 | A | 5/1998 | Pedder |
| 5,748,827 | A | 5/1998 | Holl et al. |
| 5,759,923 | A | 6/1998 | McMillan et al. |
| 5,764,189 | A | 6/1998 | Lohninger |
| 5,771,567 | A | 6/1998 | Pierce et al. |
| 5,776,103 | A | 7/1998 | Kriesel et al. |
| 5,779,676 | A | 7/1998 | Kriesel et al. |
| 5,785,688 | A | 7/1998 | Joshi et al. |
| 5,797,881 | A | 8/1998 | Gadot |
| 5,800,397 | A | 9/1998 | Wilson et al. |
| 5,807,075 | A | 9/1998 | Jacobsen et al. |
| 5,839,467 | A | 11/1998 | Saaski et al. |
| 5,854,608 | A | 12/1998 | Leisten |
| 5,858,239 | A | 1/1999 | Kenley et al. |
| 5,859,621 | A | 1/1999 | Leisten |
| 5,889,459 | A | 3/1999 | Hattori et al. |
| 5,891,097 | A | 4/1999 | Saito et al. |
| 5,892,489 | A | 4/1999 | Kanba et al. |
| 5,897,530 | A | 4/1999 | Jackson |
| 5,903,421 | A | 5/1999 | Furutani et al. |
| 5,906,597 | A | 5/1999 | McPhee |
| 5,911,716 | A | 6/1999 | Rake et al. |
| 5,919,167 | A | 7/1999 | Mulhauser et al. |
| 5,933,121 | A | 8/1999 | Rainhart et al. |
| 5,945,963 | A | 8/1999 | Leisten |
| 5,957,890 | A | 9/1999 | Mann et al. |
| 5,961,492 | A | 10/1999 | Kriesel et al. |
| 5,965,848 | A | 10/1999 | Altschul et al. |
| 6,019,747 | A | 2/2000 | McPhee |
| 6,023,251 | A | 2/2000 | Koo et al. |
| 6,027,826 | A | 2/2000 | deRochemont et al. |
| 6,028,568 | A | 2/2000 | Asakura et al. |
| 6,031,445 | A | 2/2000 | Marty et al. |
| 6,040,805 | A | 3/2000 | Huynh et al. |
| 6,046,707 | A | 4/2000 | Gaughan et al. |
| 6,052,040 | A | 4/2000 | Hino |
| 6,111,544 | A | 8/2000 | Dakeya et al. |
| 6,143,432 | A | 11/2000 | de Rochemont et al. |
| 6,154,176 | A | 11/2000 | Fathy et al. |
| 6,174,300 | B1 | 1/2001 | Kriesel et al. |
| 6,176,004 | B1 | 1/2001 | Rainhart et al. |
| 6,181,297 | B1 | 1/2001 | Leisten |
| 6,188,368 | B1 | 2/2001 | Koriyama et al. |
| 6,190,359 | B1 | 2/2001 | Heruth |
| 6,195,049 | B1 | 2/2001 | Kim et al. |
| 6,200,293 | B1 | 3/2001 | Kriesel et al. |
| 6,204,203 | B1 | 3/2001 | Narwankar et al. |
| 6,208,843 | B1 | 3/2001 | Huang et al. |
| 6,222,489 | B1 | 4/2001 | Tsuru et al. |
| 6,266,020 | B1 | 7/2001 | Chang |
| 6,300,894 | B1 | 10/2001 | Lynch et al. |
| 6,320,547 | B1 | 11/2001 | Fathy et al. |
| 6,323,549 | B1 | 11/2001 | deRochemont et al. |
| 6,363,609 | B1 | 4/2002 | Pickren |
| 6,375,638 | B2 | 4/2002 | Nason et al. |
| 6,474,219 | B2 | 11/2002 | Klitmose et al. |
| 6,477,065 | B2 | 11/2002 | Parks |
| 6,485,461 | B1 | 11/2002 | Mason et al. |
| 6,485,462 | B1 | 11/2002 | Kriesel |
| 6,492,949 | B1 | 12/2002 | Breglia et al. |
| 6,496,149 | B1 | 12/2002 | Birnbaum et al. |
| 6,501,415 | B1 | 12/2002 | Viana et al. |
| 6,520,936 | B1 | 2/2003 | Mann |
| 6,527,744 | B1 | 3/2003 | Kriesel et al. |
| 6,537,249 | B2 | 3/2003 | Kriesell et al. |
| 6,540,260 | B1 | 4/2003 | Tan |
| 6,541,820 | B1 | 4/2003 | Bol |
| 6,552,693 | B1 | 4/2003 | Leisten |
| 6,559,735 | B1 | 5/2003 | Hoang et al. |
| 6,569,115 | B1 | 5/2003 | Barker et al. |
| 6,583,699 | B2 | 6/2003 | Yokoyama |
| 6,595,956 | B1 | 7/2003 | Gross et al. |
| 6,605,151 | B1 | 8/2003 | Wessels et al. |
| 6,611,419 | B1 | 8/2003 | Chakravorty |
| 6,620,750 | B2 | 9/2003 | Kim et al. |
| 6,635,958 | B2 | 10/2003 | Bates et al. |
| 6,639,556 | B2 | 10/2003 | Baba |
| 6,642,908 | B2 | 11/2003 | Pleva et al. |
| 6,650,303 | B2 | 11/2003 | Kim et al. |
| 6,656,158 | B2 | 12/2003 | Mahoney et al. |
| 6,670,497 | B2 | 12/2003 | Tashino et al. |

(56) References Cited

U.S. PATENT DOCUMENTS

| | | | | |
|---|---|---|---|---|
| 6,680,700 | B2 | 1/2004 | Hilgers | |
| 6,683,576 | B2 | 1/2004 | Achim | |
| 6,686,406 | B2 | 2/2004 | Tomomatsu et al. | |
| 6,690,336 | B1 | 2/2004 | Leisten et al. | |
| 6,697,605 | B1 | 2/2004 | Atokawa et al. | |
| 6,699,218 | B2 | 3/2004 | Flaherty et al. | |
| 6,720,926 | B2 | 4/2004 | Killen et al. | |
| 6,723,072 | B2 | 4/2004 | Flaherty et al. | |
| 6,727,785 | B2 | 4/2004 | Killen et al. | |
| 6,731,244 | B2 | 5/2004 | Killen et al. | |
| 6,731,248 | B2 | 5/2004 | Killen et al. | |
| 6,733,890 | B2 | 5/2004 | Imanaka et al. | |
| 6,740,059 | B2 | 5/2004 | Flaherty | |
| 6,741,148 | B2 | 5/2004 | Killen et al. | |
| 6,742,249 | B2 | 6/2004 | deRochemont et al. | |
| 6,743,744 | B1 | 6/2004 | Kim et al. | |
| 6,750,740 | B2 | 6/2004 | Killen et al. | |
| 6,750,820 | B2 | 6/2004 | Killen et al. | |
| 6,753,745 | B2 | 6/2004 | Killen et al. | |
| 6,753,814 | B2 | 6/2004 | Killen et al. | |
| 6,762,237 | B2 | 7/2004 | Glatkowski et al. | |
| 6,787,181 | B2 | 9/2004 | Uchiyama et al. | |
| 6,791,496 | B1 | 9/2004 | Killen et al. | |
| 6,826,031 | B2 | 11/2004 | Nagai et al. | |
| 6,830,623 | B2 | 12/2004 | Hayashi et al. | |
| 6,853,288 | B2 | 2/2005 | Ahn et al. | |
| 6,858,892 | B2 | 2/2005 | Yamagata | |
| 6,864,848 | B2 | 3/2005 | Sievenpiper | |
| 6,871,396 | B2 | 3/2005 | Sugaya et al. | |
| 6,878,871 | B2 | 4/2005 | Scher et al. | |
| 6,883,778 | B1 | 4/2005 | Newton et al. | |
| 6,905,989 | B2 | 6/2005 | Ellis et al. | |
| 6,906,674 | B2 | 6/2005 | McKinzie, III et al. | |
| 6,914,566 | B2 | 7/2005 | Beard | |
| 6,919,119 | B2 | 7/2005 | Kalkan et al. | |
| 6,928,298 | B2 | 8/2005 | Furutani et al. | |
| 6,943,430 | B2 | 9/2005 | Kwon | |
| 6,943,731 | B2 | 9/2005 | Killen et al. | |
| 6,963,259 | B2 | 11/2005 | Killen et al. | |
| 7,002,436 | B2 | 2/2006 | Ma et al. | |
| 7,047,637 | B2 | 5/2006 | deRochemont et al. | |
| 7,060,350 | B2 | 6/2006 | Takaya et al. | |
| 7,116,949 | B2 | 10/2006 | Irie et al. | |
| 7,137,694 | B2 | 11/2006 | Ferran et al. | |
| 7,144,384 | B2 | 12/2006 | Gorman et al. | |
| 7,160,272 | B1 | 1/2007 | Eyal et al. | |
| 7,230,316 | B2 | 6/2007 | Yamazaki et al. | |
| 7,291,782 | B2 | 11/2007 | Sager et al. | |
| 7,303,549 | B2 | 12/2007 | Flaherty et al. | |
| 7,405,698 | B2 | 7/2008 | de Rochemont | |
| 7,522,124 | B2 | 4/2009 | Smith et al. | |
| 7,553,512 | B2 | 6/2009 | Kodas et al. | |
| 7,564,887 | B2 | 7/2009 | Wang et al. | |
| 7,595,623 | B2 | 9/2009 | Bennett | |
| 7,652,901 | B2 | 1/2010 | Kirchmeier et al. | |
| 7,714,794 | B2 | 5/2010 | Tavassoli Hozouri | |
| 7,763,917 | B2 | 7/2010 | de Rochemont | |
| 7,771,391 | B2 | 8/2010 | Carter | |
| 7,812,774 | B2 | 10/2010 | Friman et al. | |
| 8,066,805 | B2 | 11/2011 | Zurcher et al. | |
| 8,069,690 | B2 | 12/2011 | DeSantolo et al. | |
| 8,114,489 | B2 | 2/2012 | Nemat-Nasser et al. | |
| 8,178,457 | B2 | 5/2012 | De Rochemont | |
| 8,193,873 | B2 | 6/2012 | Kato et al. | |
| 8,267,921 | B2 | 9/2012 | Yodfat et al. | |
| 8,350,657 | B2 | 1/2013 | deRochemont | |
| 8,354,294 | B2 | 1/2013 | de Rochemont et al. | |
| 8,593,819 | B2 | 11/2013 | de Rochemont | |
| 8,715,839 | B2 | 5/2014 | de Rochemont | |
| 8,939,935 | B2 | 1/2015 | OConnor et al. | |
| 9,180,244 | B2 | 11/2015 | Anderson et al. | |
| 9,192,716 | B2 | 11/2015 | Jugl et al. | |
| 9,402,950 | B2 | 8/2016 | Dilanni et al. | |
| 9,520,649 | B2 | 12/2016 | de Rochemont | |
| 9,656,017 | B2 | 5/2017 | Greene | |
| 9,857,090 | B2 | 1/2018 | Golden et al. | |
| 2001/0048969 | A1 | 12/2001 | Constantino et al. | |
| 2001/0056258 | A1 | 12/2001 | Evans | |
| 2002/0047768 | A1 | 4/2002 | Duffy | |
| 2002/0070983 | A1 | 6/2002 | Kozub et al. | |
| 2002/0173769 | A1 | 11/2002 | Gray et al. | |
| 2002/0190818 | A1 | 12/2002 | Endou et al. | |
| 2003/0034124 | A1 | 2/2003 | Sugaya et al. | |
| 2003/0040715 | A1 | 2/2003 | DAntonio et al. | |
| 2003/0122647 | A1 | 7/2003 | Bu | |
| 2003/0148024 | A1 | 8/2003 | Kodas et al. | |
| 2003/0170436 | A1 | 9/2003 | Sumi et al. | |
| 2003/0221621 | A1 | 12/2003 | Pokharna et al. | |
| 2004/0064088 | A1 | 4/2004 | Gorman et al. | |
| 2004/0068224 | A1 | 4/2004 | Couvillon, Jr. et al. | |
| 2004/0069044 | A1 | 4/2004 | Lavi et al. | |
| 2005/0020980 | A1 | 1/2005 | Inoue et al. | |
| 2005/0134609 | A1 | 6/2005 | Yu | |
| 2005/0182366 | A1 | 8/2005 | Vogt et al. | |
| 2005/0203461 | A1 | 9/2005 | Flaherty et al. | |
| 2005/0238507 | A1 | 10/2005 | Dilanni et al. | |
| 2005/0262451 | A1 | 11/2005 | Remignanti et al. | |
| 2006/0010098 | A1 * | 1/2006 | Goodnow | G06F 13/20 |
| 2006/0041229 | A1 | 2/2006 | Garibotto et al. | |
| 2006/0079765 | A1 | 4/2006 | Neer et al. | |
| 2006/0086994 | A1 | 4/2006 | Viefers et al. | |
| 2006/0134491 | A1 | 6/2006 | Hilchenko et al. | |
| 2006/0178633 | A1 | 8/2006 | Garibotto et al. | |
| 2007/0100635 | A1 | 5/2007 | Mahajan et al. | |
| 2007/0118405 | A1 | 5/2007 | Campbell et al. | |
| 2007/0166453 | A1 | 7/2007 | Van Duren et al. | |
| 2007/0259768 | A1 | 11/2007 | Kear et al. | |
| 2008/0051738 | A1 | 2/2008 | Griffin | |
| 2008/0114304 | A1 | 5/2008 | Nalesso et al. | |
| 2008/0160492 | A1 | 7/2008 | Campbell et al. | |
| 2008/0172028 | A1 | 7/2008 | Blomquist | |
| 2009/0326472 | A1 | 12/2009 | Carter | |
| 2010/0017141 | A1 | 1/2010 | Campbell et al. | |
| 2010/0036326 | A1 | 2/2010 | Matusch | |
| 2010/0064243 | A1 | 3/2010 | Buck et al. | |
| 2010/0077198 | A1 | 3/2010 | Buck et al. | |
| 2010/0114026 | A1 | 5/2010 | Karratt | |
| 2010/0185183 | A1 | 7/2010 | Alme et al. | |
| 2010/0241066 | A1 | 9/2010 | Hansen et al. | |
| 2011/0049394 | A1 | 3/2011 | de Rochemont | |
| 2011/0065224 | A1 | 3/2011 | Bollman et al. | |
| 2011/0071765 | A1 | 3/2011 | Yodfat et al. | |
| 2011/0118699 | A1 | 5/2011 | Yodfat et al. | |
| 2011/0144586 | A1 | 6/2011 | Michaud et al. | |
| 2012/0124521 | A1 | 5/2012 | Guo | |
| 2012/0150446 | A1 | 6/2012 | Chang et al. | |
| 2012/0226259 | A1 | 9/2012 | Yodfat et al. | |
| 2012/0238851 | A1 * | 9/2012 | Kamen | A61M 5/14244<br>604/151 |
| 2012/0245447 | A1 * | 9/2012 | Karan | G01N 33/48792<br>600/365 |
| 2012/0250449 | A1 | 10/2012 | Nakano | |
| 2013/0172695 | A1 | 7/2013 | Nielsen et al. | |
| 2013/0172710 | A1 | 7/2013 | Mears et al. | |
| 2013/0245545 | A1 | 9/2013 | Arnold et al. | |
| 2013/0296792 | A1 | 11/2013 | Cabiri | |
| 2013/0298080 | A1 | 11/2013 | Griffin et al. | |
| 2013/0332874 | A1 | 12/2013 | Rosinko et al. | |
| 2013/0346858 | A1 | 12/2013 | Neyrinck | |
| 2014/0012117 | A1 * | 1/2014 | Mensinger | G16H 40/67<br>600/365 |
| 2014/0018730 | A1 | 1/2014 | Muller-Pathle | |
| 2014/0032549 | A1 | 1/2014 | McDaniel et al. | |
| 2014/0088428 | A1 | 3/2014 | Yang et al. | |
| 2014/0108046 | A1 | 4/2014 | Cabrera et al. | |
| 2014/0129951 | A1 | 5/2014 | Amin et al. | |
| 2014/0142508 | A1 | 5/2014 | Dilanni et al. | |
| 2014/0171901 | A1 | 6/2014 | Langsdorf et al. | |
| 2015/0025503 | A1 | 1/2015 | Searle et al. | |
| 2015/0041498 | A1 | 2/2015 | Kakiuchi et al. | |
| 2015/0134353 | A1 | 5/2015 | Ferrell et al. | |
| 2015/0193585 | A1 | 7/2015 | Sunna | |
| 2015/0202386 | A1 | 7/2015 | Brady et al. | |
| 2015/0205509 | A1 | 7/2015 | Scriven et al. | |

(56) References Cited

U.S. PATENT DOCUMENTS

| | | | |
|---|---|---|---|
| 2015/0205511 A1 | 7/2015 | Vinna et al. | |
| 2015/0205930 A1* | 7/2015 | Shaanan | G06Q 10/00 705/2 |
| 2015/0301691 A1 | 10/2015 | Qin | |
| 2015/0331995 A1 | 11/2015 | Zhao et al. | |
| 2015/0350861 A1* | 12/2015 | Soli | H04M 1/72421 455/26.1 |
| 2015/0356250 A1 | 12/2015 | Polimeni | |
| 2015/0366945 A1 | 12/2015 | Greene et al. | |
| 2016/0019352 A1 | 1/2016 | Cohen et al. | |
| 2016/0220181 A1 | 8/2016 | Rigooard et al. | |
| 2016/0259889 A1 | 9/2016 | Murtha et al. | |
| 2017/0021096 A1 | 1/2017 | Cole et al. | |
| 2017/0128007 A1* | 5/2017 | Hayter | G09B 5/02 |
| 2017/0131887 A1 | 5/2017 | Kim et al. | |
| 2017/0216524 A1 | 8/2017 | Haider et al. | |
| 2017/0239415 A1 | 8/2017 | Hwang et al. | |
| 2018/0040255 A1 | 2/2018 | Freeman et al. | |
| 2018/0075200 A1 | 3/2018 | Davis et al. | |
| 2018/0169334 A1 | 6/2018 | Grosman et al. | |
| 2018/0200441 A1 | 7/2018 | Desborough et al. | |
| 2018/0296757 A1 | 10/2018 | Finan et al. | |
| 2018/0307515 A1 | 10/2018 | Meller et al. | |
| 2019/0095052 A1 | 3/2019 | De Wever et al. | |
| 2019/0132801 A1 | 5/2019 | Kamath et al. | |
| 2019/0184091 A1 | 6/2019 | Sjolund et al. | |
| 2019/0320310 A1* | 10/2019 | Horelik | H04M 3/5116 |
| 2019/0321545 A1 | 10/2019 | Saint | |
| 2019/0374714 A1 | 12/2019 | Rioux et al. | |
| 2020/0001006 A1 | 1/2020 | Pizzochero et al. | |
| 2020/0101225 A1 | 4/2020 | O'Connor et al. | |
| 2020/0113515 A1 | 4/2020 | O'Connor et al. | |
| 2021/0085869 A1* | 3/2021 | El-Khatib | A61M 5/142 |
| 2022/0189604 A1* | 6/2022 | El-Khatib | A61M 5/1723 |

FOREIGN PATENT DOCUMENTS

| | | | |
|---|---|---|---|
| EP | 0026056 | A1 | 4/1981 |
| EP | 0867196 | A2 | 9/1998 |
| EP | 0939451 | A1 | 9/1999 |
| EP | 1177802 | A1 | 2/2002 |
| EP | 1376759 | A2 | 1/2004 |
| EP | 2468338 | A1 | 6/2012 |
| EP | 2703024 | A1 | 3/2014 |
| EP | 3193979 | A1 | 7/2017 |
| EP | 3607985 | A1 | 2/2020 |
| FR | 2096275 | A5 | 2/1972 |
| GB | 1125897 | A | 9/1968 |
| JP | 2005326943 | A | 11/2005 |
| JP | 2008513142 | A | 5/2008 |
| JP | 2010506279 | A | 2/2010 |
| JP | 2019-509085 | A | 4/2019 |
| JP | 2020-501236 | A | 1/2020 |
| JP | 2020-034981 | A | 3/2020 |
| JP | 2020-078648 | A | 5/2020 |
| WO | 200048112 | A2 | 9/1968 |
| WO | 8606796 | A1 | 11/1986 |
| WO | 9855073 | A1 | 12/1998 |
| WO | 9910040 | A1 | 3/1999 |
| WO | 9910049 | A1 | 3/1999 |
| WO | 9962576 | A1 | 12/1999 |
| WO | 2001078812 | A1 | 10/2001 |
| WO | 0226282 | A2 | 4/2002 |
| WO | 2002076535 | A1 | 10/2002 |
| WO | 2003097133 | A1 | 11/2003 |
| WO | 2007066152 | A2 | 6/2007 |
| WO | 2009039203 | A2 | 3/2009 |
| WO | 2010022069 | A2 | 2/2010 |
| WO | 2010077279 | A1 | 7/2010 |
| WO | 2010139793 | A1 | 12/2010 |
| WO | 2011031458 | A1 | 3/2011 |
| WO | 2011075042 | A1 | 6/2011 |
| WO | 2011133823 | A1 | 10/2011 |
| WO | 2012073032 | A1 | 6/2012 |
| WO | 2013050535 | A2 | 4/2013 |
| WO | 2014029416 | A1 | 2/2014 |
| WO | 2014149357 | A1 | 9/2014 |
| WO | 2014179774 | A1 | 11/2014 |
| WO | 2015117082 | A1 | 8/2015 |
| WO | 2015117854 | A1 | 8/2015 |
| WO | 2015167201 | A1 | 11/2015 |
| WO | 2015177082 | A1 | 11/2015 |
| WO | 2016041873 | A1 | 3/2016 |
| WO | 2017123525 | A1 | 7/2017 |
| WO | 2017187177 | A1 | 11/2017 |
| WO | 2019094440 | A1 | 5/2019 |

OTHER PUBLICATIONS

Bardi et al., "Plane Wave Scattering From Frequency-Selective Surfaces by the Finite-Element Method" IEEE Transactions on Magnetics 38(2):641-644 (2002).

Chappell et al., "Composite Metamaterial Systems for Two-Dimensional Periodic Structures" IEEE, 3840387 (2002).

Cheng et al., "Preparation and Characterization of (Ba, Sr) TiO3 thin films using interdigitial electrodes" Microelectronic Engineering, 66:872-879 (2003).

Clavijo et al., "Design Methodology for Sievenpiper High-Impedance Surfaces: An Artificial Magnetic Conductor for Positive Gain Electrically Small Antennas" IEEE Transactions on Antennas and Propagation, 51(10):2678-2690 (2003).

Diaz et al., "Magnetic Loading of Antificial Magnetic Conductors for Bandwidth Enhancement" IEEE, 431-434 (2003).

Hansen "Effect of a High-Impedance Screen on a Dipole Antenna" IEEE Antennas and Wireless Propagation Letter, 1:46-49 (2002).

Joshi et al., "Processing and Characterization of Pure and Doped Ba0.6Sr0.4TiO3 thin films for tunable microsave applications" Mat. Res. Soc. Symp. Proc., 656E:DD4.9.1-DD4.9.6 (2001).

Kern et al., "Active Negative Impedance Loaded EBG Structures for the Realization of Ultra-Wideband Artificial Magnetic Conductors" IEEE, 427-430 (2003).

Kern et al., "The Synthesis of Metamaterial Ferrities for RF Applications Using Electromagnetic Bandgap Structures" IEEE, 497-500 (2003).

Kern et al., "Ultra-thin Electromagnetic Bandgap Absorbers Synthesized via Genetic Algorithms" IEEE, 1119-1122 (2003).

Kuhn et al., "Characterization of novel mono- and bifacially active semi-transparent crystalline silicon solar cells" IEEE Transactions on Electron Devices, 46(10): 2013-2017 (1999).

Kretly et al., "The Influence of the Height Variation on the Frequency Bandgap in an AMC, Artificial magnetic Conductor for Wireless Applications: an EM Experimental Design Approach" Proceedings SBMO/IEEE MTT-S IMOC, 219-223 (2003).

Lee et al., "Investigation of Electromagnetic Bandgap (EBG) Structures for Antenna Pattern Control" IEEE, 1115-1118 (2003).

McKinzie III et al., "Mitigation of Multipath Through the Use of an Artificial Magnetic Conductor for Precision CPS Surveying Antennas" IEEE, 640-643.

Monorciho et al., "Synthesis of Artificial Magnetic Conductors by Using Multilatered Frequency Selective Surfaces" IEEE Antennas and Wireless Propagation Letters, 1:196-1999 (2002).

Mosallaei et al. "Periodic Bandgap and Effective Dielectric Materials in Electromagnetics: Characterization and Applications in Nanocavities and Waveguides" IEEE Transcations on Antennas and Propagation, 51(3):549-563 (2003).

Pontes et al., "Study of the dielectric and ferroelectric properties of chemically processed BaxSr1-xTiO3 thin films" Thin Solid Films, 386(2)91-98 (2001).

Rogers et al., "AMCs Comprised of Interdigital Capacitor FSS Layers Enable Lower Cost Applications" IEEE, 411-414 (2003).

Sievenpiper et al., "Two-Dimensional Beam Steering Using an Electrically Tunable Impedance Surface" IEEE Transactions on Antennas and Propagation, 51(10):2713-2722(2003).

Sun et al., "Efficiency of Various Photonic Bandgap (PBG) Structures" 3rd Int'l. Conf. on Microwave and Millimeter Wave Technology Proceedings, 1055-1058 (2002).

(56) References Cited

OTHER PUBLICATIONS

Tsunemine et al., "Pt/BaxSr(1-x)TiO3/Pt Capacitor Technology for 0.15 micron Embedded Dynamic Random Access Memory" Jap. J. Appl. Phys., 43(5A):2457-2461 (2004).
Vest "Metallo-organic decomposition (MOD) processing of ferroelectric and electro-optic films: A review" Ferroelectrics, 102(1):53-68 (1990).
Viviani et al., "Positive Temperature Coefficient of Electrical Resistivity below 150k of Barium Strontium Titanate" J. Amer. Ceram. Soc. 87(4): 756-758 (2004).
Weily et al., "Antennas Based on 2-D and 3-D Electromagnetic Bandgap Materials" IEEE, 847-850 (2003).
Yang et al., "Surface Waves of Printed Antennas on Planar Artificial Periodic Dielectric Structures" IEEE Transactions on Antennas and Propagation 49(3): 444-450 (2001).
Zhang et al., "Planar Artificial magnetic Conductors and Patch Antennas" IEEE Transactions on Antennas and Propagation, 51(10):2704-2712 (2003).
Ziroff et al., "A Novel Approach for LTCC Packaging Using a PBG Structure for Shielding and Package Mode Suppression" 33rd European Microwave Conference—Munich 419-422 (2003).
International Search Report and Written Opinion for Application No. PCT/US17/61336, mailed on Jan. 25, 2018, 9 pages.
"Graph Chart." iconfinder.com. Aug. 15, 2016. Accessed Apr. 21, 2020. Available online at URL: https://www.iconfinder.com/iconsets/graph-chart-2>.
"Circular Progress Indicator Component for React." reactscript.com. Dec. 2, 2016. Accessed Sep. 9, 2020. Available online at URL: <http://reactscripts.com/circular-progress-indicator-component-react/>.
Kruska, Michal. "Circle progress bar." dribbble.com. Oct. 18, 2012. Accessed Apr. 21, 2020. Available online at URL: <https://dribbble.com/shots/775718-Circle-progress-bar>.
"C# custom control <circle progress bar> Xamarian Forms." stackoverflow.com. May 22, 2016. Accessed Apr. 21, 2020. Available online at URL: <https://stackoverflow.com/questions/37379868/c-sharp-custom-control-circle-progress-bar-kamarin-forms>.
International Search Report and Written Opinion for Application No. PCT/US2021/047685 mailed on Dec. 6, 2021, 15 pages.
International Search Report and Written Opinion for the International Patent Application No. PCT/US2021/055745, mailed Feb. 14, 2022, 13 pages.
"Circular Loader." dribbble.com. Nov. 19, 2015. Accessed Jul. 24, 2019. Available online at URL: https://dribbble.com/shots/2362441-Circular-Loader (Year: 2015).
"Creating NSSlider with 2 knobs (range slider)." stackoverflow.com. May 6, 2015. Accessed Oct. 25, 2018. Available online at URL: <https://stackoverflow.com/questions/30082809/creating-nsslider-with-2- - knobs-range-slider> (Year: 2015).
"How to do a Round Slider." freecodecamp.org. Comment from Aug. 2018. Accessed Jul. 24, 2019. Available online at URL: https://www.freecodecamp.org/forum/t/how-to-do-a-round-slider/220375 (Year: 2018).
"Tick and cross circle shape icon . . . " depositphotos.com. Aug. 27, 2016. Accessed Feb. 1, 2019. Available online at URL :<https://depositphotos.com/121291612/stock-illustration-tick-and-cross-circle-shape.html> (Year: 2016).
"Vector-Vector Illustration of Preloader / Buffer Shapes, or Dials with Knobs." 123rf.com. Date not available. Accessed Oct. 25, 2018. Available online at URL: <https://www.123rf.com/photo_37292689_stock-vector-vector-illustration- - of-preloader-buffer-shapes-or-dials-with-knobs.html> (Year: N/A).
Gad, Tess. "Framer Cheat Sheet: Slider & Range Sliders." blog.framer.com. Jun. 12, 2017. Accessed Oct. 25, 2018. Available online at URL: <https://blog.framer.com/framer-cheat-sheets-slider-range-sliders-3dd2e5a4621d> (Year: 2017).
Obaizamomwan, Osas. "How to use the new features in iOS 9 Notes App." iphonehacks.com. Sep. 12, 2015. Accessed Apr. 24, 2018. Available online at URL: https://www.iphonehacks.com/2015/09/how-to-use-the-new-features-in-ios-9-notes-app.html.
International Search Report and Written Opinion for the International Patent Application No. PCT/US21/064056, mailed Apr. 4, 2022, 12 pages.
International Search Report and Written Opinion for the International Patent Application No. PCT/US21/064170, mailed Apr. 20, 2022, 12 pages.
Anonymous: "AndroidAPS ComponentOverview", AndroidAPS documentation, Nov. 12, 2020 (Nov. 12, 2020), pp. 1-7, Retrieved from the Internet: URL:https://github.com/openaps/AndroidAPSdocs/blob/199ef86a900adf4b3d9c32f605eb11047bd3d62f/docs/EN/Module/module.rst [retrieved on Apr. 11, 2022] the whole document.
Team Section—Qonto, by Christophe Kerebel, dated Dec. 12, 2018, dribbble.com [online]. Retrieved Jul. 1, 2022 from Internet <URL: https://dribbble.com/shots/5676730-Team-Section-Qonto> (Year: 2018).

* cited by examiner

2000

2300

MEDICATION DELIVERY SYSTEM WITH GRAPHICAL USER INTERFACE

RELATED APPLICATIONS

This application claims the benefit of U.S. Provisional Patent Application No. 63/132,694, filed Dec. 31, 2020, the contents of which are incorporated herein by reference in their entirety.

TECHNICAL FIELD

Embodiments herein generally relate to automated medication delivery and, more particularly, to wireless medication delivery systems using wearable medication delivery devices and to a user application for controlling the wearable medication delivery devices.

BACKGROUND

Wearable medication delivery systems, and, in particular, systems for delivering insulin, are typically capable of monitoring a user's glucose levels, determining an appropriate level of insulin for the user based on the monitored glucose levels, and subsequently dispensing the insulin to the user. Sophisticated control algorithms needed for these systems generally require powerful computing resources and significant power resources. As a result, conventional medication delivery systems do not provide for wireless communications between system components, fully autonomous operation, enhanced user experiences involving ubiquitous electronic devices like smartphones, and improved security features. A need therefore exists for an insulin management system that includes such features.

BRIEF DESCRIPTION OF THE DRAWINGS

In the drawings, like reference characters generally refer to the same parts throughout the different views. In the following description, various embodiments of the present invention are described with reference to the following drawings, in which:

FIGS. 2(*c-d*) illustrate first and second views of the device of FIGS. 2(*a-b*), showing an add-on module.

FIGS. 25(*b-c*) show screens providing the ability to change the time zone upon which the calculations for the delivery of the insulin are based.

DETAILED DESCRIPTION

Various embodiments of the present invention include systems and methods for delivering a medication to a user using a wearable drug device (sometimes referred to herein as a "pod"), either autonomously, or in accordance with a wireless signal received from an electronic device. In various embodiments, the electronic device may be a user device comprising a smartphone, a smart watch, a smart necklace, a module attached to the drug delivery device, or any other type or sort of electronic device that may be worn or carried on the body of the user and that executes an algorithm that computes the times and dosages of delivery of the medication. For example, the user device may execute an "artificial pancreas" algorithm that computes the times and dosages of delivery of insulin. The user device may also be in communication with a sensor, such as a glucose sensor, that collects data on a physical attribute or condition of the user, such as a glucose level. The sensor may be disposed in or on the body of the user and may be part of the drug delivery device or may be a separate device. Alternately, the drug delivery device may be in communication with the sensor in lieu of or in addition to the communication between the sensor and the user device. The communication may be direct (if, e.g., the sensor is integrated with or otherwise a part of the drug delivery device) or remote/wireless (if, e.g., the sensor is disposed in a different housing than the medical device). In these embodiments, the sensor and/or drug delivery device contain computing hardware (e.g., a processor, memory, firmware, etc.) that executes some or all of the algorithm that computes the times and dosages of delivery of the medication.

Figure 1:
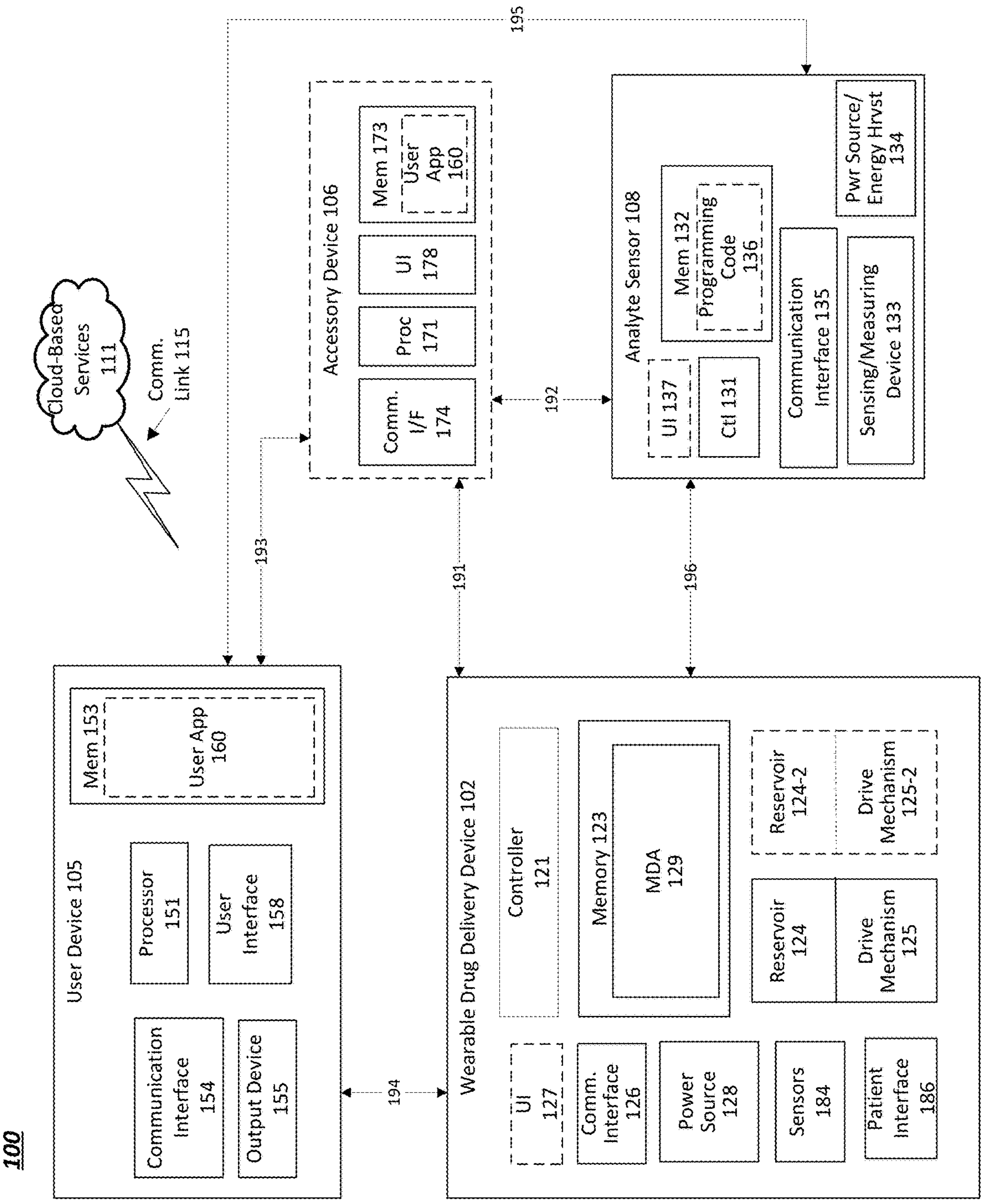
FIG. 1 illustrates a functional block diagram of an exemplary system.

FIG. 1 illustrates a functional block diagram of an exemplary drug delivery system 100 suitable for implementing the systems and, methods described herein. The drug delivery system 100 may implement (and/or provide functionality for) a medication delivery algorithm to govern or control automated delivery of a drug or medication, such as insulin, to a user (e.g., to maintain euglycemia—a normal level of glucose in the blood). The drug delivery system 100 may be an automated drug delivery system that may include a wearable drug delivery device 102, an analyte sensor 108, and a user device 105.

The drug delivery system 100, in an optional example, may also include an accessory device 106, such as a smartwatch, a personal assistant device or the like, which may communicate with the other components of system 100 via either a wired or wireless communication links 191-193.

The user device 105 may be a computing device such as a smartphone, a tablet, a personal diabetes management (PDM) device, a dedicated diabetes therapy management device, or the like. In an example, user device 105 may include a processor 151, device memory 153, a user interface 158, and a communication interface 154. The user device 105 may also contain analog and/or digital circuitry that may be implemented as a processor 151 for executing processes based on programming code stored in device memory 153, such as user application 160 to manage a user's blood glucose levels and for controlling the delivery of the drug, medication, or therapeutic agent to the user, as well for providing other functions, such as calculating carbohydrate-compensation dosage, a correction bolus dosage and the like as discussed below. The user device 105 may be used to program, adjust settings, and/or control operation of the wearable drug delivery device 200*a*, 200*b* and/or the analyte sensor 103 as well as the optional smart accessory device 106.

The processor 151 may also be configured to execute programming code stored in device memory 153, such as the user app 160. The user app 160 may be a computer application that is operable to deliver a drug based on information received from the analyte sensor 103, the cloud-based services 111 and/or the user device 105 or optional accessory device 106. The memory 153 may also store programming code to, for example, operate the user interface 158 (e.g., a touchscreen device, a camera or the like), the communication interface 154 and the like. The processor 151, when executing user app 160, may be configured to implement indications and notifications related to meal ingestion, blood glucose measurements, and the like. The user interface 158 may be under the control of the processor 151 and be configured to present a graphical user interface that enables the input of a meal announcement, adjust setting selections and the like as described herein.

In a specific example, when the user app 160 is an insulin delivery application, the processor 151 is also configured to execute a diabetes treatment plan (which may be stored in a memory) that is managed by user app 160. In addition to the functions mentioned above, when user app 160 is an insulin delivery application, it may further provide functionality to determine a carbohydrate-compensation dosage, a correction bolus dosage and determine a basal dosage according to a diabetes treatment plan. In addition, as an insulin delivery application, user app 160 provides functionality to output signals to the wearable drug delivery device 200*a*, 200*b* via communications interface 154 to deliver the determined bolus and basal dosages.

The communication interface 154 may include one or more transceivers that operate according to one or more radio-frequency protocols. In one embodiment, the transceivers may comprise a cellular transceiver and a Bluetooth® transceiver. The communication interface 154 may be configured to receive and transmit signals containing information usable by user app 160.

User device 105 may be further provided with one or more output devices 155 which may be, for example, a speaker or a vibration transducer, to provide various signals to the user.

An exemplary embodiment of the wearable drug delivery device 102 may include a reservoir 124 and drive mechanism 125, which are controllable by controller 121, executing a medication delivery algorithm (MDA) 129 stored in memory 123. Alternatively, controller 121 may act to control reservoir 124 and drive mechanism 125 based on signals received from user app 160 executing on a user device 105 and communicated to wearable drug delivery device 102 via communication link 194.

Wearable drug delivery device 102 may further include a user interface 127, a patient interface 186, a communication interface 126, device sensors 184 and a power source 128.

In an alternate embodiment, wearable drug delivery device 102 may also include an optional second reservoir 124-2 and second drive mechanism 125-2 which enables the independent delivery of two different liquid drugs. As an example, reservoir 124 may be filled with insulin, while reservoir 124-2 may be filled with Pramlintide or GLP-1. In some embodiments, each of reservoirs 124, 124-2 may be configured with a separate drive mechanism 125, 125-2, respectively, which may be separately controllable by controller 121 under the direction of MDA 129. Both reservoirs 124, 124-2 may be connected to a common patient interface 186.

Wearable drug delivery device 102 may be optionally configured with a user interface 127 providing a means for receiving input from the user and a means for outputting information to the user. User interface 127 may include, for example, light-emitting diodes, buttons on a housing of the wearable drug delivery device 102, a sound transducer, a micro-display, a microphone, an accelerometer for detecting motions of the device of user gestures (e.g., tapping on a housing of the device) or any other type of interface device that is configured to allow a user to enter information and/or allow the wearable drug delivery device 102 to output information for presentation to the user (e.g., alarm signals or the like).

The wearable drug delivery device 102 includes a patient interface 186 for interfacing with the user to deliver the liquid drug. Patient interface may be, for example, a needle or cannula for delivering the drug into the body of the user (which may be done subcutaneously, intraperitoneally, or intravenously). Wearable drug delivery device 102 further includes a means for inserting the patient interface 186 into the body of the user which may comprise, in one embodiment, an actuator that insert the needle/cannula under the skin of the user and thereafter retracts the needle, leaving the cannula in place.

In one embodiment, the wearable drug delivery device 102 includes a communication interface 126, which may be a transceiver that operates according to one or more radio-frequency protocols, such as Bluetooth, Wi-Fi, near-field communication, cellular, or the like. The controller 121 may, for example, communicate with user device 105 and an analyte sensor 108 via the communication interface 126.

In some embodiments, wearable drug delivery device 102 may be provided with one or more sensors 184. The sensors 184 may include one or more of a pressure sensor, a power sensor, or the like that are communicatively coupled to the controller 121 and provide various signals. For example, a pressure sensor may be configured to provide an indication of the fluid pressure detected in a fluid pathway between the patient interface 186 and reservoir 124. The pressure sensor may be coupled to or integral with the actuator for inserting the patient interface 186 into the user. In an example, the controller 121 may be operable to determine a rate of drug infusion based on the indication of the fluid pressure. The rate of drug infusion may be compared to an infusion rate threshold, and the comparison result may be usable in determining an amount of insulin onboard (JOB) or a total daily insulin (TDI) amount.

Wearable drug delivery device 102 further includes a power source 128, such as a battery, a piezoelectric device, an energy harvesting device, or the like, for supplying electrical power to controller 121, memory 123, drive mechanisms 125 and/or other components of the wearable drug delivery device 102.

The communication link 115 that couples the cloud-based services 111 to the respective devices 102, 105, 106, 108 of system 100 may be a cellular link, a Wi-Fi link, a Bluetooth link, or a combination thereof. Services provided by cloud-based services 111 may include data storage that stores anonymized data, such as blood glucose measurement values, historical IOB or TDI, prior carbohydrate-compensation dosage, and other forms of data. In addition, the cloud-based services 111 may process the anonymized data from multiple users to provide generalized information related to TDI, insulin sensitivity, IOB and the like.

The wireless communication links 191-196 may be any type of wireless link operating using known wireless communication standards or proprietary standards. As an example, the wireless communication links 191-196 may provide communication links based on Bluetooth®, Zigbee®, Wi-Fi, a near-field communication standard, a cellular standard, or any other wireless protocol via the respective communication interfaces 154, 174, 126 and 135.

The wearable drug delivery device 102 may be configured to perform and execute processes required to deliver doses of the medication to the user without input from the user device 105 or the optional accessory device 106. As explained in more detail, MDA 129 may be operable, for example, to determine an amount of insulin to be delivered, JOB, insulin remaining, and the like and to cause controller 121 to active drive mechanism 125 to deliver the medication from reservoir 124. MDA 129 may take as input data received from the analyte sensor 108 or from user app 160.

The reservoirs 124, 124-2 may be configured to store drugs, medications or therapeutic agents suitable for automated delivery, such as insulin, Pramlintide, GLP-1, co-formulations of insulin and GLP-1, morphine, blood pressure medicines, chemotherapy drugs, fertility drugs or the like.

The wearable drug delivery device 102 may be attached to the body of a user, such as a patient or diabetic, at an attachment location and may deliver any therapeutic agent, including any drug or medicine, such as insulin or the like, to a user at or around the attachment location. A surface of the wearable drug delivery device 102 may include an adhesive to facilitate attachment to the skin of a user.

When configured to communicate with an external device, such as the user device 105 or the analyte sensor 108, the wearable drug delivery device 102 may receive signals via link 194 from the user device 105 or via link 196 from the analyte sensor 108. The controller 121 of the wearable drug delivery device 102 may receive and process the signals from the respective external devices as well as implementing delivery of a drug to the user according to a diabetes treatment plan or other drug delivery regimen, implemented by MDA 129 or user application 160.

In an operational example, the controller 121, when executing MDA 129 may generate and output a control signal operable to actuate the drive mechanism 125 to deliver a carbohydrate-compensation dosage of insulin, a correction bolus, a revised basal dosage, co-formulations of various liquid drugs, or the like.

The accessory device 106 may be, for example, an Apple Watch®, other wearable smart device, including eyeglasses, smart jewelry, a global positioning system-enabled wearable, a wearable fitness device, smart clothing, or the like. Similar to user device 105, the accessory device 106 may also be configured to perform various functions including controlling the wearable drug delivery device 200*a*, 200*b*. For example, the accessory device 106 may include a communication interface 174, a processor 171, a user interface 178 and a memory 173. The user interface 178 may be a graphical user interface presented on a touchscreen display of the smart accessory device 106. The memory 173 may store programming code to operate different functions of the smart accessory device 106 as well as an instance of the user app 160, or a pared-down versions of user app 160 with reduced functionality.

The analyte sensor 108 may include a controller 131, a memory 132, a sensing/measuring device 133, an optional user interface 137, a power source/energy harvesting circuitry 134, and a communication interface 135. The analyte sensor 108 may be communicatively coupled to the processor 151 of the management device 105 or controller 121 of the wearable drug delivery device 200*a*, 200*b*. The memory 132 may be configured to store information and programming code 136.

The analyte sensor 108 may be configured to detect multiple different analytes, such as lactate, ketones, uric acid, sodium, potassium, alcohol levels or the like, and output results of the detections, such as measurement values or the like. The analyte sensor 108 may, in an exemplar embodiment, be configured to measure a blood glucose value at a predetermined time interval, such as every 5 minutes, or the like. The communication interface 135 of analyte sensor 108 may have circuitry that operates as a transceiver for communicating the measured blood glucose values to the user device 105 over a wireless link 195 or with wearable drug delivery device 200*a*, 200*b* over the wireless communication link 108. While referred to herein as an analyte sensor 108, the sensing/measuring device 133 of the analyte sensor 108 may include one or more additional sensing elements, such as a glucose measurement element, a heart rate monitor, a pressure sensor, or the like. The controller 131 may include discrete, specialized logic and/or components, an application-specific integrated circuit, a microcontroller or processor that executes software instructions, firmware, programming instructions stored in memory (such as memory 132), or any combination thereof.

Similar to the controller 221 of wearable drug delivery device 200*a*, 200*b*, the controller 131 of the analyte sensor 108 may be operable to perform many functions. For example, the controller 131 may be configured by programming code 136 to manage the collection and analysis of data detected by the sensing and measuring device 133.

Although the analyte sensor 108 is depicted in FIG. 1 as separate from the wearable drug delivery device 102, in various embodiments, the analyte sensor 108 and wearable drug delivery device 102 may be incorporated into the same unit. That is, in various examples, the analyte sensor 108 may be a part of and integral with the wearable drug delivery device 102 and contained within the same housing as the wearable drug delivery device 102. In such an embodiment, the controller 221 may be able to implement the functions required for the proper delivery of the medication alone without any external inputs from user device 105, the cloud-based services 111, another sensor (not shown), the optional accessory device 106, or the like.

The user app 160 (or MDA 129) may provide periodic insulin micro-boluses based upon the predicted glucose over a 60-minute prediction horizon. Optimal post-prandial control will require the user to give meal boluses in the same manner as current pump therapy, but normal operation of the user app 160 will compensate for missed meal boluses and mitigate prolonged hyperglycemia. The user app 160 uses a control-to-target strategy that attempts to achieve and maintain a set target glucose value, thereby reducing the duration of prolonged hyperglycemia and hypoglycemia.

The user application 160 implements a graphical user interface that is the primary interface with the user and is used control a wearable drug delivery device 200*a*, 200*b*, program basal and bolus calculator settings for manual mode as well as program settings specific for automated mode (hybrid closed-loop or closed-loop).

In manual mode, user app 160 will deliver insulin at programmed basal rates and bolus amounts with the option to set temporary basal profiles. The controller 121 will also have the ability to function as a sensor-augmented pump in manual mode, using sensor glucose data provided by the analyte sensor 108 to populate the bolus calculator.

In automated mode, the user app 160 supports the use of multiple target blood glucose values. For example, in one embodiment, target blood glucose values can range from 110-150 mg/dL, in 10 mg/dL increments, in 5 mg/dL increments, or other increments, but preferably 10 mg/dL increments. The experience for the user will reflect current setup flows whereby the healthcare provider assists the user to program basal rates, glucose targets and bolus calculator settings. These in turn will inform the user app 160 for insulin dosing parameters. The insulin dosing parameters will be adapted over time based on the total daily insulin (TDI) delivered during each use of wearable drug delivery device 200*a*, 200*b*. A temporary hypoglycemia protection mode may be implemented by the user for various time durations in automated mode. With hypoglycemia protection mode, the algorithm reduces insulin delivery and is intended for use over temporary durations when insulin sensitivity is expected to be higher, such as during exercise.

User app 160, allows the use of large text, graphics, and on-screen instructions to prompt the user through the set-up processes and the use of system 100. It will also be used to program the user's custom basal insulin delivery profile, check the status, of wearable drug delivery device 200*a*, 200*b*, initiate bolus doses of insulin, make changes to a patient's insulin delivery profile, handle system alerts and alarms, and allow the user to switch between automated mode and manual mode.

In some embodiments, user device 105 and the analyte sensor 108 may not communicate directly with one another. Instead, data (e.g., blood glucose readings) from analyte sensor may be communicated to wearable drug delivery device 200*a*, 200*b* via link 196 and the relayed to user device 105 via link 194. In some embodiments, to enable communication between analyte sensor 108 and user device 105, the serial number of the analyte sensor must be entered into user app 160.

User app 160 may provide the ability to calculate a suggested bolus dose through the use of a bolus calculator. The bolus calculator is provided as a convenience to the user to aid in determining the suggested bolus dose based on ingested carbohydrates, most-recent blood glucose readings (or a blood glucose reading if using fingerstick), programmable correction factor, insulin to carbohydrate ratio, target glucose value and insulin on board (JOB). IOB is estimated by user app 160 taking into account any manual bolus and insulin delivered by the algorithm.

Various embodiments described herein include systems and methods for automatically delivering medication to a user. A sensor coupled to a user can collect information regarding the user. A controller can use the collected information to determine an amount of medication to provide the user. The controller can instruct the drug delivery device to dispense the medication to the user. The drug delivery device can be a wearable insulin pump that is directly coupled to the user. The controller can be, in whole or in part, implemented as a smartphone app. A user can be required to provide a confirmation input to allow a determined amount of insulin to be provided to the user based on detected glucose levels of the user.

Software related implementations of the techniques described herein may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

Figure 2A:
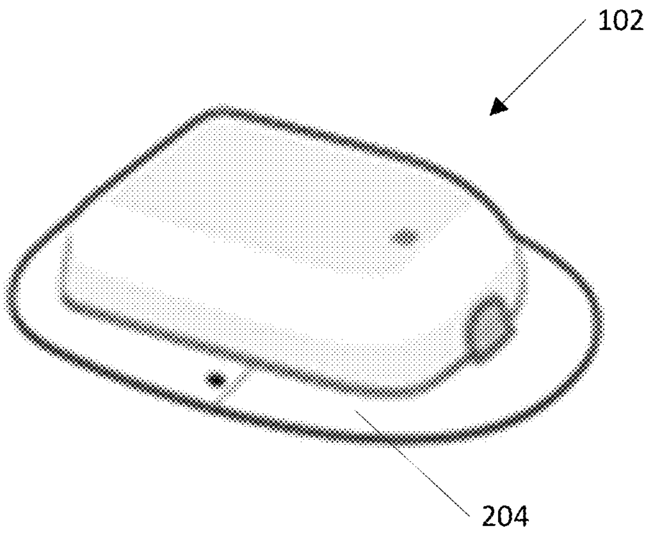
FIGS. 2(*a-b*) illustrate right-side up and upside-down perspective views of an exemplary medical device suitable for implementing the systems and methods disclosed herein.
Figure 2B:
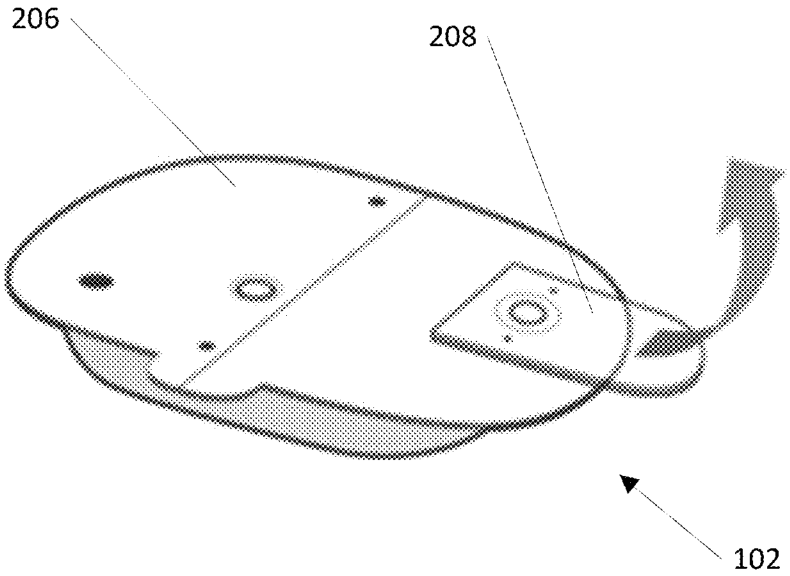
Figure 2C:
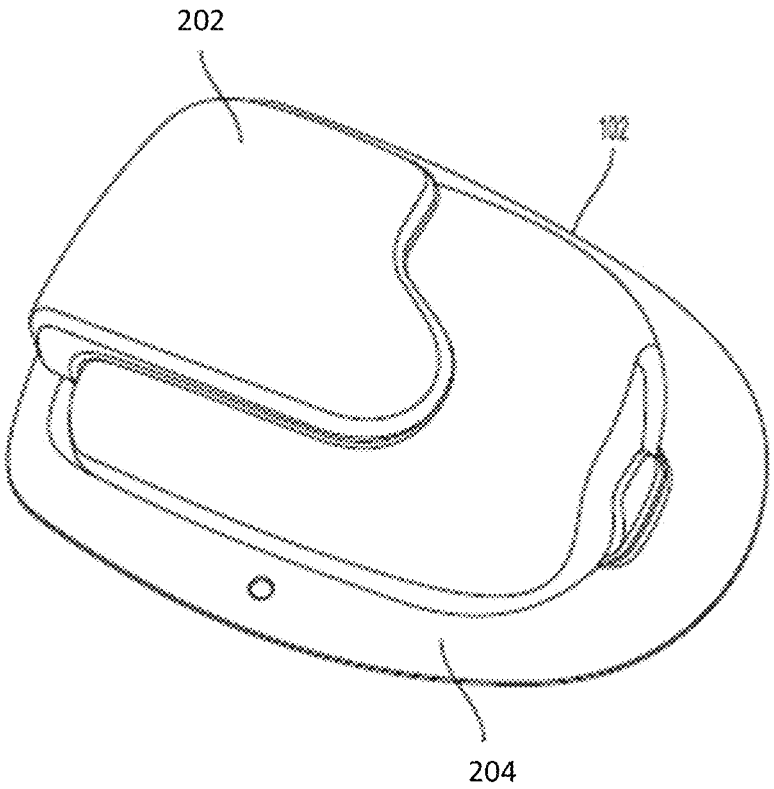
Figure 2D:
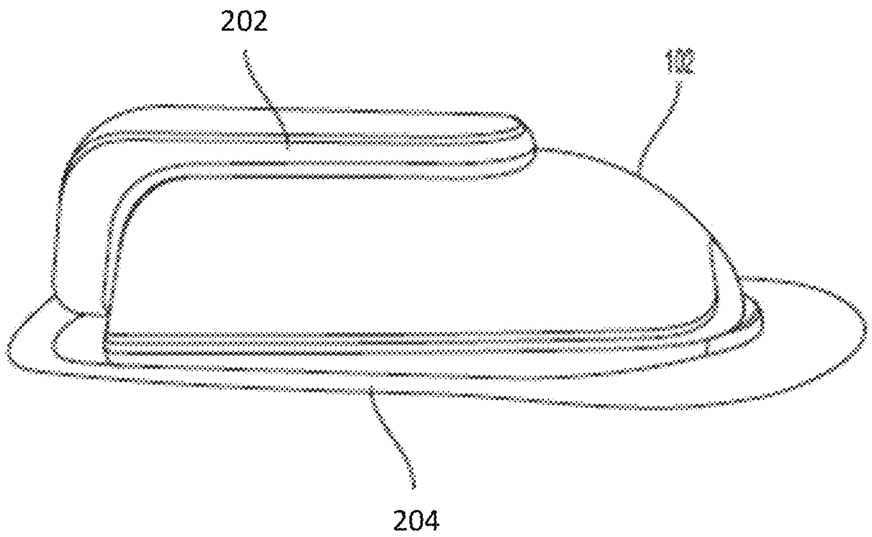

FIG. 2*a* shows a right-side up perspective view of drug delivery device 102 in which the one or more housings of drug delivery device 102 are shown. FIG. 2*b* is a perspective view showing an upside-down view of drug delivery device 102, in which adhesive backing 206 and needle/cannula cap 208 are visible. Removal of adhesive backing 206 will expose adhesive pad 204, which is used to adhere drug delivery device 102 to the user's skin. Needle/cannula cap 208 protects the needle/cannula prior to use of the device and should be removed as shown to expose the needle/cannula before adhering the device to the user's skin. The adhesive should be strong enough to adhere the drug delivery device 102 to the user's skin, but yet allows for easy removal of drug delivery device 102.

As shown in FIGS. 2(*c-d*), drug delivery device 102 can include a module 202 that is attached or coupled to the one or more housings of drug delivery device 102. Alternatively, module 202 can be located within a main housing of drug delivery device 102 or be positioned proximate to another housing of drug delivery device 102 such that there is a seamless transition between the housings of drug delivery device 102 and module 202.

Module 202 can include some or all of the features described above with reference to the user device 105 or other electronic or durable or semi-durable components. In various embodiments, the module 202 can include a transceiver to enable the drug delivery device 102 to wirelessly communicate with any other device or component depicted in FIG. 1. The module 202 and the drug delivery device 102 can communicate over any known wireless or wired communication standard or protocol. In some embodiments, for example, near-field communication is used for communication between the drug delivery device 102 and the module 202. In other embodiments, a wired connection, such as a universal serial bus connection, is used for communication between the drug delivery device 102 and the module 202.

The module 202 may contain a motor for driving a pump to push a medication into a body of the user, at least one battery and/or a supercapacitor, a printed circuit board, a memory, a processor, a wireless communications interface such as a Bluetooth transceiver, a Bluetooth Low Energy transceiver, a Body Area Network (BAN) transceiver, a cellular communication transceiver, or a WiFi transceiver, at least one antenna, sensors such as a temperature sensor, an accelerometer, a barometric pressure sensor, and/or a light sensor. The module 202 may also contain a light output, such as one or more LEDs, a vibration transducer and/or an audio output such as a speaker to provide feedback to the user. The pump may be housed in the drug delivery device 102 and may be, for example, a positive displacement pump or a reciprocating pump. The processor in the module 202 may take many different forms including a central processing unit (CPU), a graphics processing unit (GPU), an applications specific integrated circuit (ASIC), a field programmable gate array (FPGA), a special purpose controller chip or a system on a chip (SoC). The processor may execute programming instructions stored in the memory. The memory may include one or more types of storage including but not limited to random access memory (RAM), flash memory, read only memory (ROM), computer-readable memory storage and the like. The memory may also hold data and other useful information for operation of the drug delivery device 102. The drug delivery device 102 attached to the electronics module 202 may contain the other components of the drug delivery system, including, for example, a reservoir for storing the medication, a needle, a cannula, and/or a microneedle array for delivering the medication into the body of the user, and a pump for transferring the medication from the reservoir, through the needle, cannula, or microneedle array into the body of the user. The drug delivery device 102 can also include a power source such as a battery for supplying power to the pump and/or other components of the drug delivery device 102.

The module 202 may be removably attached to the drug delivery device 102 so that the module 202 may be reusable such that it may be used with a plurality of drug delivery devices 102, portions or the entirety of the latter of which may be disposable. This avoids having to reproduce all components of drug delivery deice 102, which may disposable after the medication in reservoir 124 is exhausted, thereby reducing the cost of drug delivery device 102. The module 202 may be sealed and waterproof. The module 202 may have a battery that can be rechargeable using wireless or wired charging.

In various embodiments, the drug delivery device 102 and/or module 202 described herein includes a user-input device and/or a user-output device. The user-input device can be a button disposed on the drug delivery device 102 or module 202, an acceleration sensor for sensing motion of the drug delivery device 102 or module 202, or any other such input device. The user-output device may be a speaker for playing sound, a vibration generator (e.g., a motorized gear with an offset center of gravity) for creating vibrations, metal terminals for delivering an electric shock to the body of the user, a visual display and/or one or more colored lights for providing a visual alarm, or any other such output device.

In various embodiments, when a command is received at the drug delivery device 102 from the user device 105, an action associated with the command (e.g., delivery of a bolus) is not carried out until input is received from the user. The input may include pressing the button on the drug delivery device 102 or module 202, shaking the drug delivery device 102 or module 202 (as sensed by the acceleration sensor), tapping the drug delivery device 102 or electronics module 202 one or more times (as sensed by the acceleration sensor), scanning an RFID or NFC tag, keycard, or fob, or any other such input, or pressing a button, or performing a similar action to those described above, on user device 105. If an input is not received within a certain period of time (e.g., 30 seconds, one minute, two minutes, or any other period of time), the drug delivery device 102 and/or module 202 may not carry out the drug delivery action. That is, a determined insulin dose may not be delivered and the user may be alerted accordingly. In some embodiments, the output device alerts the user to the arrival of the command at the drug delivery device 102 or module 202 by, for example, sounding an alarm, vibrating, or providing a visual signal. The output device may similarly alert the user after execution of the action and/or if the action is cancelled due to lack of user input.

Figure 3:
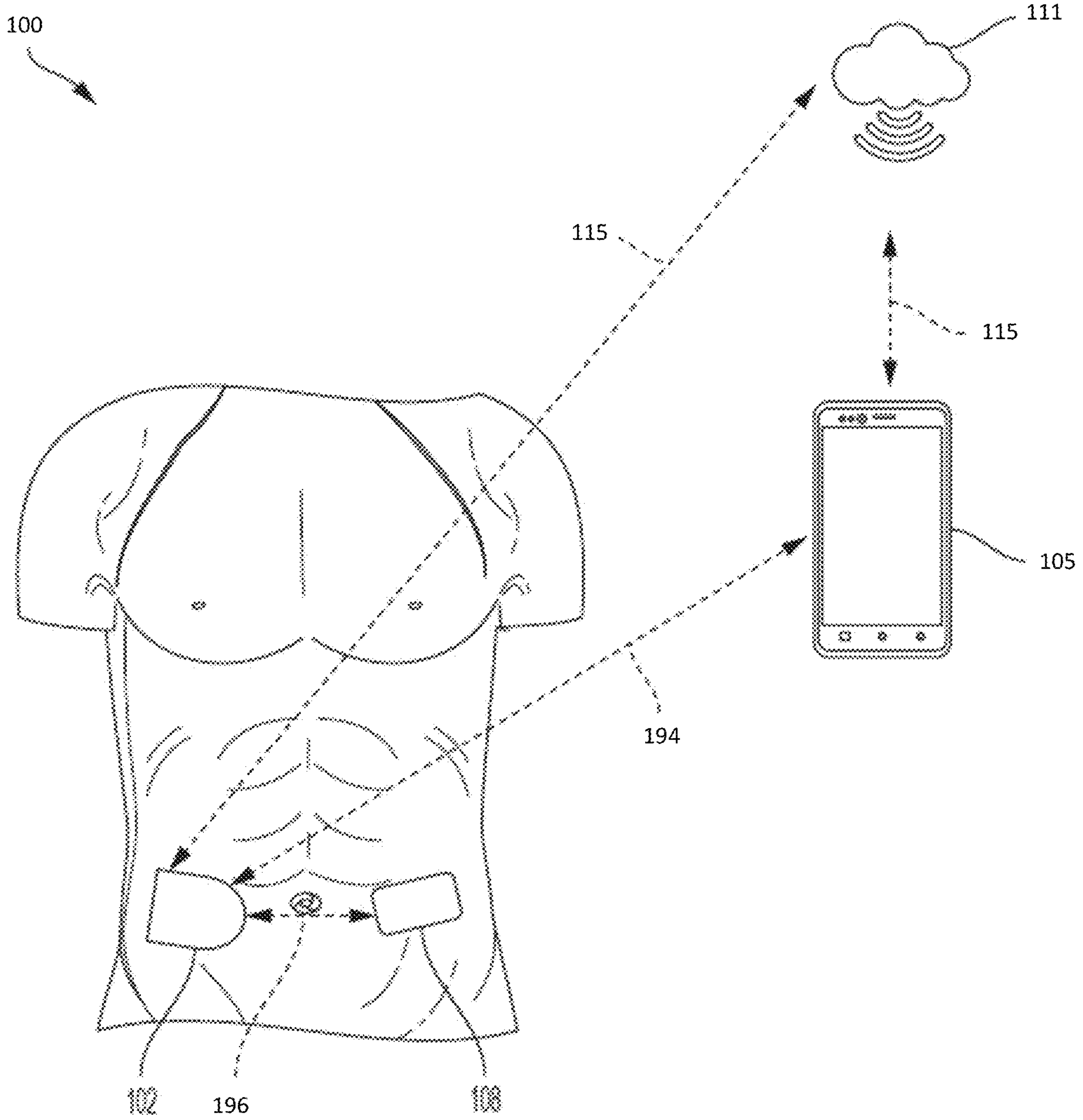
FIG. 3 shows the system components in situ on a user.

A preferred embodiment of system 100 is depicted in FIG. 3, which shows the system components in situ on the user. In this embodiment, drug delivery device 102 and analyte sensor 108 may communicate directly, and either or both may communicate directly with other devices, such as user device 105, or cloud devices or services 111. As described above, analyte sensor 108 may be incorporated into drug delivery device 102 or attached thereto in an adjacent housing.

Figure 4:
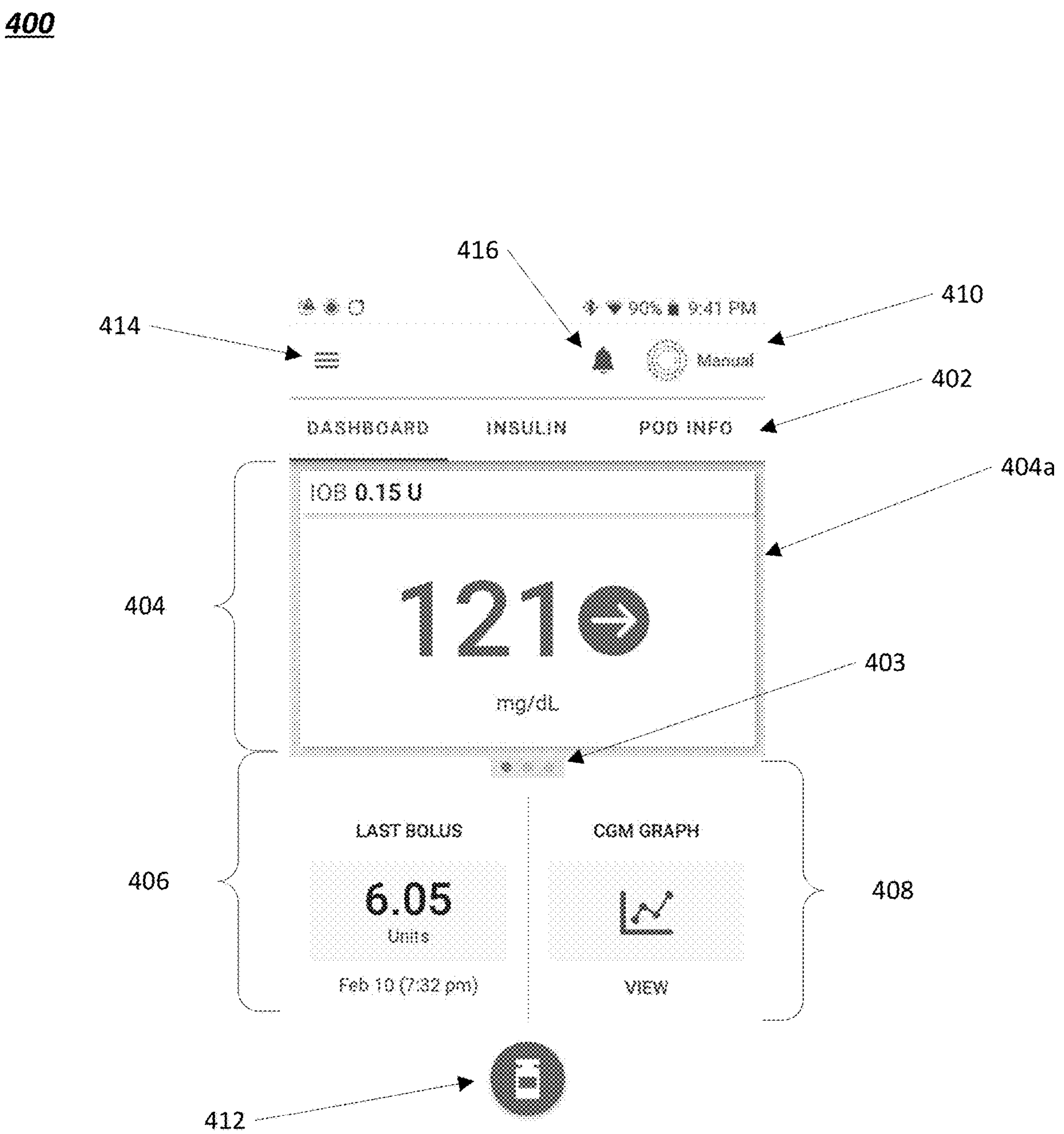
FIG. 4 shows a default home screen for the user application.

Graphical user interfaces for user app 160 will now be discussed. FIG. 4 shows a default home screen 400. The default home screen 400, or a variation of it, is displayed when the user app 160 is started.

Home Screens

The default home screen 400 includes an informational area 404 which displays one of a plurality of pages showing various information, wherein the currently displayed page depends upon a user selection of one of a plurality of tabs displayed in tab bar 402. In one embodiment of the invention, tab bar 402 has three tabs providing various page display options, a "Dashboard" tab, an "Insulin" tab and a "Pod Info" tab, the details of which will be discussed later.

In one embodiment, the "Dashboard" tab may be the default tab displayed on startup of user app 160. As shown in FIG. 4, tab bar 402 shows the "Dashboard" tab being selected, as indicated by the underlining of the "Dashboard" tab, different coloring of the word "Dashboard" and the highlighting of the leftmost dot in page indicator 403. Page indicator 103 has three dots corresponding to the "Dashboard", "Insulin", and "Pod Info" tabs in tab bar 402 but, in other embodiments, may have a different number of dots depending upon how many options are displayed in tab bar 402. The page displayed in informational area 404 may be changed by selecting one of the tabs in tab bar 402 or by swiping left or right within informational area 404. Selection of one of the tabs or swiping left or right within area 404 will change what is displayed in informational area 404 without affecting what is displayed in areas 406 or 408 of the screen. Informational area 404 is configured with a border 404*a* the color which may change depending upon the mode of operation. For example, the border may be colored light gray when the user application 160 is in manual mode, or when there is no active pod or no pod communication. When the user application is in automated mode, border 404*a* may be purple or another color when the pod is reporting operation in a fully automated state and dark gray when the pod is reporting operation in a limited automated state.

Figure 8A:
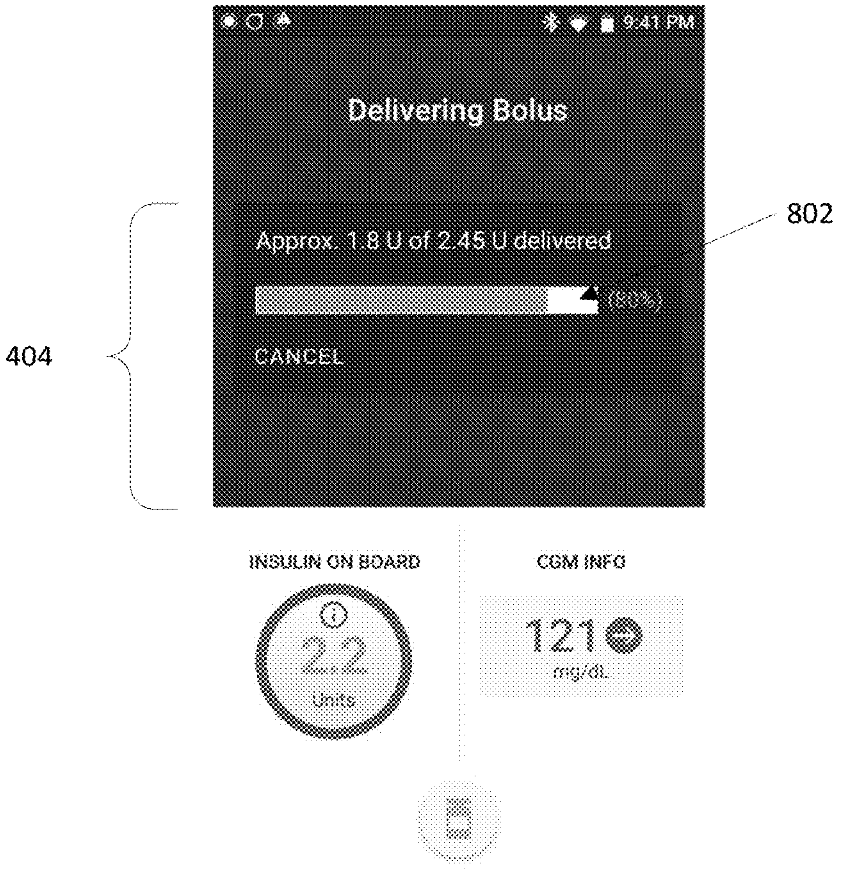
FIGS. 8(*a-b*) show examples of pages which are displayed overlaid on the main area of the home screen when the user application is performing an immediate or extended bolus delivery.
Figure 8B:
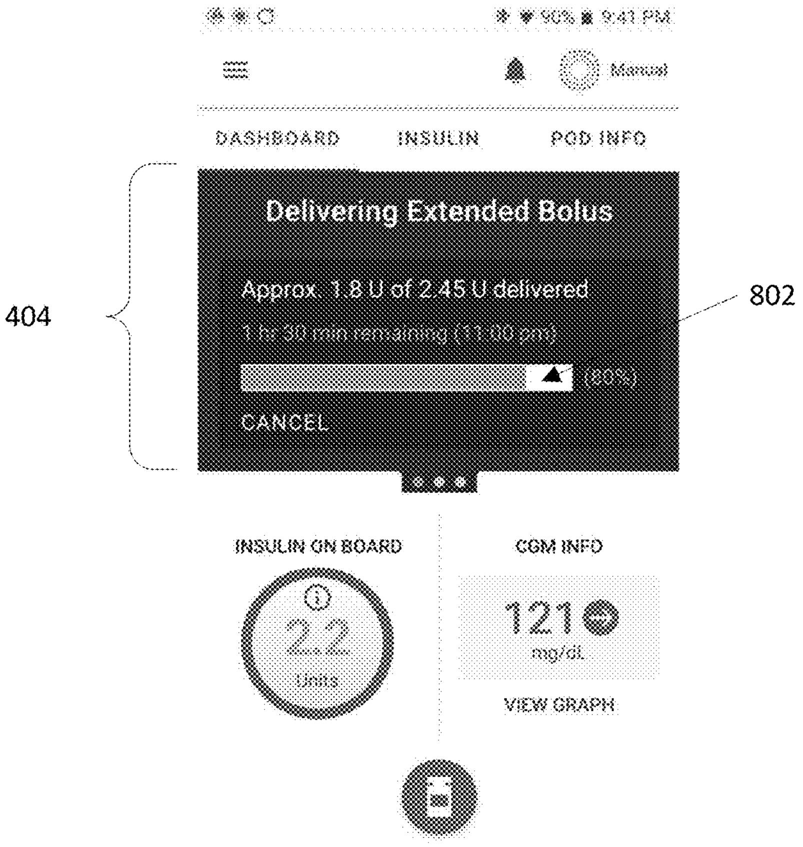

The variation of home screen 400 which appears when the user app 160 is started or when the user navigates to the home screen 400 depends on the current state of user app 160. In one embodiment, for example, if an immediate bolus is being delivered, the default home screen will appear as shown in FIG. 8*a*. If an extended bolus is being delivered, the home screen will appear as shown in FIG. 8*b*.

Under certain circumstances, upon startup, the "Pod Info" tab would be selected, and the appropriate informational page displayed in informational area 404. Examples include: no active connection with a wearable drug delivery device 102, the insulin in the reservoir of the wearable drug delivery device 102 is less than or equal to a particular amount, such as 5U, the time to pod expiration is less than or equal to a particular duration, such as six hours, the time to pod expiration is between a particular range, such as between 6 and 12 hours, and/or the user has set a pod expiration reminder. Other situations may give rise to the "Pod Info" tab being selected and other information screens being displayed.

Under certain circumstances, upon startup, the "Insulin" tab will be selected for and an appropriate informational page would be displayed in informational area 404. These include, for example, when a temporary basal program is running or when the user app 160 is running in a hypoglycemia protection mode, such as HypoProtect™ Mode. Otherwise, the default home screen 400, as shown in FIG. 4 is displayed.

Examples of the various pages which may be displayed in informational area 404 are shown in FIGS. 5-10 and are discussed in detail later.

Bolus display area 406 of default home screen 400 displays either a last bolus amount or status, and/or an insulin-on-board (JOB) state. Details of both the last bolus dose or insulin on board state will be discussed later. The information displayed in bolus display area 406 may be automatically selected depending upon the current state of the user app 160. Alternatively, the display may be changed by the user by providing a user tap within bolus display area 406. Examples of the pages displayed in bolus display area 406 are shown in FIGS. 9(*a-b*).

CGM area 408 of default home screen 400 provides an option to display information regarding the continuous glucose monitoring of the user. In certain embodiments, CGM area 408 may display, for example, a readout of the most current glucose reading or a graph of a predetermined number of the most recent glucose readings from a continuous glucose monitor. The information displayed in CGM area 408 may be automatically selected based on the current state of user app 160 or may be selected by the user by providing a finger tap within CGM area 408. Examples of the pages displayed in CGM area 408 are shown in FIGS. 10(*a-c*).

Default home screen 400 includes a mode indicator 410, which indicates the current mode of the user app 160. The various modes may be indicated by a different icon, a word indicating the mode and/or the color of mode indicator 410. In preferred embodiments of the invention, the mode indicator 410 may indicate one of four modes: (1) a "no pod communication" mode indicator, which indicates that there is no active communication between user app 160 and a wearable drug delivery device 102; this mode may be displayed only after the CGM and/or the IOB values have expired; (2) a "limited" mode indicator which displays in automated mode when the drug delivery device 102 reports that it is in limited state; (3) a "manual" mode indicator which displays when user app 160 is operating in manual mode; and (4) an "automated" mode which displays when the drug delivery device 102 reports that it is operating in the fully automated state or in a hybrid automated state.

Default home screen 400 includes a menu button 414 which, when activated by a user tap on the menu icon, displays, in one embodiment of the invention, a vertical menu overlaying the left side of the home screen 400. An example of the displayed menu 1300 is shown in FIGS. 13(*a-b*).

FIGS. 5(*a-d*) shows pages which may be displayed in informational area 404 of default home screen 400 when the "Dashboard" tab is selected. FIG. 5*a* shows a default page which includes an indicator of the insulin on board 502, the most recent reading 504 from the connected CGM 108, and an arrow 506 indicating how the readings from CGM 108 are trending. In some instances, arrow 506 may be absent, indicating that CGM 108 does not yet have enough data to identify a trend. Both the most recent CGM reading 502 and the trend arrow 506 may be displayed in various colors indicative of the value of the CGM reading in comparison to the desired values. For example, in a preferred embodiment, a blue color indicates that the CGM reading 502 is within a user-set CGM/BG goal range and user app 160 is operating in manual mode; a red color indicates that the most recent CGM reading 504 is below the user-set CGM/BG goal range (in both manual and automated modes); a yellow color indicates that the most recent CGM reading 504 is above the user set CGM/BG goal range (in both manual and automated modes); and a purple color indicates that the most recent CGM reading 504 is within the user-set CGM/BG goal range and that the user app 160 is operating in automated mode. In other embodiments, other colors may be used as indications of other states.

Figure 5A:
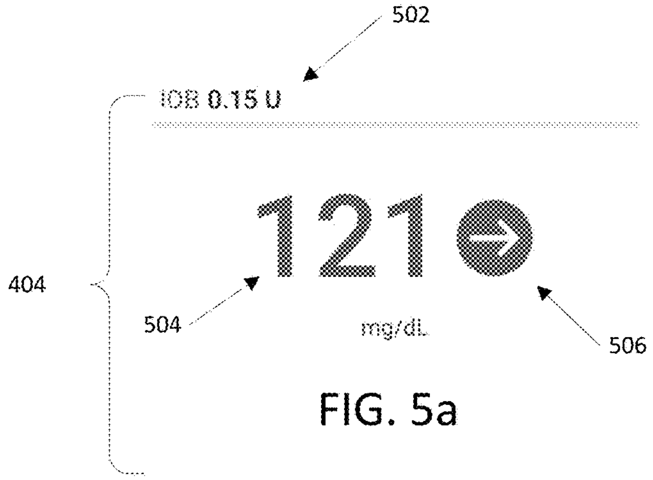
FIGS. 5(*a-d*) show examples of informational pages which are displayed in the main area of the home screen when the "Dashboard" tab has been selected.
Figure 5B:
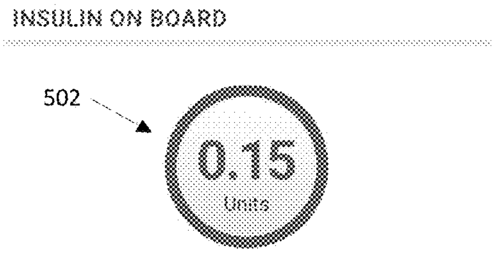
Figure 5C:
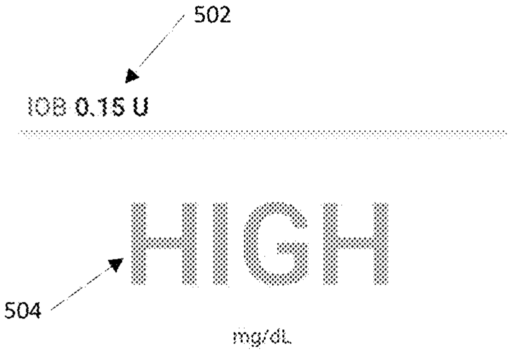
Figure 5D:
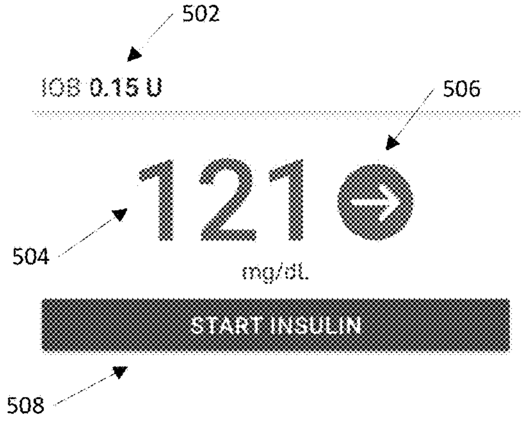

FIG. 5*b* is an example of a page displayed in informational area 404 when there is no CGM monitor 108 registered with user app 160 and when there is an active wearable drug delivery device 102. In this case, the most recent CGM reading 504 may not be available and, as such, only the insulin on board is displayed. FIG. 5*c* shows a screen which indicates that CGM 108 has returned a "HIGH" status. The high status is displayed in yellow indicating that the most recent CGM reading 504 is above the user set CGM/BG goal. Likewise, this type of page could show a "LOW" indication (not shown), which would be shown in red, indicating that the most recent CGM reading 504 is below the user-set CGM/BG goal range. FIG. 5*d* shows a page similar to the page shown in FIG. 5*a*, but with the addition of button 508 which allows user to start the delivery of a bolus dose of insulin. Other screens are also available, for example, screen showing the connection status of the CGM 108 may be displayed in informational area 404.

FIGS. 6(*a-f*) shows pages which may be displayed in informational area 404 of default home screen 400 when the "Insulin" tab is selected. FIG. 6*a* shows the default page which is displayed when a basal program is in progress. A basal program icon 602 is displayed in the upper left-hand corner of the screen. Different basal programs may have different icons. When the basal program is running, the basal program icon 602 is shown in green and, when the basal program is not running, the basal program icon 602 may be grayed out. The basal program name and status 604 is shown next to the basal program icon 602. Basal graph 606 shows a full 24-hour graph showing the total units of insulin to be delivered in a 24-hour period by the currently running basal program. The current basal rate 608 is shown in the box above basal graph 606 in accordance with the current time of day. Below the basal graph 606 is a total insulin indicator 610, which shows a total insulin to be delivered by the currently running basal program over the course of the day. Button 612, when selected by a user tap thereon, transitions the screen to the page shown in FIG. 6*b*, wherein a list of saved basal programs 614 overlays bolus display area 406 and CGM area 408 on default home screen 400. The currently running basal program 613 is shown in informational area 404. Button 616 allows the user to create a new basal program which will be saved in list 614. Screens for creating, editing and starting the basal program are shown in FIGS. 17(*a-f*).

Figure 6A:
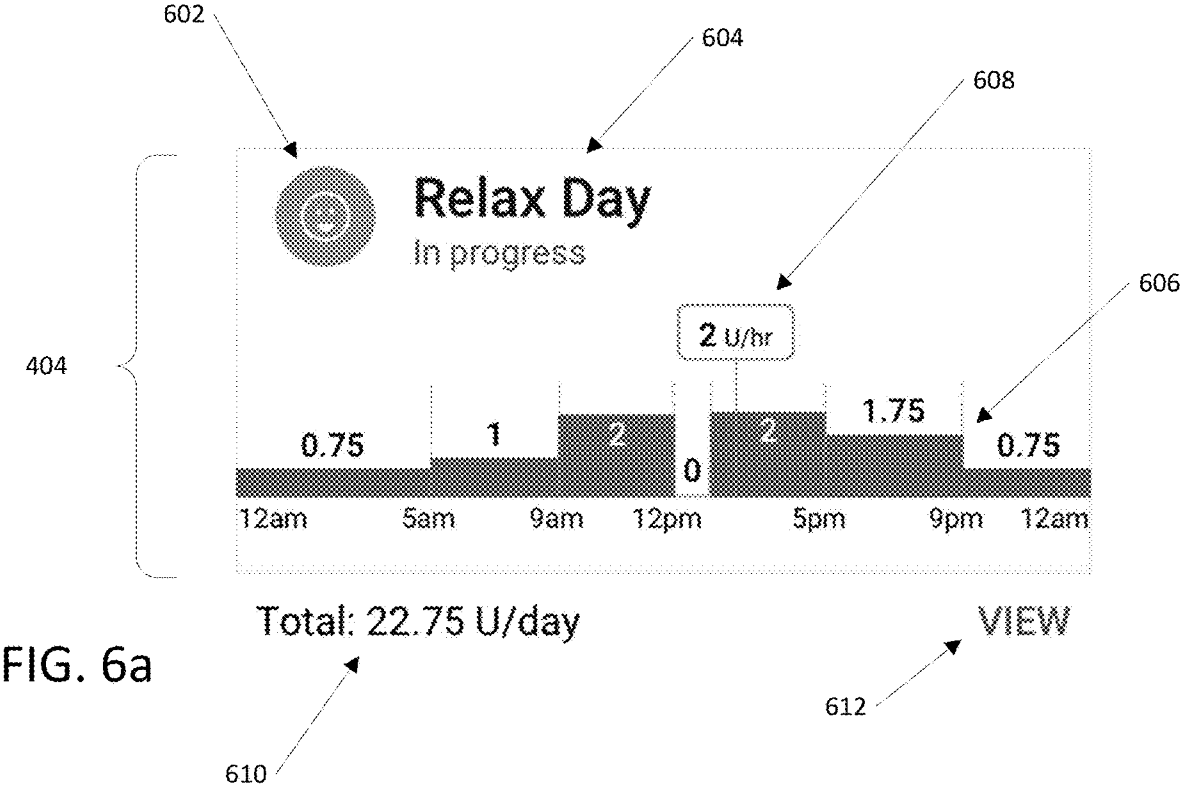
FIGS. 6(*a-f*) show examples of informational pages which are displayed in the main area of the home screen when the "Insulin" tab has been selected.
Figure 6B:
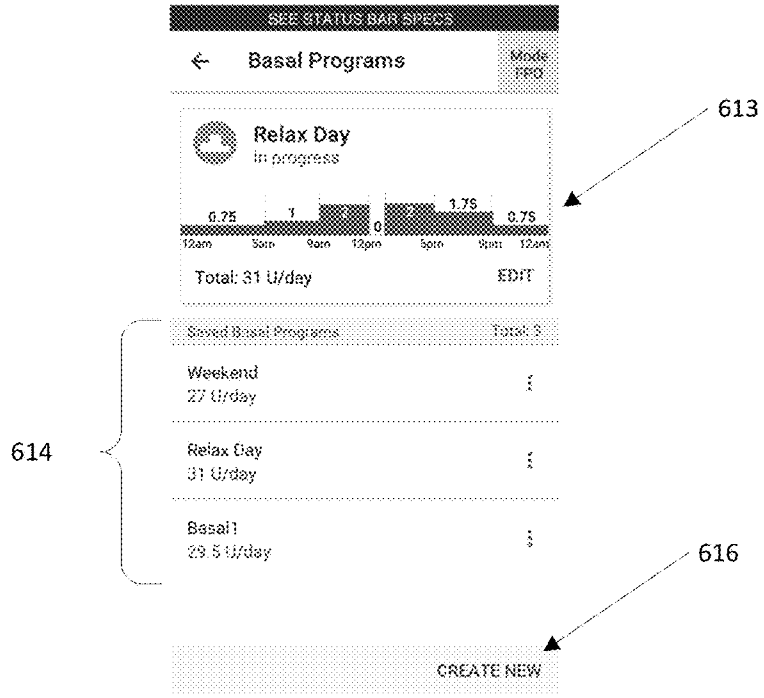
Figure 6C:
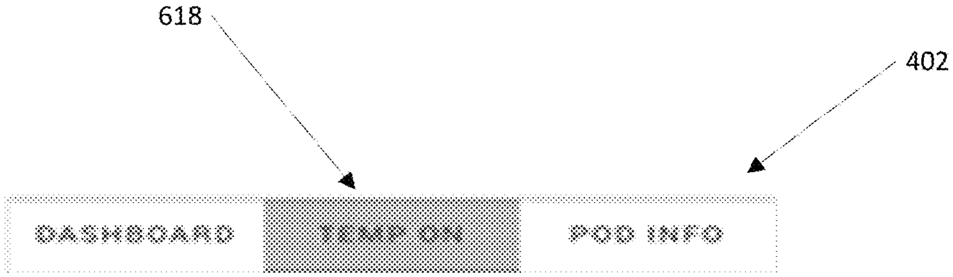
Figure 6D:
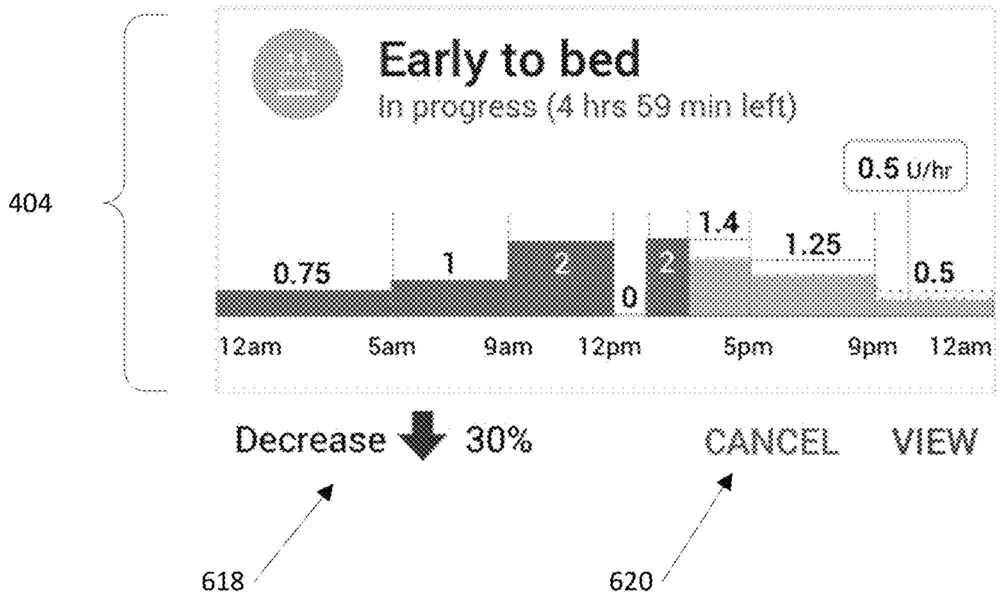
Figure 6E:
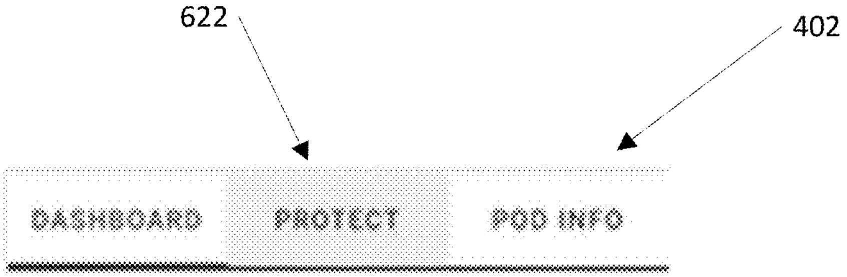

FIG. 6*d* shows the page displayed in informational area 404 when a temporary basal preset program is running. The page is identical to that for a basal program except that the total daily insulin 610 has been replaced by a change in the basal delivery 618 by the temporary basal program. In addition, this page includes a cancel button 620 which, when selected by a user, cancels the temporary basal program. When the temporary basal program is running, the "Insulin" tab in tab bar 402 changes to a "Temp On" button 618, shown in FIG. 6*c*. Once the temporary basal program is completed, the "Insulin" tab will again be displayed in tab bar 402.

Figure 6F:

FIG. 6*f* shows the page displayed in informational area 404 when a HypoProtect™ Mode has been selected by the user. HypoProtect™ Mode may be invoked by the user in the event that the user experiences a negative reaction from the insulin, the user is beginning an activity or timeframe during which the user will be more sensitive to insulin, or the user simply wishes to suspend or reduce delivery of insulin for a predetermined period of time. In one exemplary embodiment, when the HypoProtect Mode is selected, automated basal insulin delivery is reduced by 75% and the user's target blood glucose level is increased. Informational area 404 includes an icon 624 indicating that the HypoProtect™ Mode is in progress, as well as a time indicator 626 indicating the remaining time until normal operations resume. Also included is a button 628 ("Cancel") which user may select to immediately cancel HypoProtect™ Mode. When in HypoProtect™ Mode, the "Insulin" tab in tab bar 402 changes to a "Protect" button 622, shown in FIG. 6*e*. Once HypoProtect™ Mode ends, the "Insulin" tab will again be displayed in tab bar 402.

Other status pages (not shown) may also be displayed in informational area 404 when the "Insulin" tab has been selected. For example, if the "Insulin" tab is selected when user app 160 is running in automated or limited modes, a status screen will appear, similar to the HypoProtect™ Mode status page shown in FIG. 6*f*, to indicate the current mode.

Figure 7A:
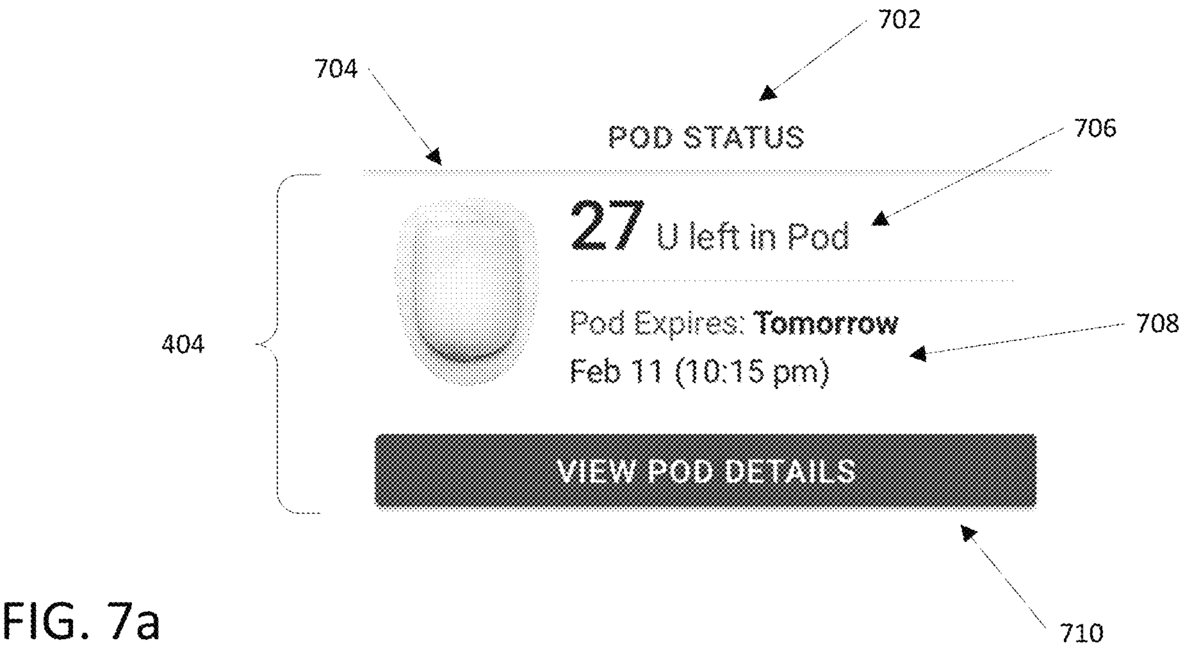
FIGS. 7(*a-b*) show examples of informational pages which are displayed in the main area of the home screen when the "Pod Info" tab has been selected.
Figure 7B:
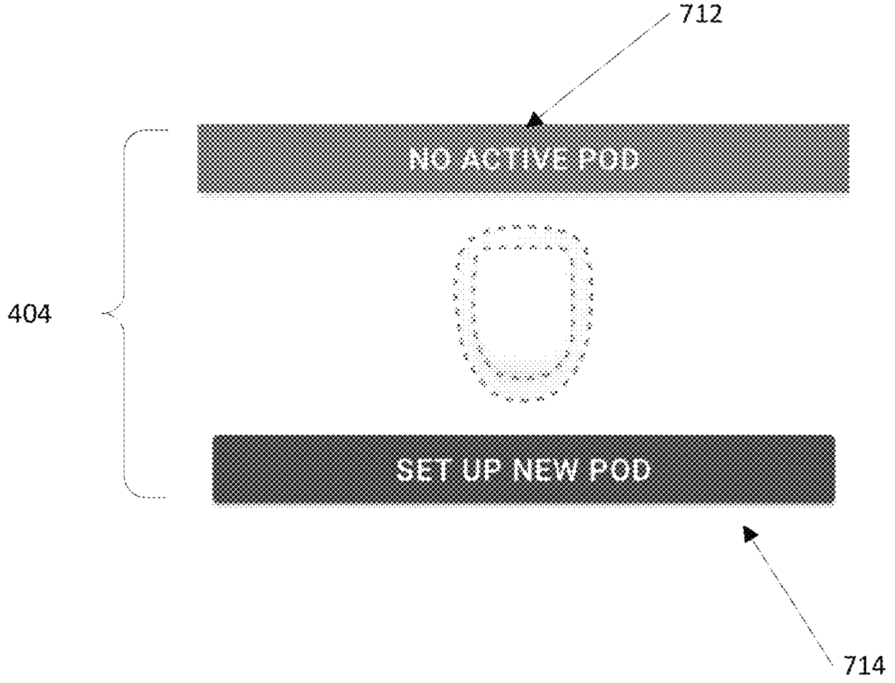

FIGS. 7(*a-b*) shows pages which may be displayed in informational area 404 of default home screen 400 when the "Pod Info" tab is selected. The default pod info page is shown in FIG. 7*a* and includes a pod status 702 shown at the top of the page. The pod status 702 may change. For example, if the drug delivery device 102 is about to expire, the pod status 702 may change to "change pod soon" or "change pod" and may be displayed in a different color, for example, yellow or red to indicate the immediacy of the status. In addition, the default pod info page includes a graphic 704 of the drug delivery device 102 in use, a quantity indicator of 706 showing the quantity of insulin (in units) left in the drug delivery device 102 and an expiration indication 708 indicating the time and date when the drug delivery device 102 will expire. The page also includes a pod details button 710 which, when selected by the user, shows more detailed information about the drug delivery device 102. FIG. 7*b* shows a page which allows users to set up a new drug delivery device 102. This page may be displayed, for example, when user app 160 has lost communication with the wearable drug delivery device 102 for a predetermined period of time. The page is provided with a "set up new pod" button 714 which allows initialization of a new wearable drug delivery device 102.

FIGS. 8(*a-b*) show default home screen 400 when a bolus is being delivered. FIG. 8*a* shows delivery of an immediate bolus and its status. During delivery of an immediate bolus, note that the menu button 414, the alarm icon 416 and the mode indicator 40 are obscured (and disabled). A progress bar 802 is included showing how much of the total bolus has been delivered (including e.g., a percentage amount), which changes as the bolus is delivered. FIG. 8*b* shows default home screen 400 during delivery of an extended bolus. Because the extended bolus extends over a longer period of time, during the extended bolus, menu button 414, alarm icon 416 and mode indicator 410 are not obscured or disabled.

Figure 9A:
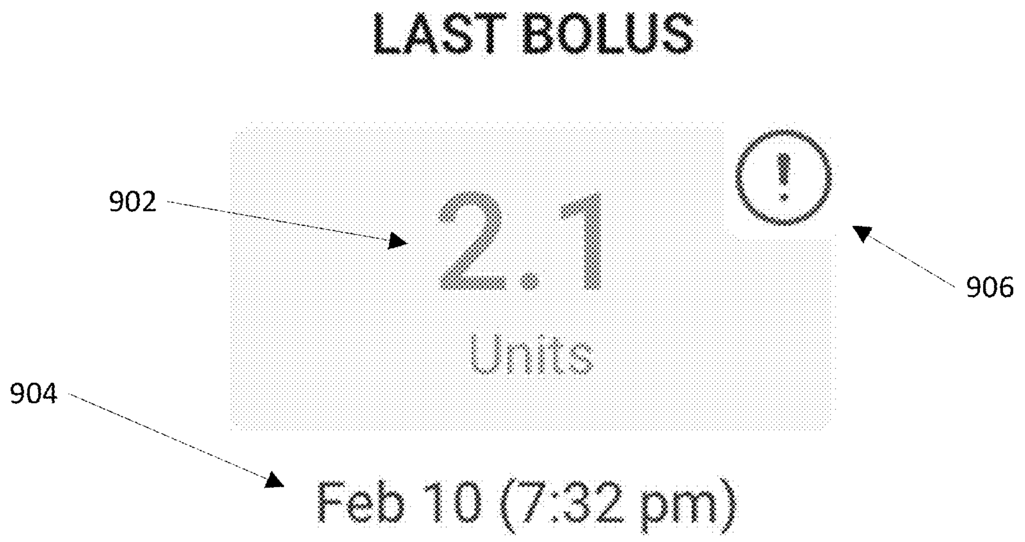
FIGS. 9(*a-b*) show examples of informational pages which are displayed in the "Last Bolus" area of the home screen.
Figure 9B:
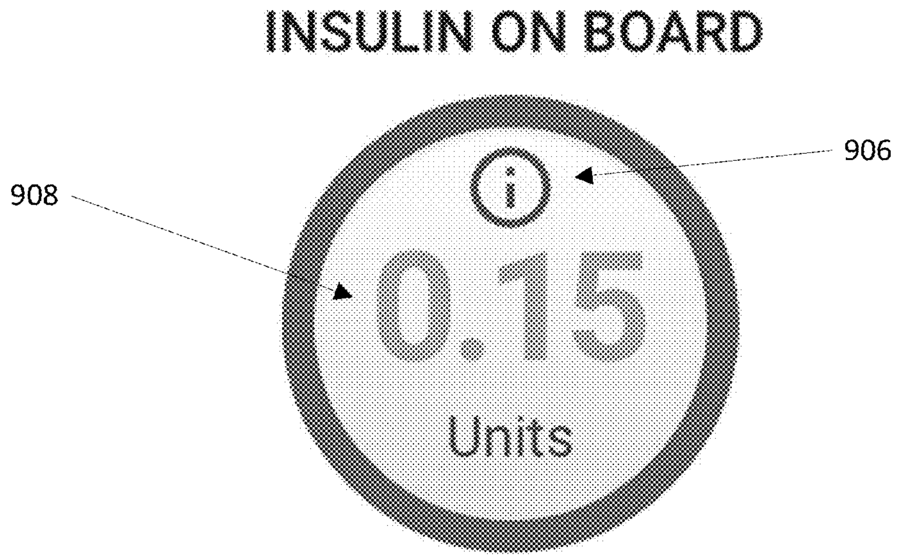

FIG. 9*a* shows a screen displayed in bolus display area 406 of default home screen 400. The screen includes an indicator of the quantity of the last bolus dose 902 of insulin which was delivered, including both immediate and extended bolus doses. During delivery of the bolus, quantity indicator 902 is grayed out, indicating that delivery of the bolus dose is not yet completed. Warning icon 906 is displayed when user app 160 assumes that delivery of the bolus has been completed, but confirmation has not yet been received from wearable medication delivery device 102. Once delivery of the bolus dose has been confirmed, warning icon 906 disappears and quantity indicator 902 is shown in a non-grayed out format (not shown). Also included is a time and date stamp 906 indicating the time and date when the bolus dose was delivered. FIG. 9*b* shows an alternate screen which may be displayed in bolus display area 406 of default home screen 400, which shows the insulin on board 908. During the delivery of the bolus dose, the insulin on board indicator 908 is constantly updated to indicate the increase in the insulin on board as the bolus is delivered. The display may also include warning icon 906, having a meaning identical to warning icon shown in FIG. 9*a*. The user may switch between the screen shown in FIG. 9*a* and screen shown in FIG. 9*b* by tapping on bolus display area 406 of default home screen 400. Note that, in the event that no bolus has been delivered, a message may appear in area 406 indicating that no boluses have been delivered.

Figure 10A:
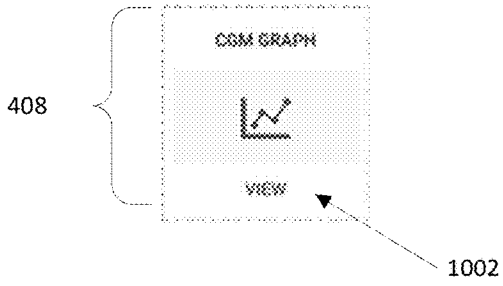
FIGS. 10(*a-c*) show examples of informational pages which are displayed in the "CGM Info" area of the home screen.
Figure 10B:
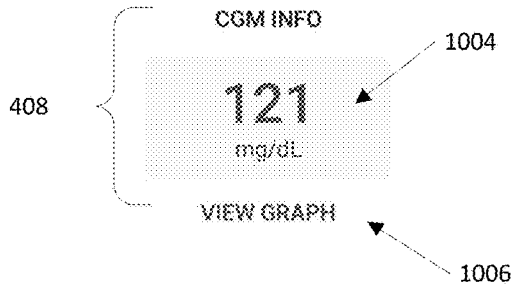

CGM area 408 in FIG. 4 allows access to information regarding the CGM. The default page for CGM area 408 is shown in FIG. 10*a*. The default page includes a graphic and a "view" button 1002 which, when selected by a user, will cause the graph shown in FIG. 10*c* to appear in informational area 404 of default use home screen 400. The page shown in FIG. 10*b* is displayed when the "Insulin" or "Pod Info" tabs have been selected from tab bar 402 or when the "Dashboard" tab has been selected are informational area 404 is obscured by the immediate or extended bolus graphics shown in FIGS. 8(*a*-*b*). The information displayed in area 1004 mimics the information displayed in the default dashboard page shown in FIG. 5*a*. The page shown in FIG. 10*b* also includes a view graph button 1006 which, when selected by the user will cause a graph shown in FIG. 10*c* to appear in area 404.

Figure 10C:
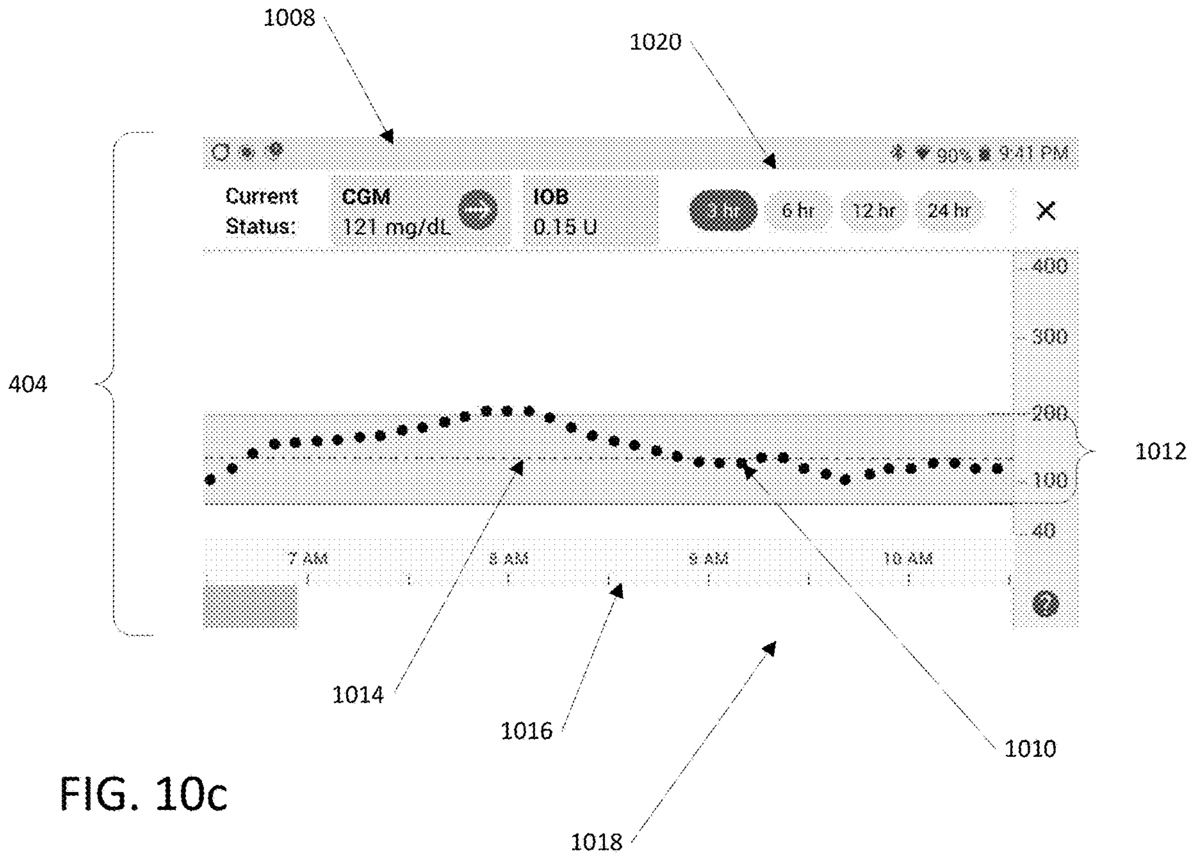

The graph shown in FIG. 10*c* appears in informational area 404 of default home screen 400. The default graph 1010 shows 3+ hours of CGM readings from the current time back. Each dot in graph 1010 represents a CGM reading received from CGM 108. Grayed out area 1012 in graph 1010 shows the goal range of the CGM/BG set by the user and dotted line 1014 is the target BG, which may also be set by the user. Timeline 1016 shows the timescale of the readings. Below timeline 1016 is an event area which shows, in one embodiment, for example: a purple background for periods of time that the user app 160 was in automated mode; a white background for periods of time that the user app 160 was in manual mode, when there was no active wearable drug delivery device 102 or when there is no communication with the wearable drug delivery device 102; a dark gray background when the user app 160 was delivering insulin in automated mode in a limited state; a blue background when a temporary basal delivery is in progress; a red line during a time that the insulin delivery was paused; an orange line during the time that the maximum allowable basal insulin was delivered; a green line when HypoProtect™ Mode was in progress; and a bolus icon (see 412 in FIG. 4) at the time when the user starts a bolus delivery of insulin. As would be realized by those of skill in the art, different colors may be used and different events may be depicted in this area.

The user can change the view of the graph to a 6 hr, 12 hr, or 24 hr timeline by selecting one of the buttons shown in area 1020. Status area 1008 shows the most recent CGM reading, with a trend arrow, as well as the current insulin on board.

Figure 12:
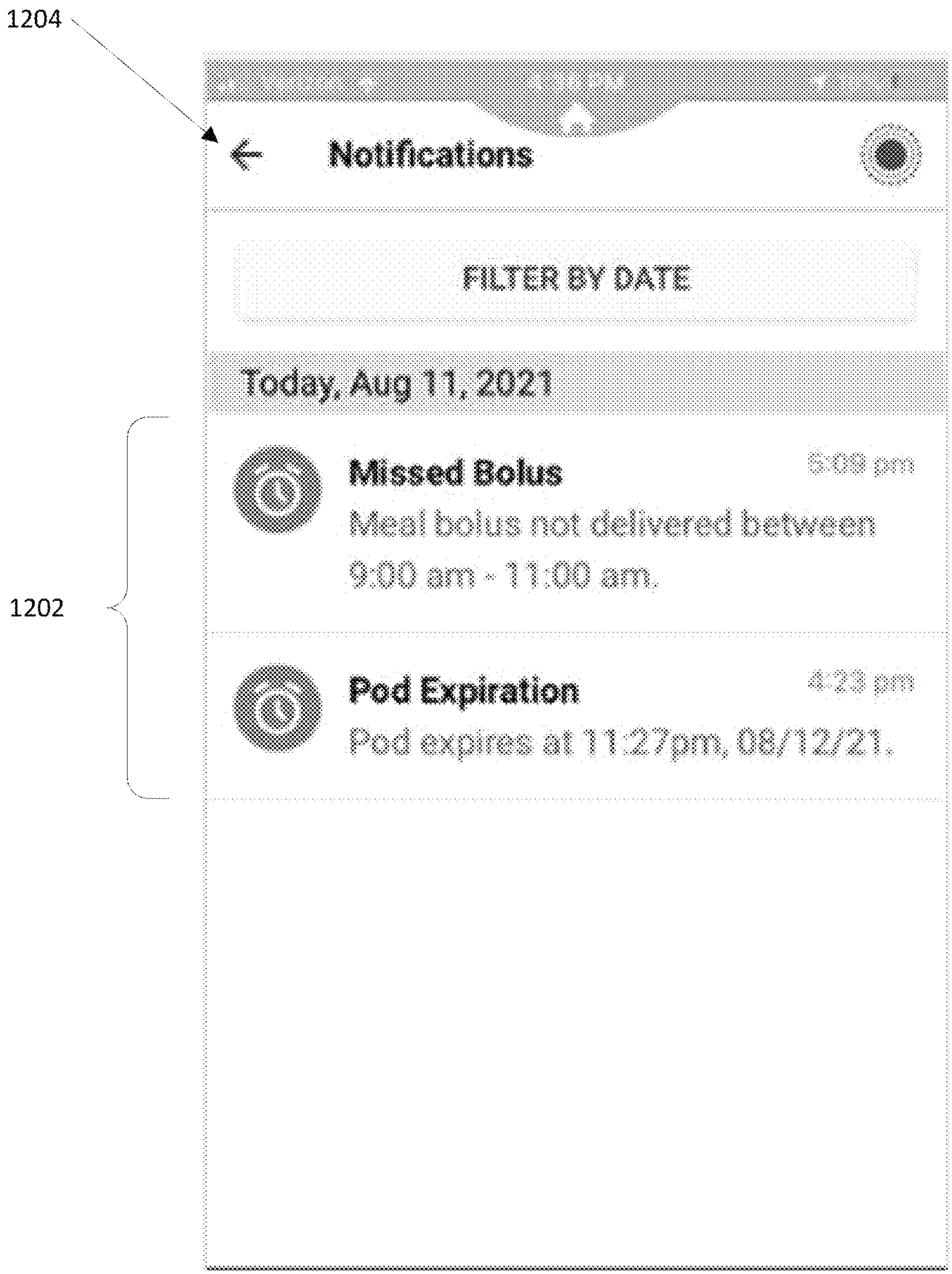
FIG. 12 is an example of a screen showing a list of notifications that is displayed when the user has selected the notification indicator from the default home screen.

Notification indicator 416 on home screen 400 indicates to the user that there is a notification available. In some embodiments, notifier indicator 416 may change its appearance, for example, by changing color, by blinking, or by changing the shape depicted. Selection of the notification indicator 416 by a user tap on the icon displays the screen shown in FIG. 12, which displays a list 1202 of notifications containing a predetermined number of previous notifications, along with the time the notification was raised. The user may return to default home screen 400 by tapping back arrow 1204.

Figure 13A:
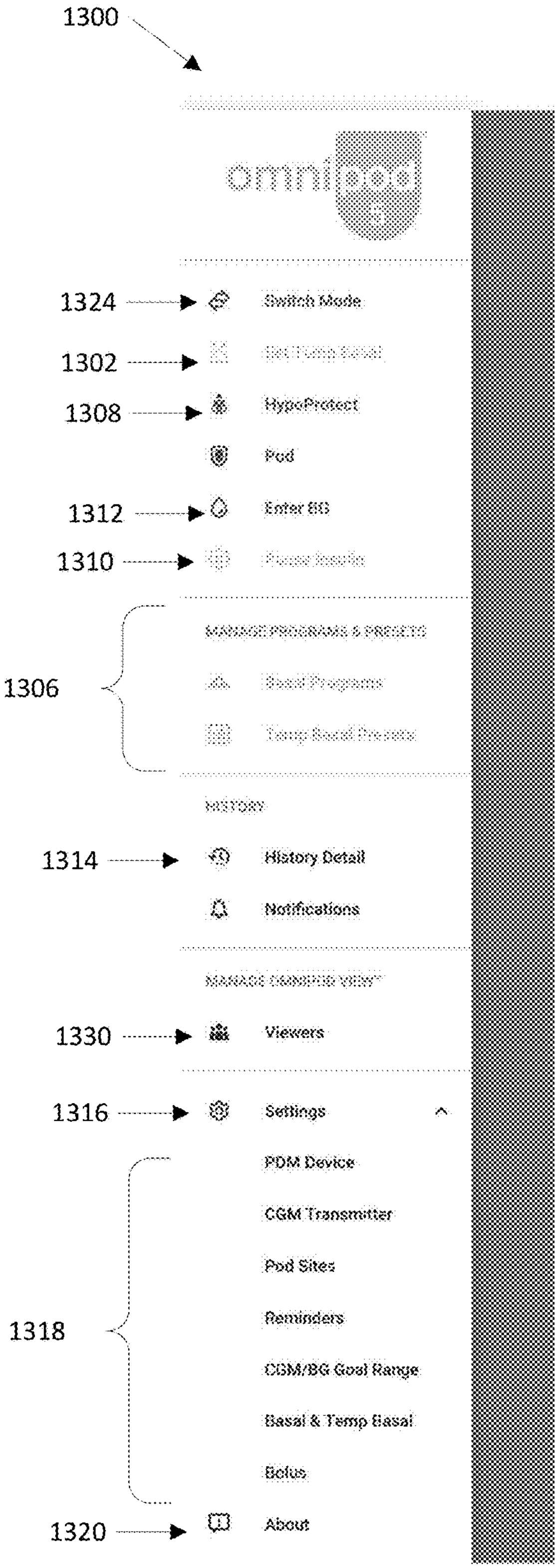
FIGS. 13(*a-b*) show examples of the main menu that appears when the menu button is selected from the home screen.
Figure 13B:
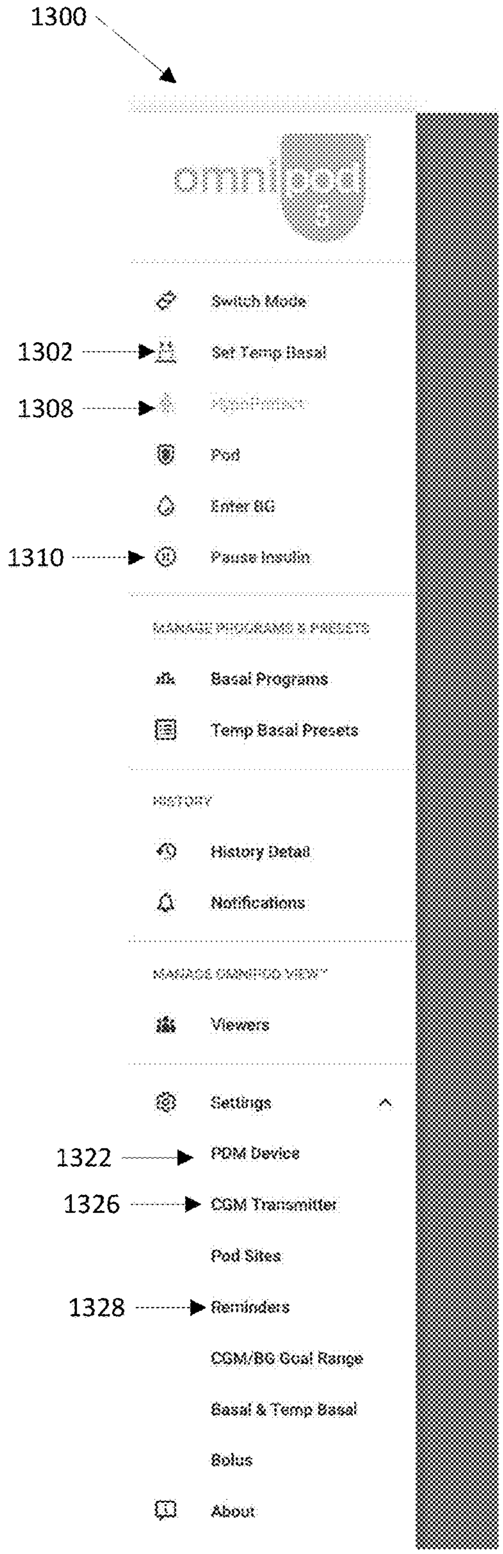

FIGS. 13(*a*-*b*) show examples variations of the menu 1300 which are displayed on a user selection of the menu button 414 on default home screen 400. Depending upon the mode of user app 160, various functions may be enabled or disabled on menu 1300. FIG. 13*a* shows menu 1300 as it is displayed when the user app 160 is in "Automated" mode. Buttons 1302 ("Set Temp Basal"), 1310 ("Pause Insulin"), and all of the buttons in section 1306 ("Manage Programs & Presets") are disabled. Button 1308 ("HypoProtect™ Mode") is also disabled if HypoProtect™ Mode is running. FIG. 13*b* shows menu 1300 as it is displayed when the user app 160 is in "Manual" mode. In this mode, button 1308 ("HypoProtect™ Mode") is disabled. Button 1602 ("Set Temp Basal") is enabled unless a temporary basal program is in progress, insulin delivery is paused, or there is no active wearable drug delivery device 102. Button 1310 ("Pause Insulin") is disabled if there is no active wearable drug delivery device 102. When button 1302 is selected and insulin delivery is paused, button 1310 is replaced with a "Start Insulin" button. The functions of the buttons in menu 1300 will be described later herein.

Figure 14A:
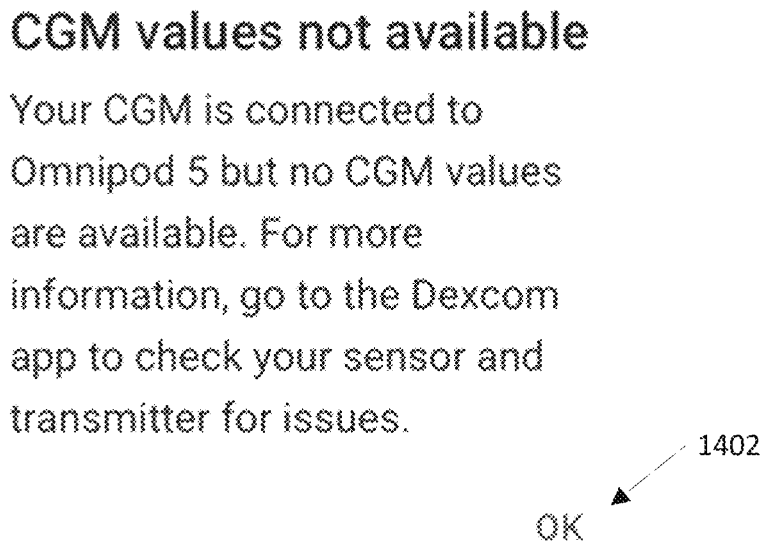
FIGS. 14(*a-b*) show examples of modal messages for providing information to the user regarding special situations or error conditions.
Figure 14B:
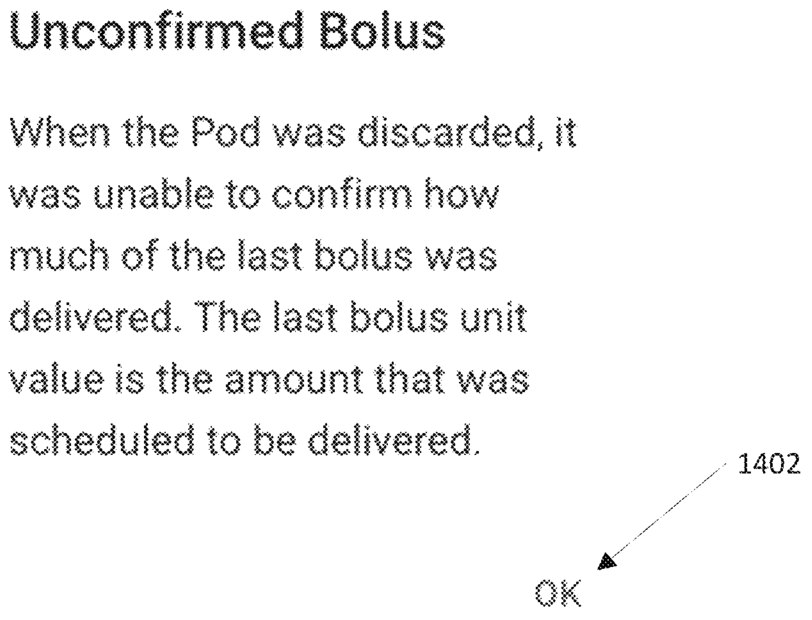

Any unusual situation or error condition that arises resulting from the operation of the user app 160, the wearable drug delivery device 102, or CGM 108 may cause the display of a modal message which is displayed overlaid on the home screen 400. Examples of modal messages are shown in FIGS. 14(*a*-*b*). Each modal message may be provided with an "OK" button 1402 which, when selected by the user, dismisses the modal message and returns to a display of home screen 400.

Bolus Screens

Bolus Button 412 on home screen 400, when selected by the user, replaces the default home screen 400 with a bolus calculator shown in FIGS. 11(*a*-*f*). Bolus button 412 may appear in different colors. For example, bolus button 412 may appear in gray, indicating that the button is disabled, when an immediate bolus delivery is in progress or when insulin delivery is paused. Bolus button 412 may appear in blue when user app 160 is in manual mode or purple when the user app 160 is in automated mode.

Figure 11B:
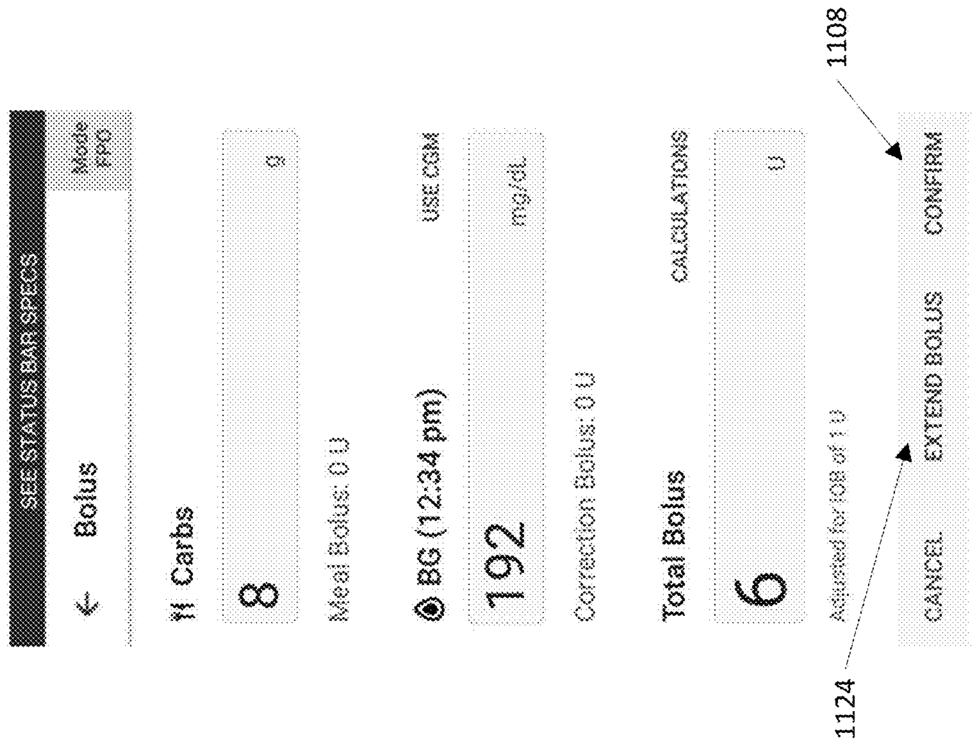
FIGS. 11(*a-f*) show examples of screens providing a bolus calculator that is displayed when the bolus button on the default home screen is selected, as well as screens allowing the user to specify an extended bolus delivery.
Figure 11A:
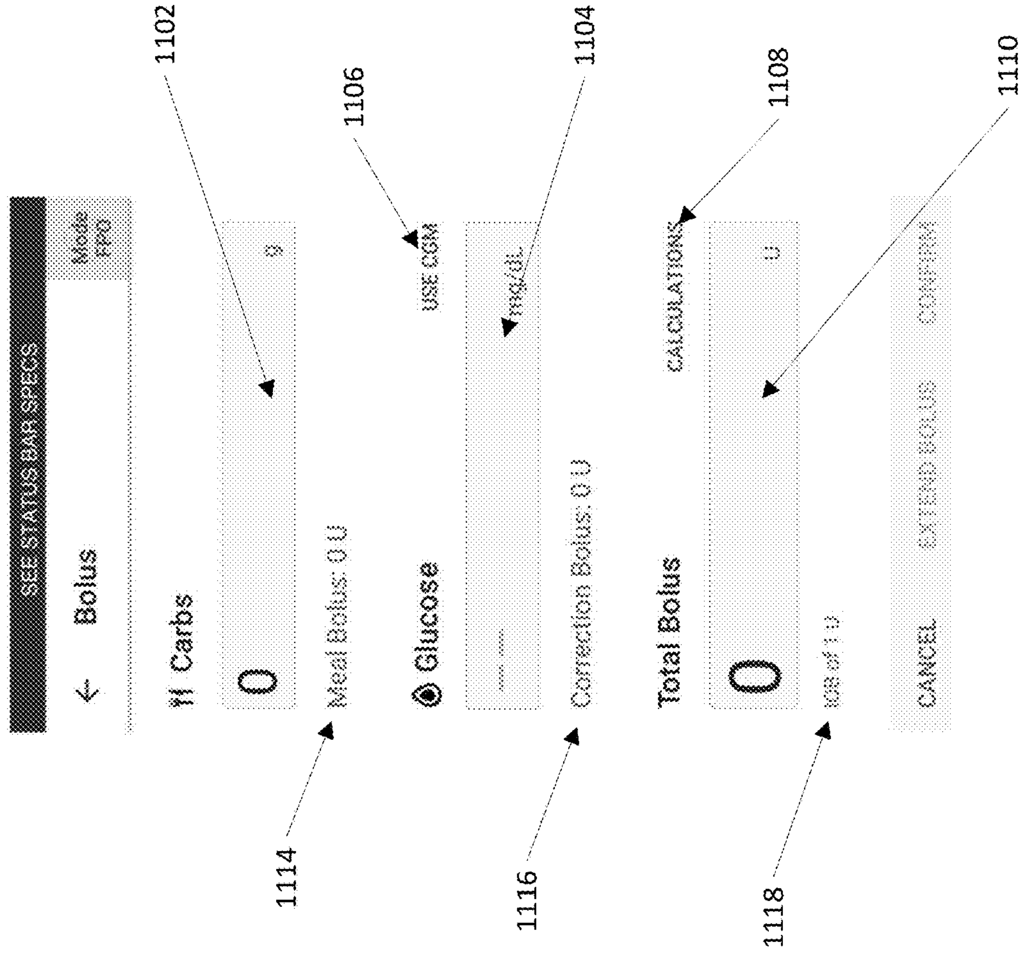

The bolus calculator is shown in FIG. 11*a*. The screen comprises field 1102 where the user may enter the total carbs ingested during a meal. Selecting field 1102 will cause a modal keyboard to appear overlaid in the screen where the user can enter the quantity of carbs. Upon exiting the modal keyboard, the entered quantity transferred to field 1102. A quantity of insulin for the bolus based on the quantity of carbs ingested during the meal is displayed as "Meal Bolus" 1114.

A corrective bolus may be required based on the user's current blood glucose readings. Field 1104 allows the entry of the current blood glucose reading. Selecting field 1104 will cause modal keyboard to appear to enable user to manually enter the current blood glucose reading. Alternatively, by pressing button 1106, the most recent reading from the CGM 108 is used and entered in field 1104. The corrective bolus is displayed as "Correction Bolus" at 1116. Note that the correction bolus may be a positive or negative number.

The current insulin on board is displayed as "JOB" at 1118. The total bolus to be delivered, displayed in field 1110, is a sum of the meal bolus and the correction bolus adjusted for the current quantity of insulin on board. Once the total bolus has been calculated, it appears in field 1120.

Figure 11C:
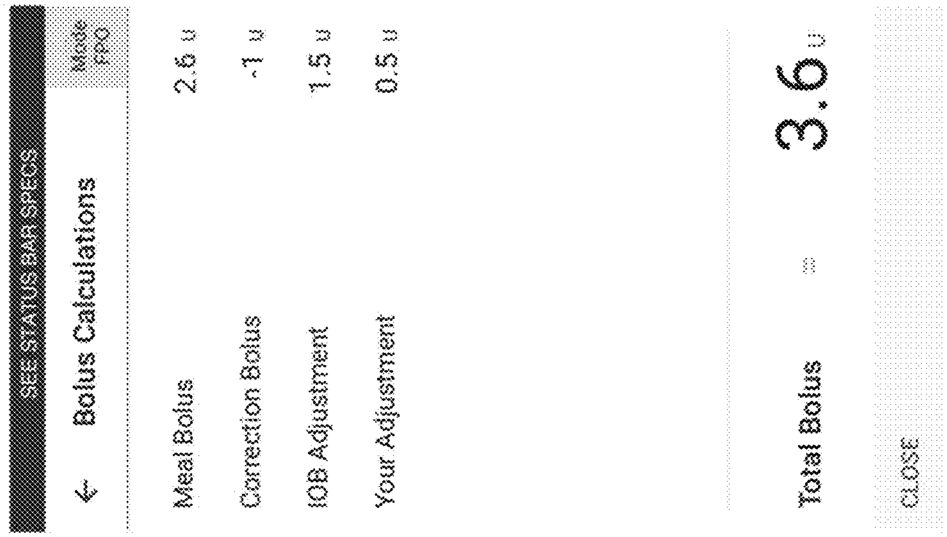
Figure 11D:
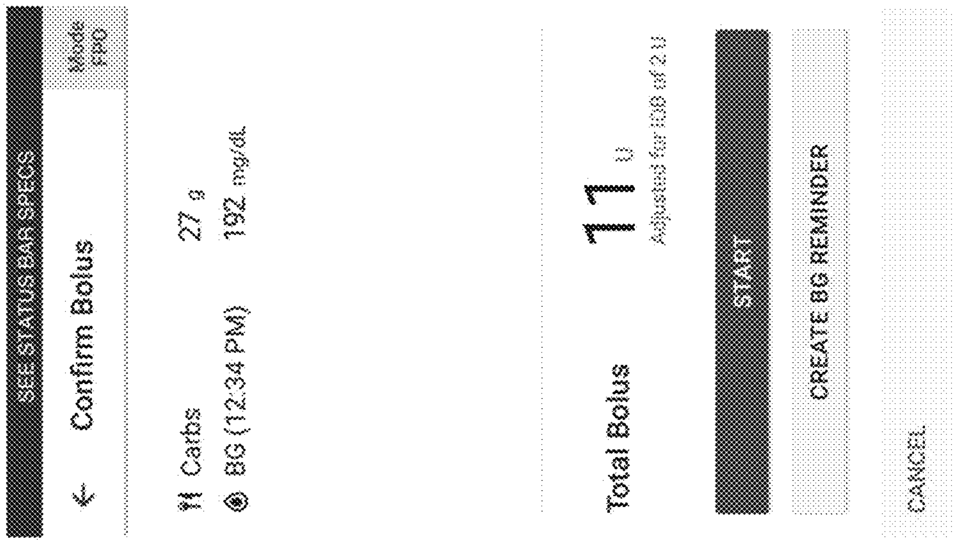
Figure 11F:
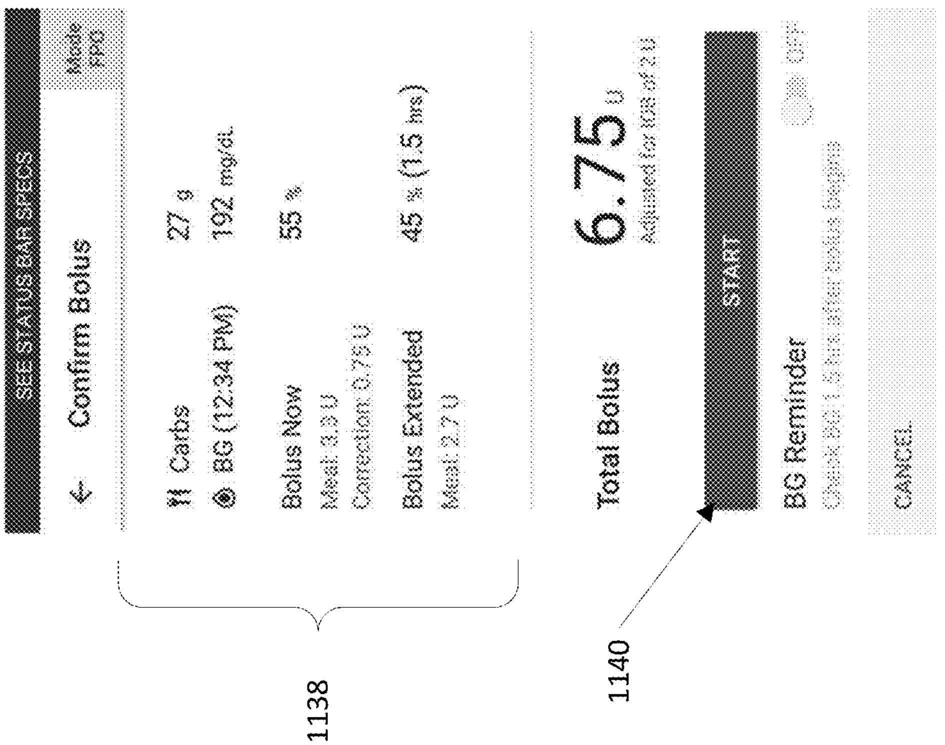

On a user selection of button 1108 ("Calculations"), the screen shown in FIG. 11*c* is displayed showing the individual components of the total bolus, including a meal bolus amount, a correction bolus amount, an IOB adjustment amount, and/or an amount entered by the user to increase or decrease the total bolus amount. FIG. 11*b* shows the completed bolus calculation. In some embodiments, field 1104 may show not only the most recent CGM reading but may also show a trend arrow (not shown) indicating the trend of the user's blood glucose readings. In the event that the trend arrow is shown, the "calculations" screen may also provide a further adjustment to compensate for the trend. On a user selection button 1122 ("Confirm") on FIG. 11*b*, the screen shown in FIG. 11*d* is displayed. From this screen, the user may press button 1126 ("Start") to start delivery of the bolus.

Figure 11E:
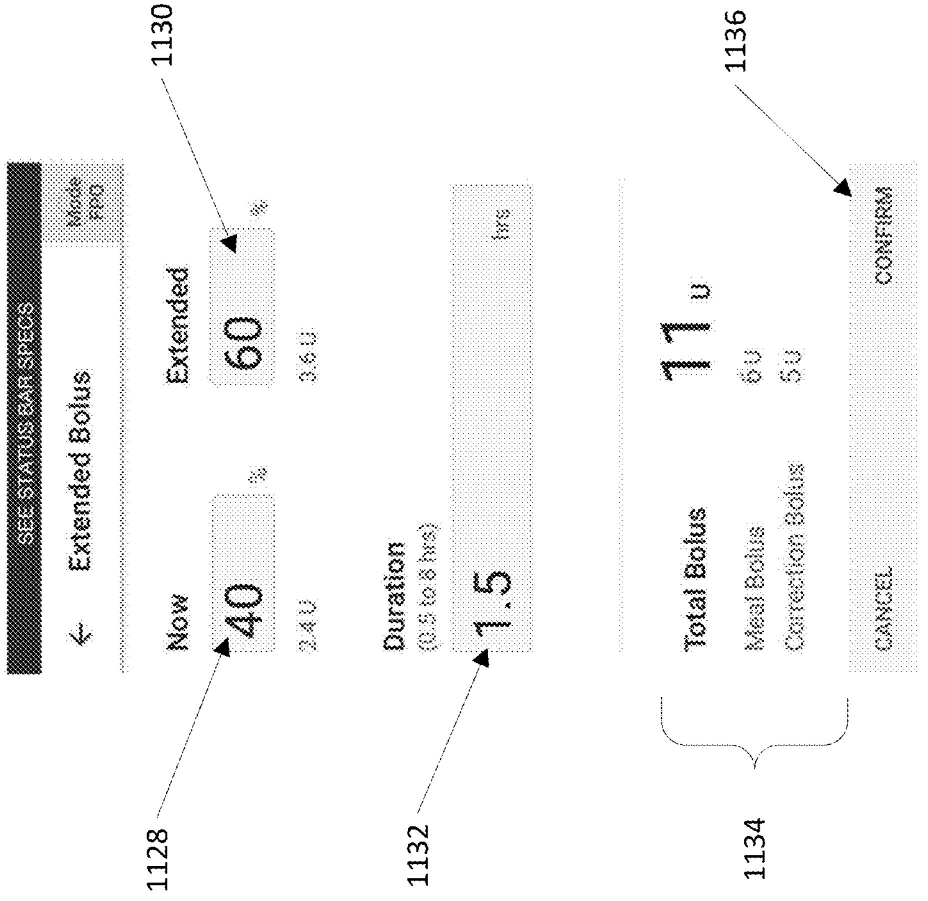

The user may wish to specify the delivery of the bolus as an extended bolus. On a user selection of button 1124 ("Extend Bolus") in FIG. 11*b*, the screen shown in FIG. 11*e* is displayed, which allows the user to enter a percentage of the bolus to be delivered immediately and a percentage of the bolus to be delivered over an extended period of time. The user may either fill in field 1128 ("Now") or field 1130 ("Extended"). By selecting either of either of the fields 1128 or 1130 a modal menu will appear having menu items for various percentages. Upon a user selection of one of the percentages, the selected percentage is transferred to the field currently having the focus (i.e., field 1128 or 1130). Whichever field has been filled by the user, the other field will be automatically filled by user app 160 by subtracting from 100%. In field 1132 ("Duration") the user is able to specify the time period over which the extended portion of the bolus will be delivered. Selection of field 1132 will cause a modal menu to appear which contains selections for various time intervals. Once the user has selected the time interval value in the modal menu, the time interval will be transferred to field 1132. A summary of the bolus appears in area 1134 of the screen. Upon a user selection of button 1136 ("Confirm"), the screen shown in FIG. 11*f* will be displayed, showing a summary of the bolus 1138, including the percentages to be delivered immediately and over an extended period of time. A user selection of button 1140 ("Start") will cause the delivery of the bolus to be started.

Pod-Related Screens

This section relates to all screens dealing with the operation, initialization, and status of the wearable drug delivery device 102 (i.e., the "Pod"). Screens related to the pod will typically replace home screen 400.

Figure 15:
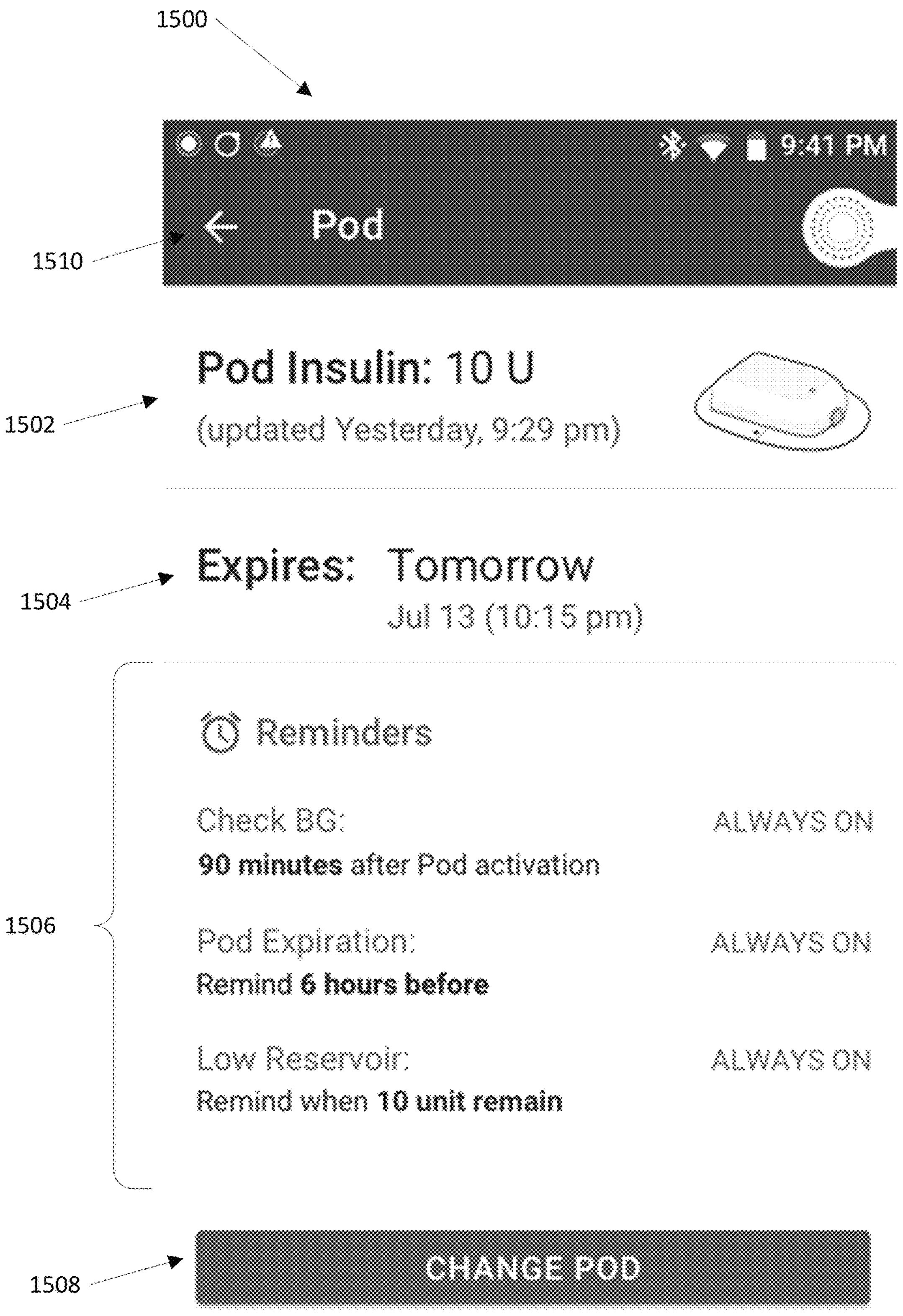
FIG. 15 shows an example of a screen showing detailed information regarding the wearable drug delivery device.

FIG. 15 shows an informational screen 1500 providing details about the current state of the pod. The screen 1500 may be reached after selecting the "Pod Info" tab from home screen 500, and then selecting the button 1010 ("View Pod Details") from the informational page shown in FIG. 7*a*. Section 1502 of the screen shows the remaining insulin in the wearable drug delivery device 102. This information is communicated wirelessly from the wearable drug delivery device 102 to the user app 160. In certain embodiments, if the remaining insulin in wearable drug delivery device 102 falls below a predetermined threshold, the display will read "LOW" instead of showing the actual quantity. Section 1504 shows the time and date when the drug delivery device 102 currently in use will expire. In one embodiment, if the drug delivery device 102 reaches 72 hours from the time it was activated, the display will read "EXPIRED" instead of showing a time and date for the expiration of the drug delivery device 102. Screen 1500 may include a button 1508 allowing the user to change the drug delivery device 102. This button may be disabled, for example, if the user has just recently changed the drug delivery device 102. A back arrow button 1510, when selected by the user, will navigate the user back to home screen 400.

Figure 16A:
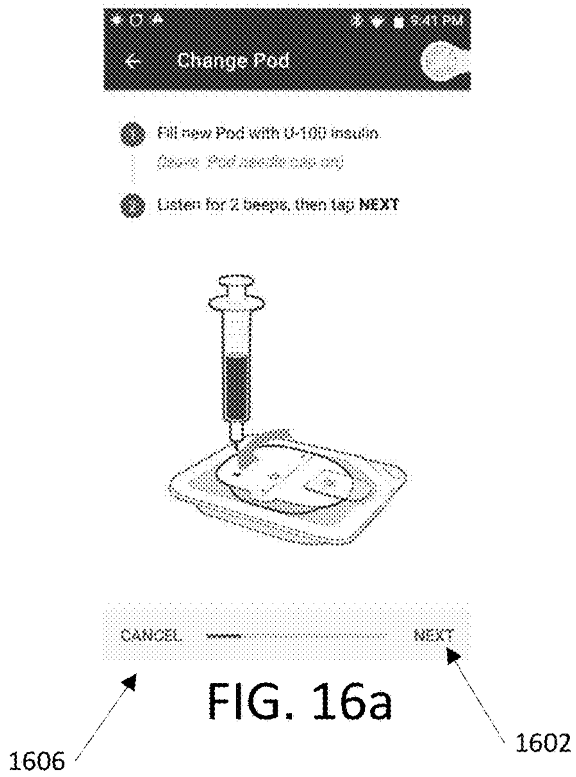
FIGS. 16(*a-d*) show examples of instructional screens which provide step-by-step instructions for the user to initialize a new drug delivery device and place the drug delivery device on the user's body.
Figure 16B:
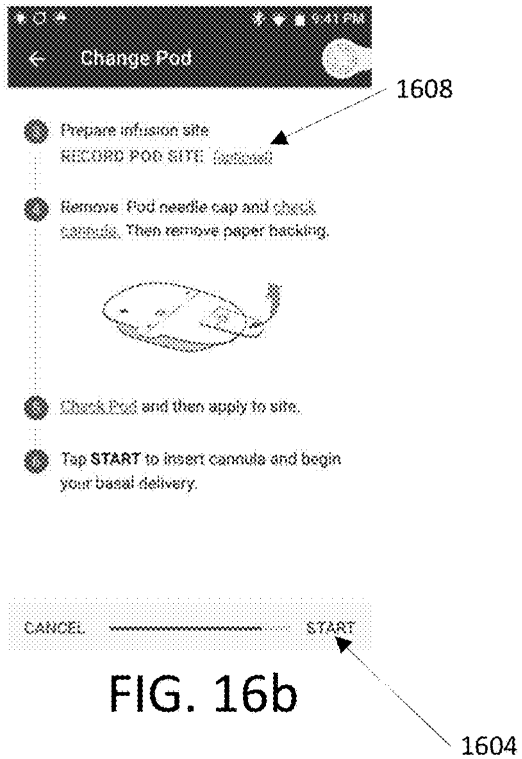
Figure 16C:
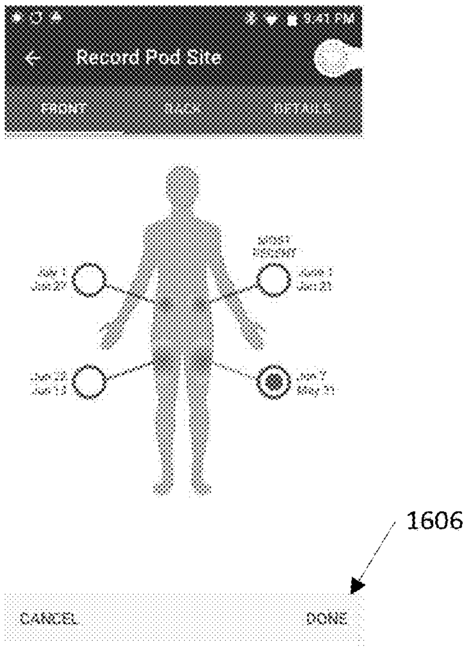
Figure 16D:
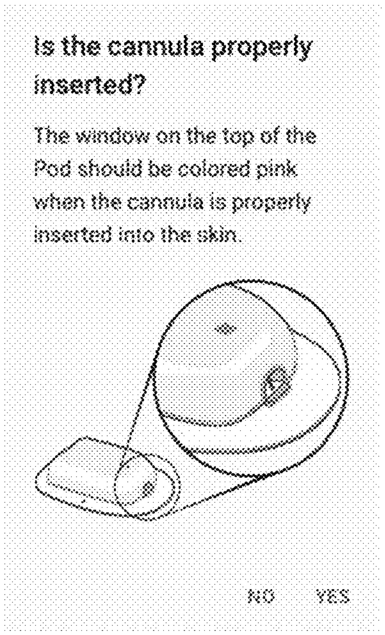

The user may be presented with a series of screens providing step-by-step instructions for changing the drug delivery device 102. These screens may be displayed after user has selected button 1508 in FIG. 14. FIGS. 16(*a-d*) show examples of four of the screens in the series. Each screen is provided with a button (1602) which moves the user to the next instructional screen in the sequence. The user may cancel the operation at any time by pressing the cancel button 1606 on any instructional page. Once the drug delivery device 102 has been properly set up and positioned, the user can start operation of the drug delivery device 102 by selecting button 1604 in FIG. 16*b*. During the setup process, the user may be presented with one or more modal screens, an example of which is shown in FIG. 16*d*, which shows a screen asking the user to verify that the cannula in the drug delivery device 102 has been inserted correctly, as indicated by a pink status light showing on the housing of the body of drug delivery device 102. The user may respond by pressing the "Yes" or "No" button on the screen. Several instructional pages may be provided with hyperlinks, for example, hyperlink 1608 shown in FIG. 16*b* that will take the user to other instructional pages. Pressing hyperlink 1608 in FIG. 16*b* will take the user to the screen in FIG. 16*c*, where the user may record the location on the body of the positioning of the drug delivery device 102. This page may also display previous locations and dates of different spots wherein the drug delivery device 102 was mounted such that the user may select a new location each time a new drug delivery device 102 is activated. Other pages (not shown) may also be reached via hyperlinks on the instructional pages.

Basal Program Screens

This section relates to screens that allow users to view, select, edit and create basal programs for execution by user app 160. FIG. 17*a* shows the screen of FIG. 6*b* having a modal menu 1704 overlaid thereon. The modal menu 1704 for any of the basal programs and list 614 can be invoked by touching the 3 dot menu invocation control 1703 located beside each basal program in list 914. Modal menu 1704 contains menu items allowing the user to start, edit or delete the currently selected basal program. Basal program can be created by the user by selecting the "Create New" button 616.

Figure 17B:
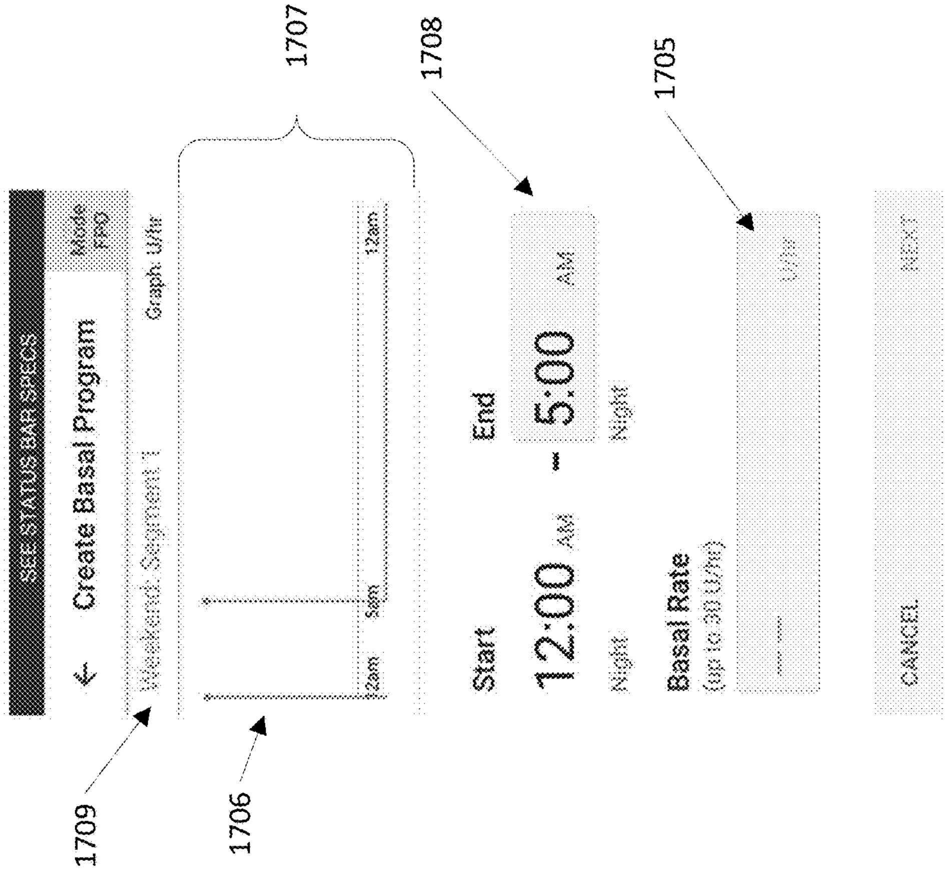
FIGS. 17(*a-f*) show examples of screens that allow the user to view, create, edit and start a basal program.
Figure 17A:
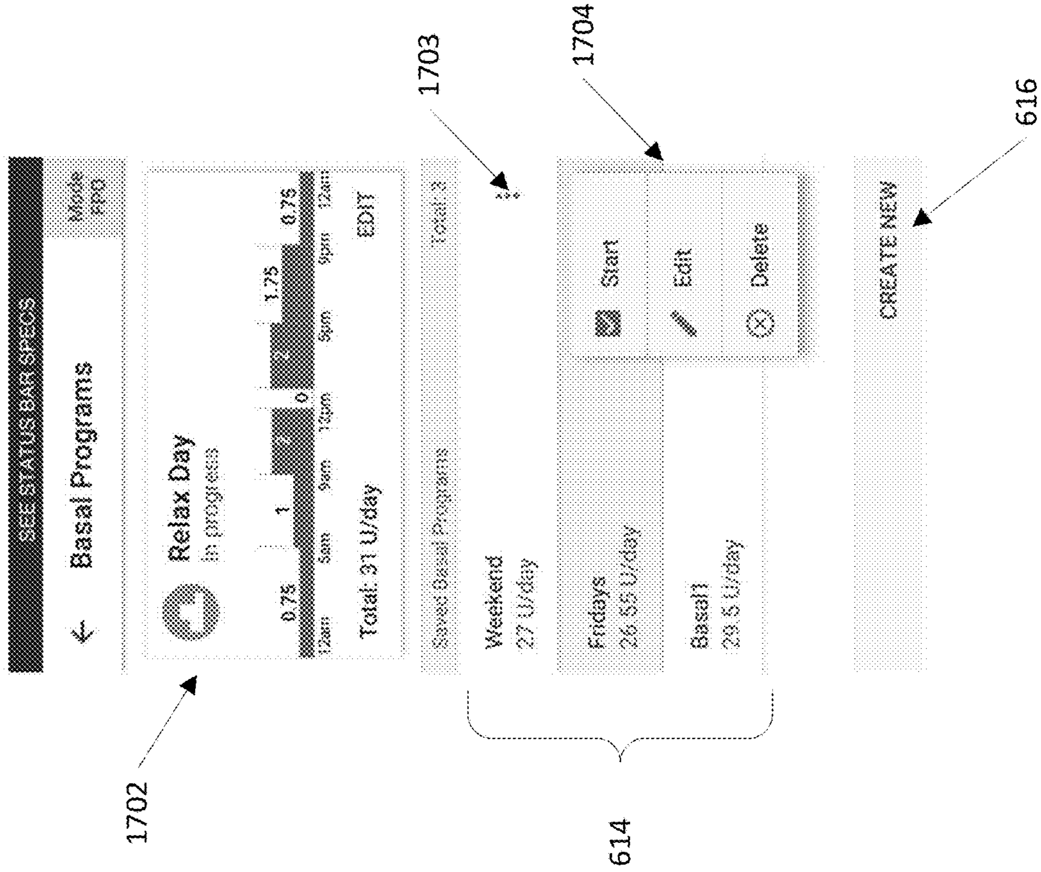

FIG. 17*b* shows a screen use during the creation of the basal program. The user may provide a name 1709 for the program which is displayed near the top of the screen. For each segment of the basal program, the user must specify the start time of the segment, the end time or duration of the segment, and the basal rate to be delivered during the specified segment. Next to the name 1709 is an indicator of the current segment being specified. Once the user has specified the start and end times of the segment in fields 1708, vertical lines 1706 will appear in area 1707 of the screen to indicate the start and end times of the segment. In some embodiments, the start time may be a prefilled field, with the user only specifying the end time. In some embodiments, the user may either type in the end time manually in field 1708 or may select the end time from a modal menu (not shown) or may select a duration from a modal menu (not shown). Once the user selects the end time for the segment, the end time will be used as the start time for the next segment and will be used to pre-fill the start time field.

Figure 17D:
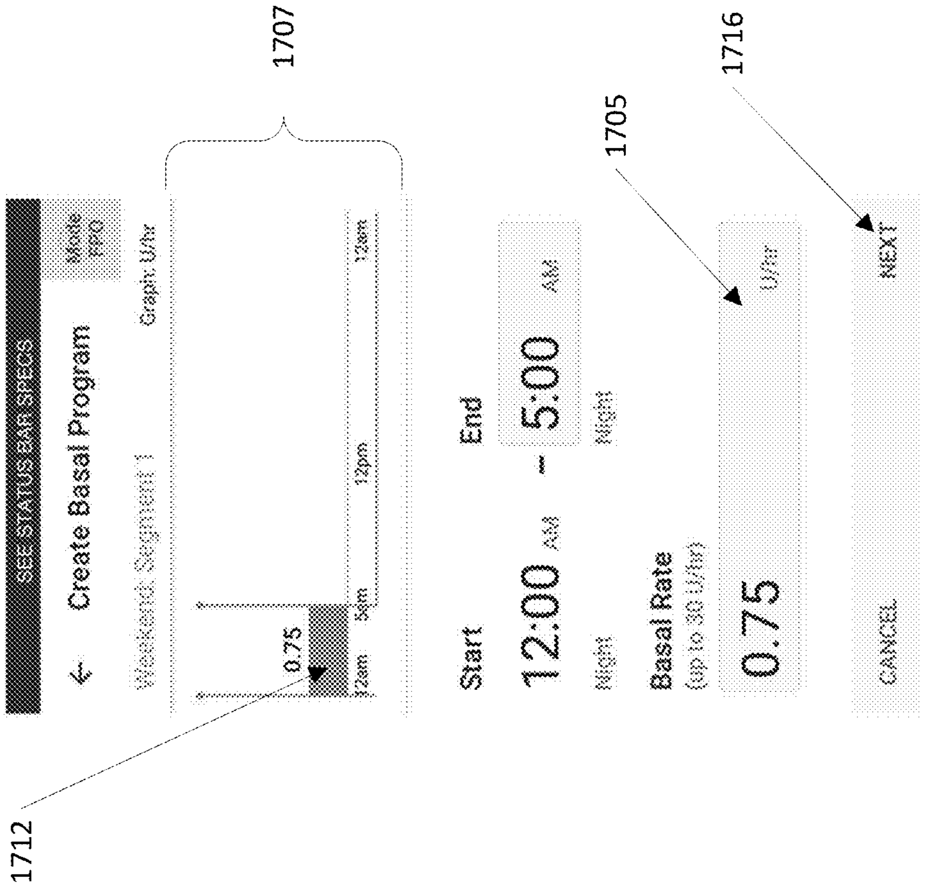
Figure 17C:
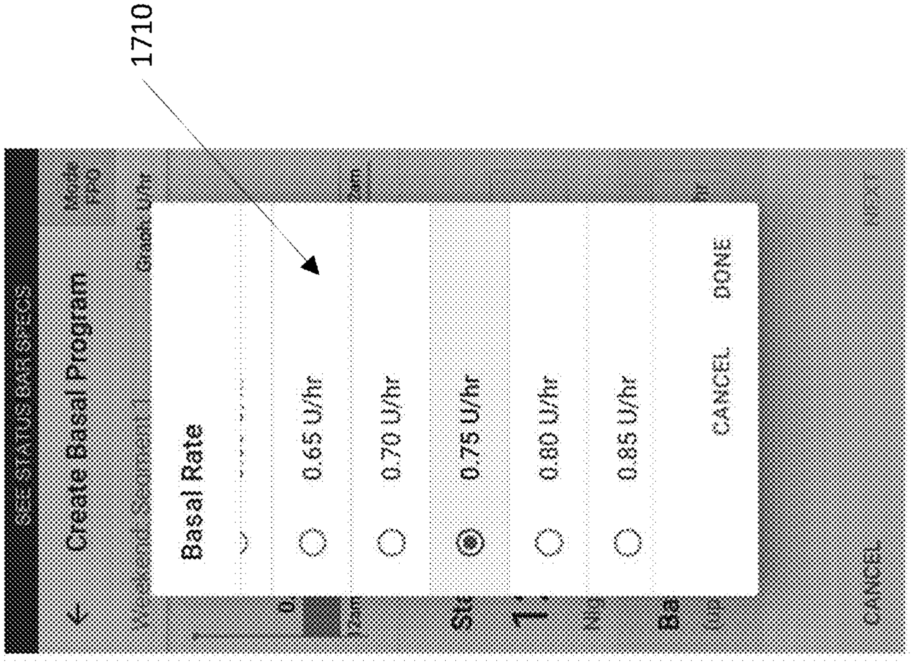
Figure 17E:
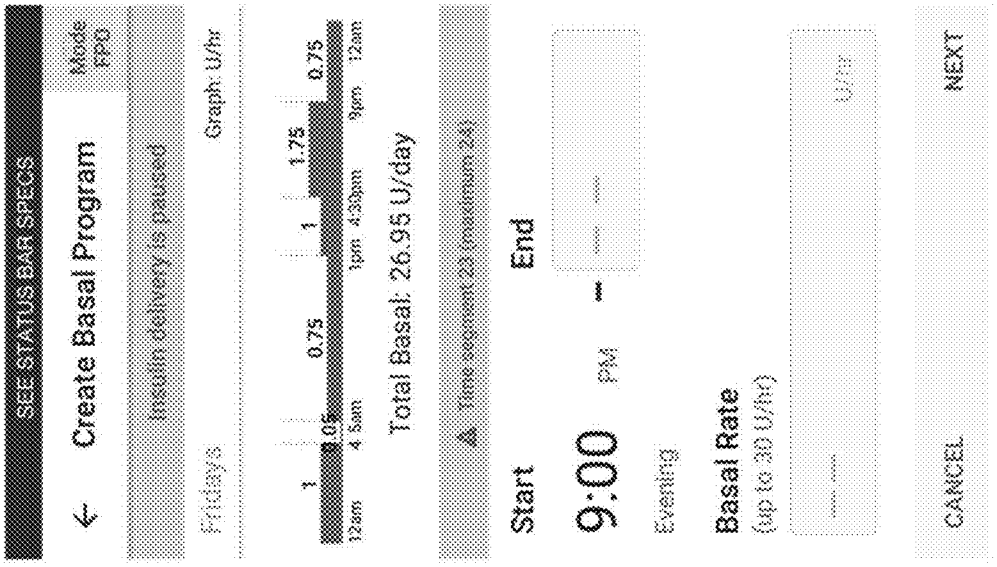
Figure 17F:
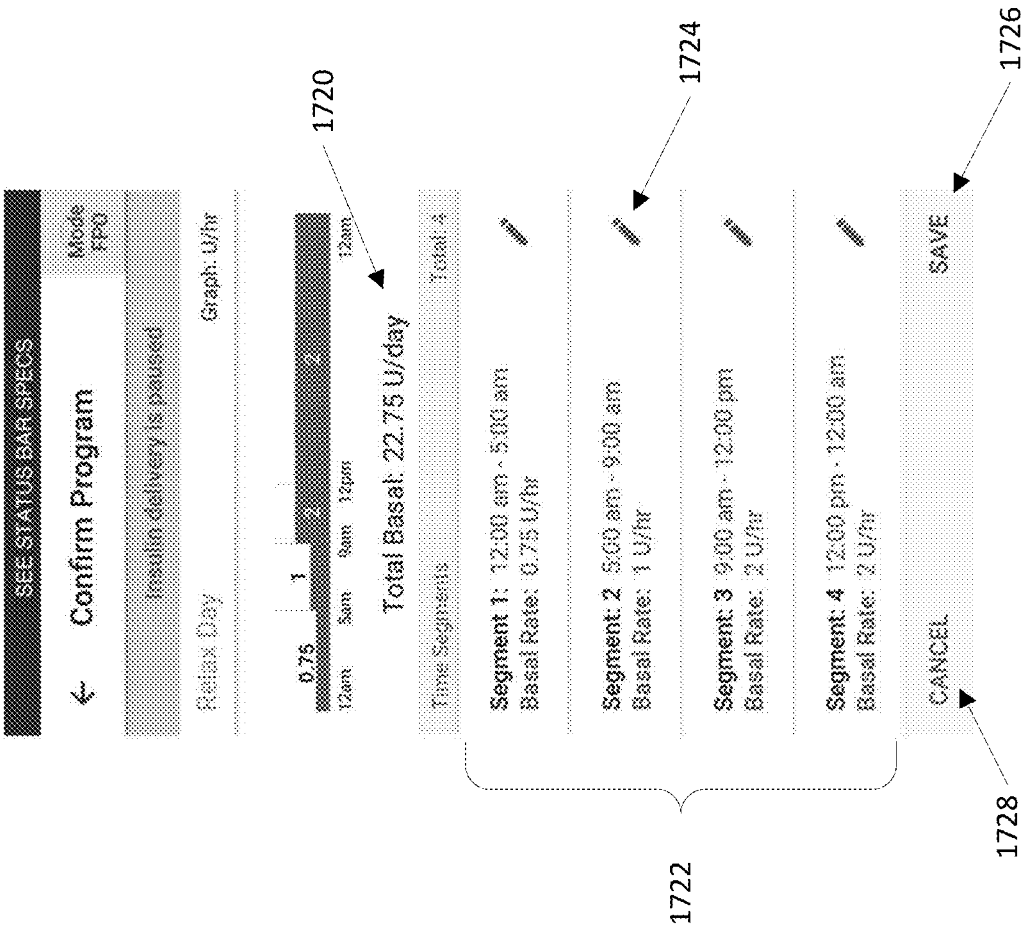

FIG. 17*c* shows a basal rate modal menu 1710 which may be used by the user to select the basal rate for the current segment. This menu may be invoked by providing a user selection of the basal rate field 1705 shown in FIG. 17*b*. Once the user has selected a basal rate, the selected basal rate is used to fill field 1705, as shown in FIG. 17*d*. In addition, a bar 1712 indicating the basal rate for the time segment is placed in area 1707 of the screen between the vertical lines indicating the start and end times of the segment. FIG. 17*e* shows a nearly completed basal program, while FIG. 17*f* shows a completed program with each segment of the program listed in list 1722. Any segment of the program may be edited by a user selection of the edit button 1724 next to that segment. The total quantity of insulin to be delivered by the basal program 1720 is shown under the graph. Once the user is satisfied with the basal program basal program may be saved by selecting button 1726 ("Save"). The creation of the basal program may be canceled at any time by pressing button 1728 ("Cancel").

Temporary Basal Screens

The temporary basal feature of user app 160 allows the user to temporarily modify the basal rate for a predetermined period of time. For example, the user may have done some exercise or retired early and as such the basal needs are reduced during those periods. To invoke this feature, the user should provide a selection of the menu button 414 on home screen 400. Once the menu has been displayed, as shown in FIGS. 13(*a-b*), the user should provide a selection of menu button 1302 ("Set Temp Basal"), which will cause the screen shown in either FIG. 18*a* or FIG. 18*c* to be displayed. The user has the option of entering the basal rate to be delivered during the temporary basal profile as either a percentage of the basal rate being delivered as part of the currently executing basal program or by an absolute number of units. The option may be set in the "Settings" portion of user app 160, which will be discussed later.

Figure 18B:
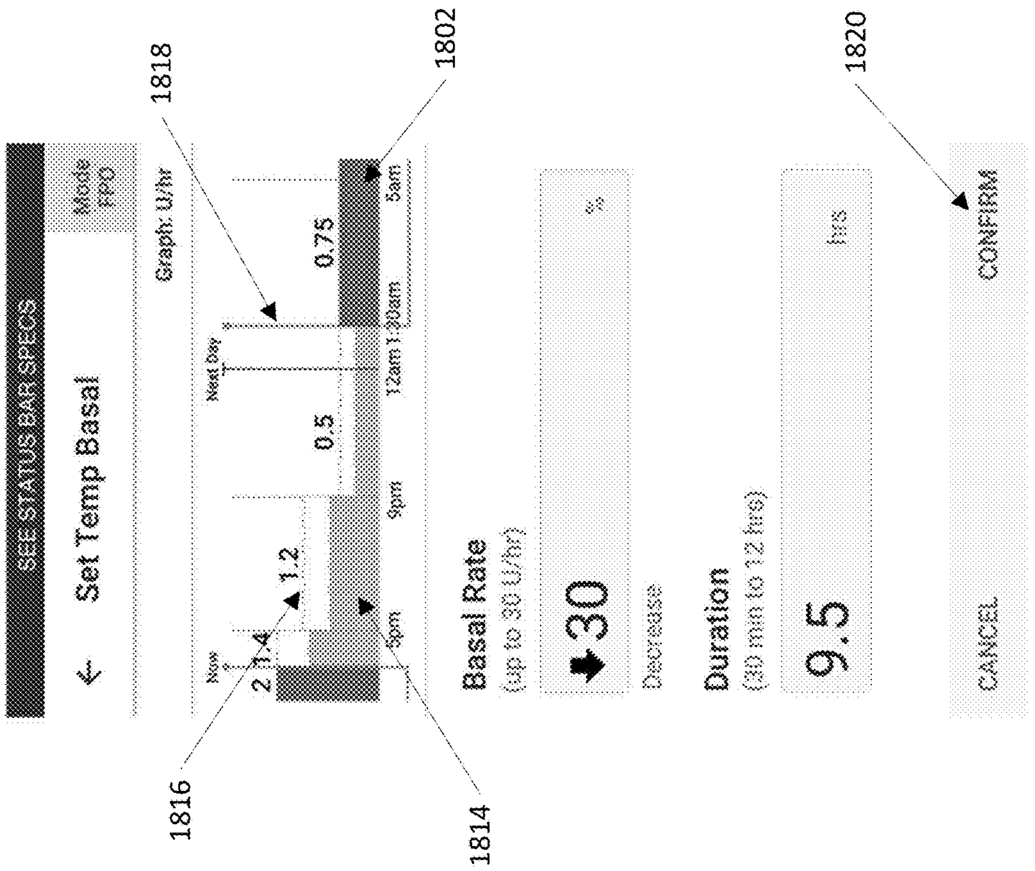
FIGS. 18(*a-f*) show examples of screens that allow the user to create or select a temporary basal profile.
Figure 18A:
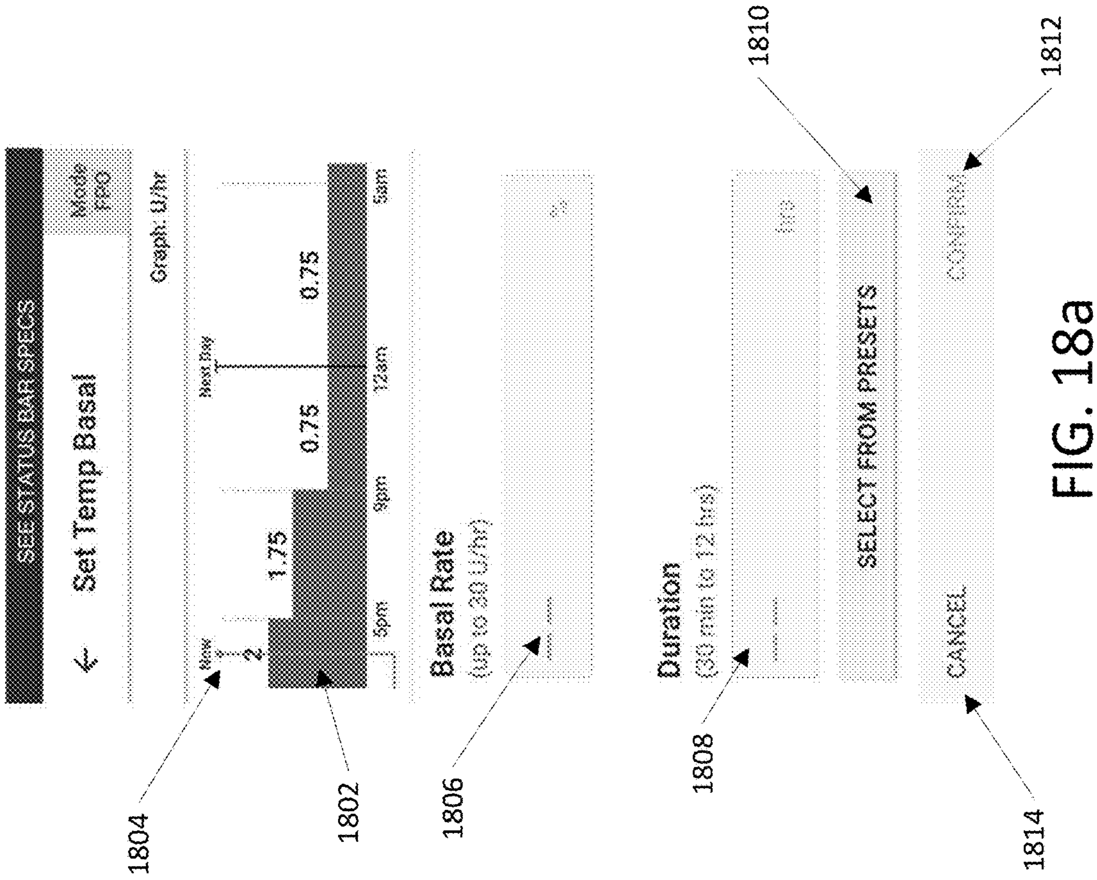
Figure 18D:
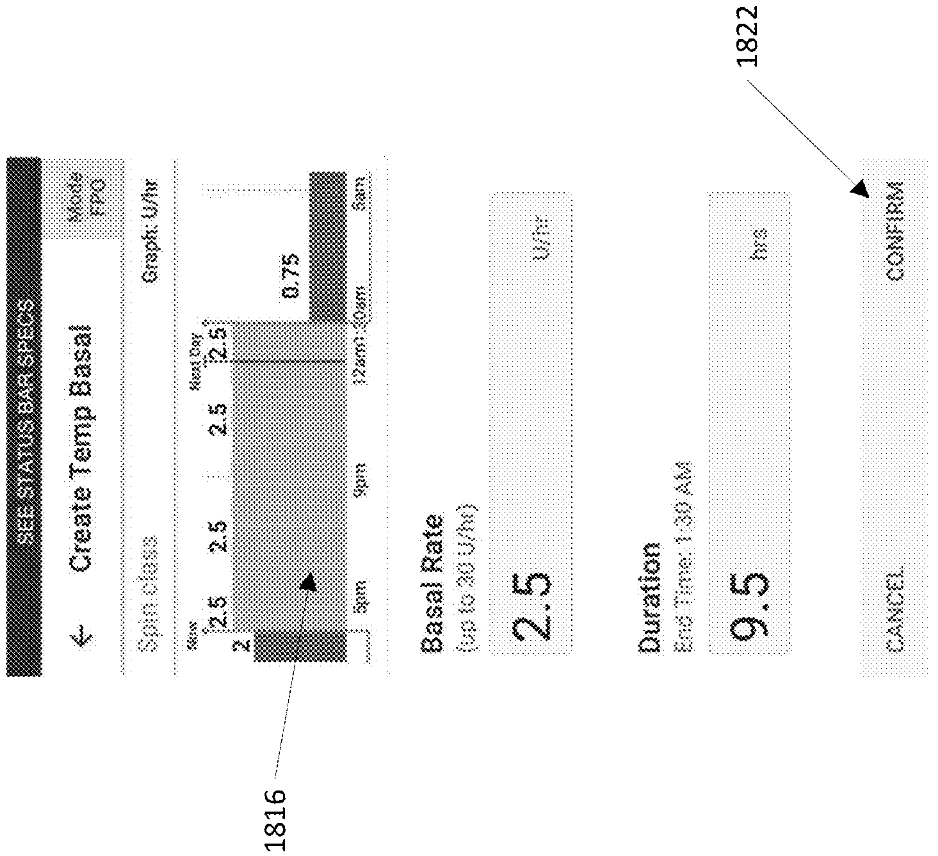

FIG. 18*a* is an example of the screen where the user may set the temporary basal rate as a percentage of the basal rate currently executing basal program. The graph for the currently executing basal program 1802 is shown in informational area 404 of the screen 400. Also displayed is a vertical line 1804 indicating the present time (i.e., "Now"). The basal rate may be set by entering the rate in units per hour in field 1806. In some embodiments, when field 1806 is selected, a modal screen may appear providing a list of basal rates from which the user may select, and, once the user has selected a basal rate, field 1806 is populated with the selected basal rate. In field 1808, the user sets the duration of the temporary basal. The user may enter the duration in field 1806, or, in some embodiments, when field 1808 is selected, a modal menu may appear having menu items for various durations. When the user has selected a duration from the modal menu, field 1808 is populated with the selected duration.

Alternatively, the user may forgo specifying a basal rate and a duration instead choose to select the temporary basal profile from a list of saved temporary basal profiles by selecting button 1810 ("Select From Presets"). At any time, the user may cancel the creation of the temporary basal profile by selecting button 1814 ("Cancel"). Once user has entered a basal rate in field 1806 and a duration in field 1808, a user may confirm the selections by selecting button 1812 ("Confirm"), which causes the screen shown in FIG. 18*b* to appear.

FIG. 18*b* shows the screen which is displayed after the user has confirmed the specification of the temporary basal profile. In informational area 404 of the screen, the basal profile 1802 from the currently running basal program is displayed with the temporary basal profile 1814 overlaid thereon. Preferably, the temporary basal profile 1814 is shown in a different color than the basal profile from the currently running basal program. Dotted line 1816 shows the basal profile from the currently running basal program, such that the difference between the basal profile the temporary basal profile may be observed. Vertical line 1818 shows the end of the temporary basal profile. The specified basal rate and duration are shown in fields 1806 and 1808 respectively. Once user is satisfied with the profile product, the profile may be confirmed by pressing button 1820 ("Confirm").

The screen shown in FIGS. 18(*c-d*) are similar to the screens shown in FIGS. 18(*a-b*) except that the basal rate is specified in field 1822 as an absolute number of units per hour instead of as a percentage of the basal profile of the currently running basal program. Once the profile is confirmed, the screen shown in FIG. 18*d* is displayed, showing the temporary basal profile 1816 displayed overlaid on the basal profile of the currently running basal program.

The user may either create a temporary basal profile or set a temporary basal profile. When a temporary basal profile is being created, as shown in FIGS. 18(*c-d*), providing a user selection of button 1822 ("Confirm") will navigate to a screen wherein the temporary basal profile may be saved. If a temporary basal profile is being set, as shown in FIGS. 18(*a-b*), providing user selection of button 1820 ("Confirm") will navigate to the screen wherein the temporary basal profile may be started.

Figure 18C:
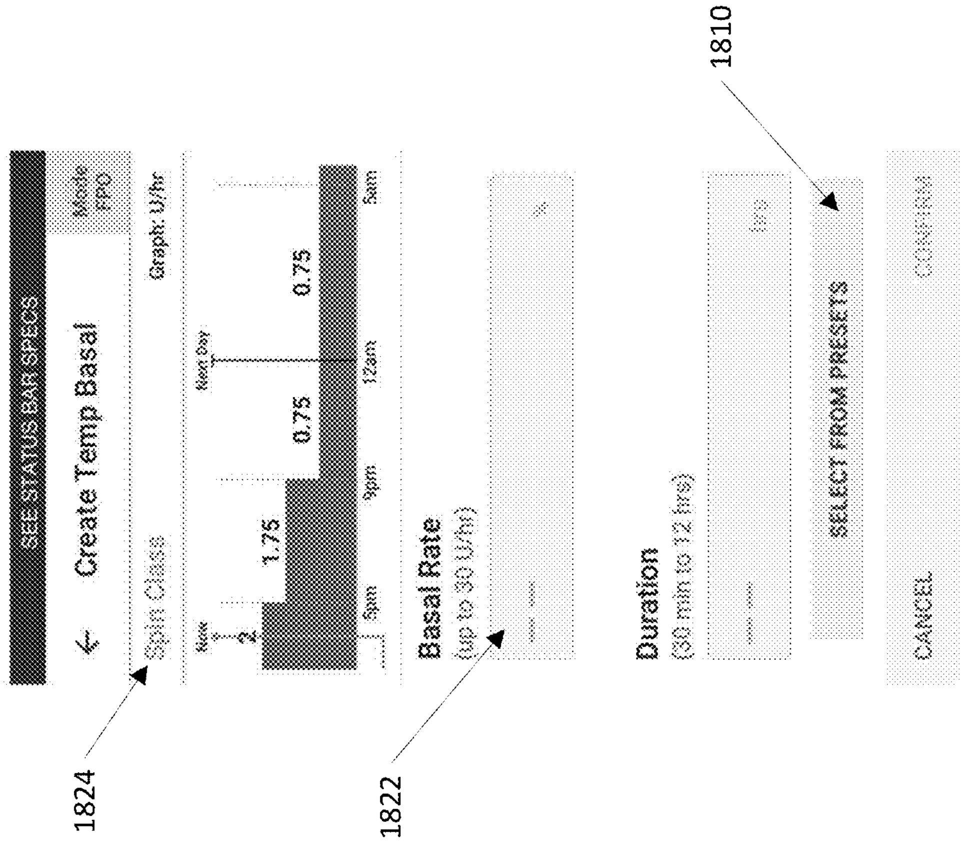
Figure 18F:
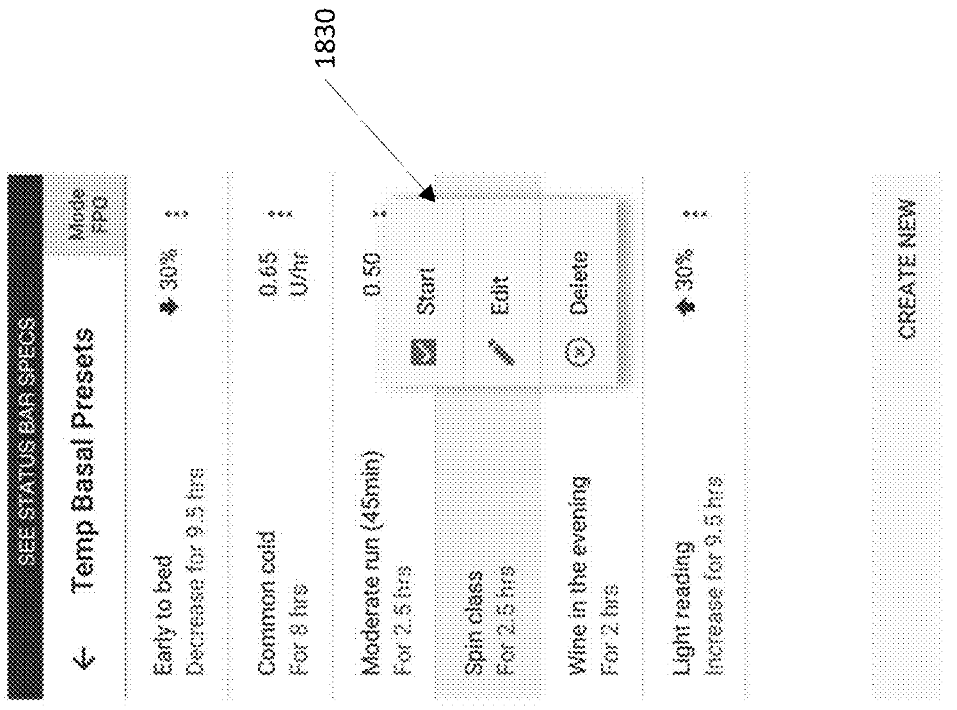
Figure 18E:

A selection of button 1810 from the screen shown in either FIG. 18*a* or FIG. 18*c*, will navigate to the screen shown in FIG. 18*e*, showing a list of saved temporary basal profiles 1824. Also provided on this page, the back arrow 1826, when selected, navigates the user back to home screen 400. Further, button 1806 ("Create New") is also provided which, when selected, will allow the user to create a new temporary basal profile by navigating to either of the screens shown in FIG. 18*a* or FIG. 18*c*.

Selecting the menu indicator 1828 next to any of the saved temporary basal profiles listed in list 1824 causes a modal menu 1830 to appear as shown in FIG. 18*f*. The user may make a selection from modal menu 1830 to start, edit, or delete the respective temporary basal profile.

Blood Glucose Screens

User app 160 provides a means for the user to manually enter a blood glucose reading. Selecting button 1312 ("Enter BG") from the menu shown in FIGS. 13(*a-b*) causes user app 160 to display the blood glucose entry screen shown in FIG. 19*a*. In one embodiment, the user is provided with a circular graphic 1902 having circular cursor 1903 which may be moved by the user around circle 1902. Moving the cursor 1903 in a clockwise direction increases the blood glucose reading, which is shown in the center of the circle in field 1904. Alternatively, the user may provide a user selection of field 1904, which will cause a modal keyboard to appear allowing the user to enter the blood glucose reading. When the modal keyboard is dismissed, the blood glucose reading is transferred to field 1904. As would be realized by one of ordinary skill in the art, many other means of entering the manual blood glucose level are possible and are still contemplated to be within the scope of the invention.

Figure 19B:
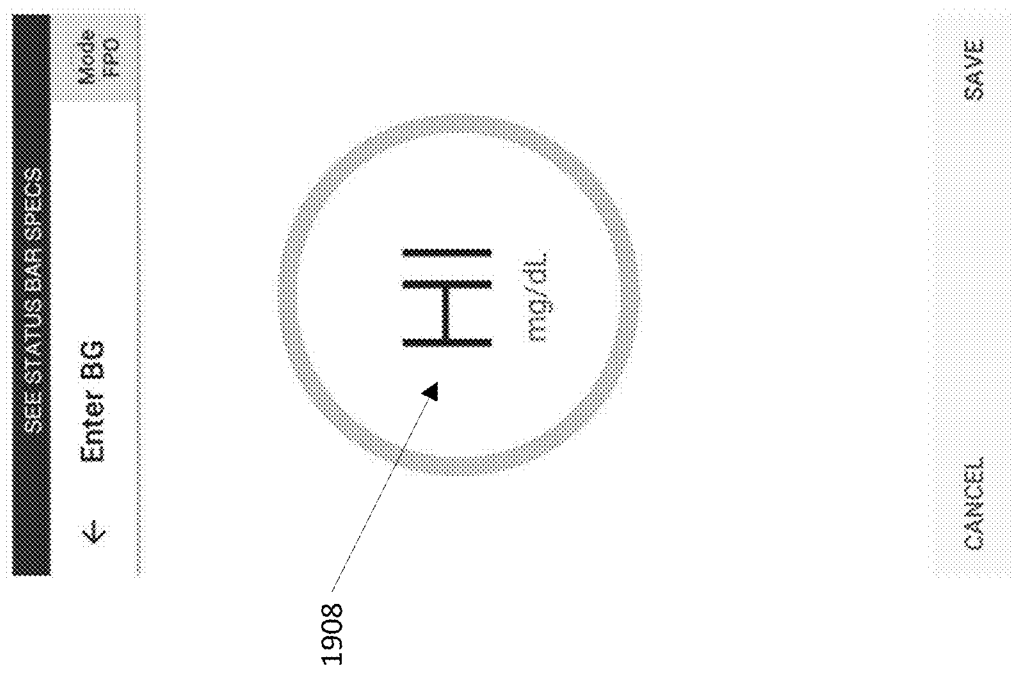
FIGS. 19(*a-d*) show examples of screens that allow the user to manually enter a blood glucose reading.
Figure 19A:
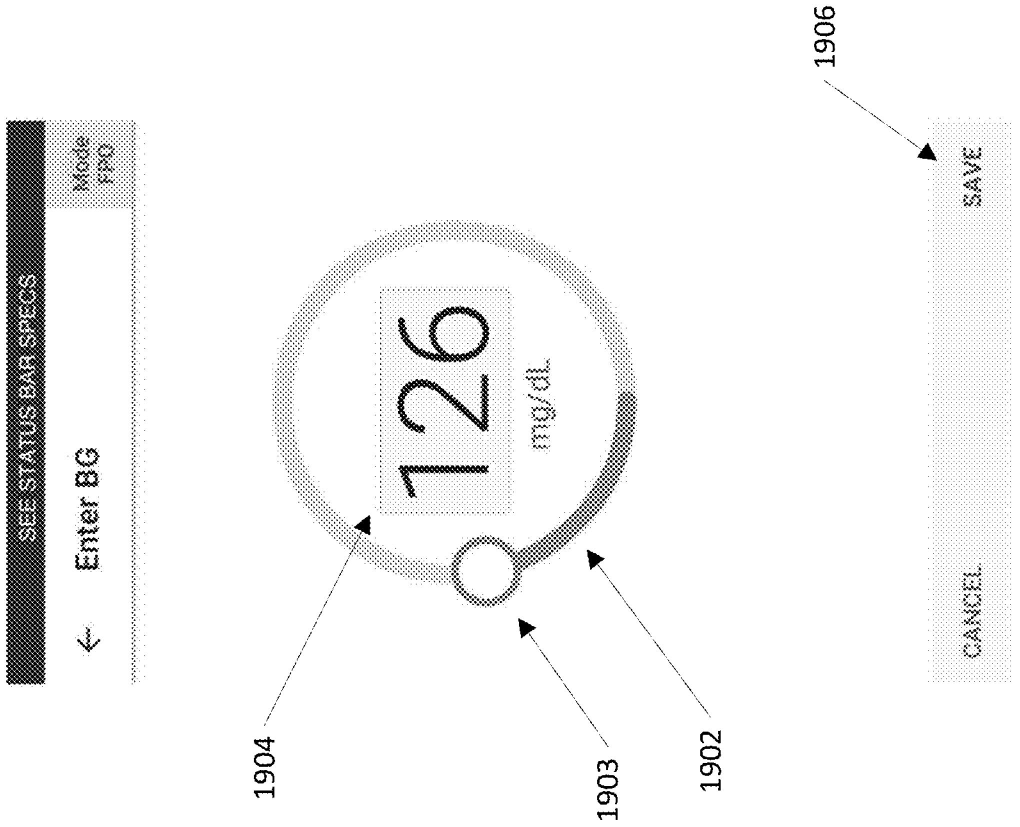
Figure 19D:
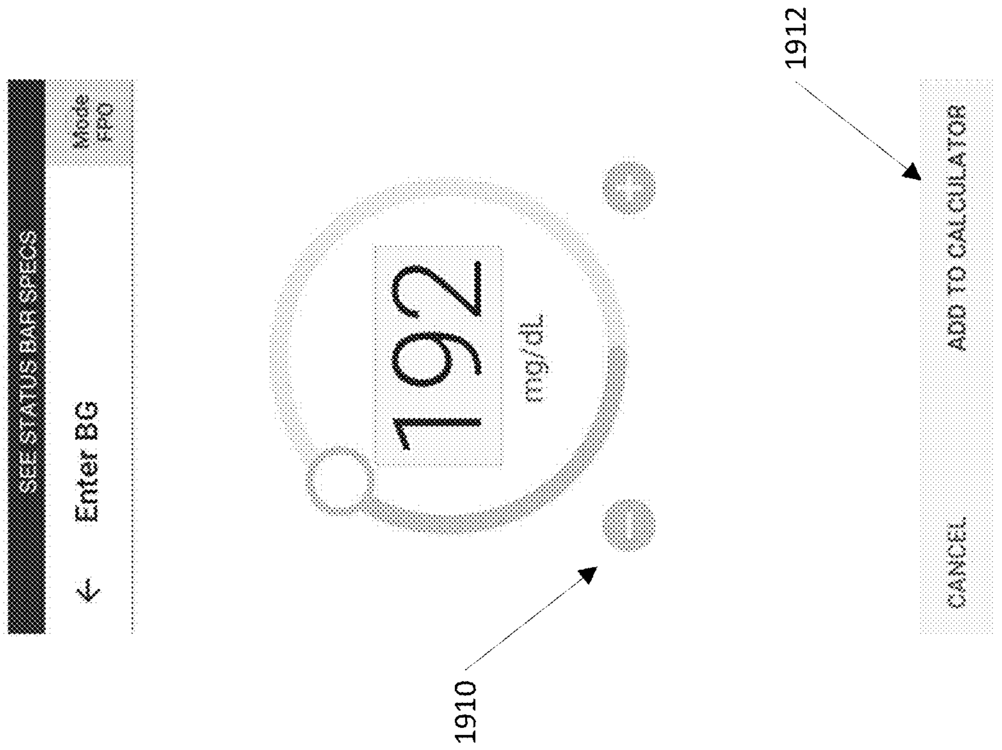
Figure 19C:
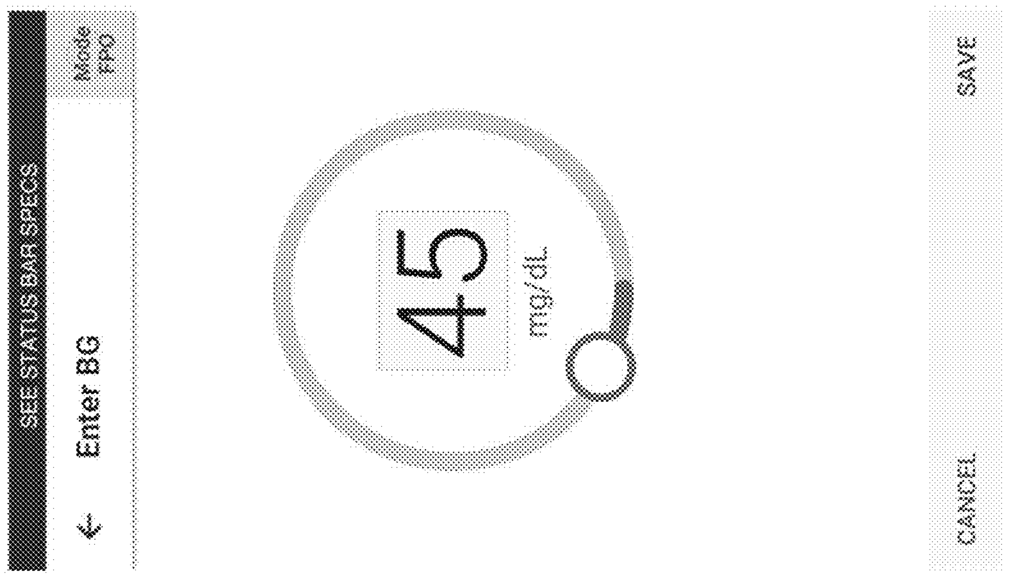

The color of circular graphic 1902 may change depending upon the value of the blood glucose reading displayed in field 1904. For example, circular graphic 1903 may appear yellow in color, as shown in FIG. 19*b*, when the blood glucose level is above the user's target range, but below a preselected upper threshold. Should the blood glucose level reading displayed in field 1904 rise above the upper threshold, the graphic displays "HI" in field 1904. Likewise, in the event that the value entered is below the user's target range, but above a preselected lower threshold, circular graphic 1902 may be displayed in a red color, as shown in FIG. 19*c*. Should the blood glucose level reading displayed in field 1904 fall below the lower threshold, a "LOW" indication may appear in field 1904. Once the blood glucose level has been entered in field 1904 and confirmed by the user, the user may save the reading by pressing a button 1906 ("Save"). In a first variation of this embodiment, shown in FIG. 19*d*, the graphic may be modified by adding plus and minus signs for a few seconds after the user has lifted their finger from cursor 1903, allowing the user to increase or decrease the blood glucose reading displayed in field 1904 by 1, to allow finer control. In a second variation, the blood glucose entry screen may be displayed directly from the bolus calculator shown in FIG. 11*a* by tapping field 1104. As shown in FIG. 19*d*, button 1906 ("Save") has been replaced by button 1912 ("Add To Calculator") which, when selected by the user, adds the blood glucose value shown in field 1904 to the blood glucose field 1104 of the bolus calculator shown in FIG. 11*a*.

Food Library Screens

User app 160 may provide a food library which will aid the user in determining the grams of carbohydrates contained in the meal, which are used by the bolus calculator to calculate a bolus dose of insulin.

Figure 20A:
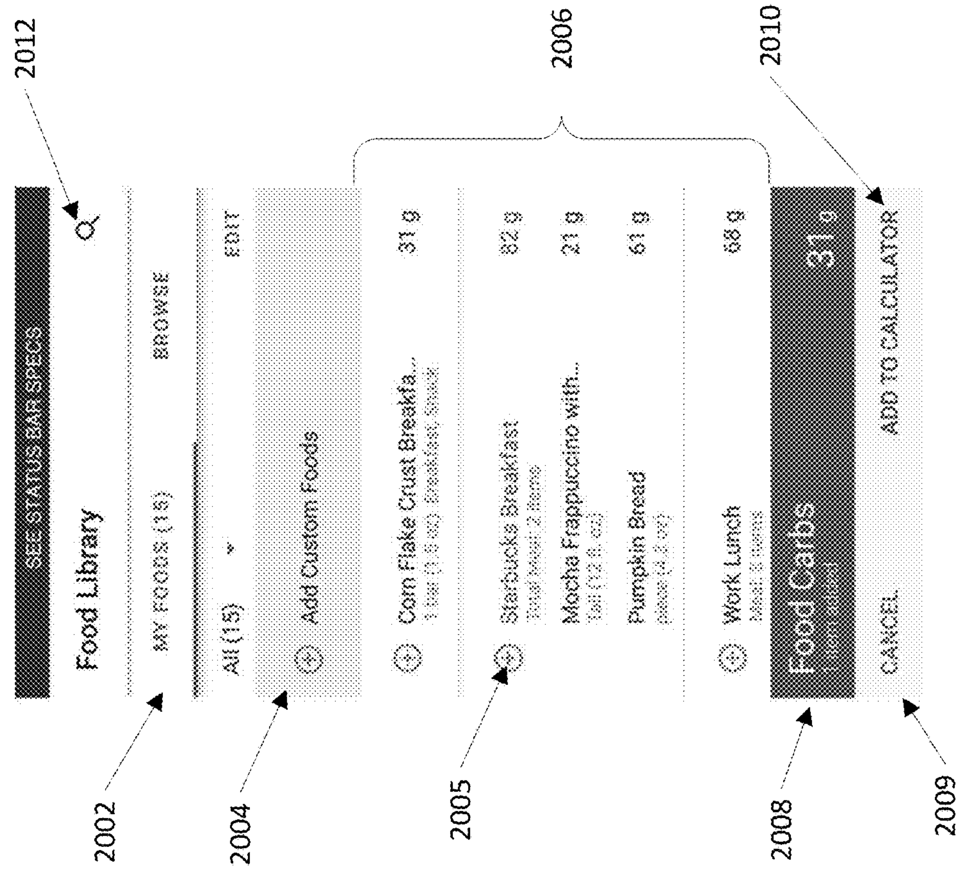
FIGS. 20(*a-d*) show examples of screens implementing a food library which the user may use to select foods to add to a meal for purposes of calculating the total carbs consumed during the meal.

FIG. 20*a* shows screen 2000 which is displayed when the user chooses to view the food library. Screen 2000 includes a tab bar 2002 containing two tabs, a "My Foods" tab and a "Browse" tab. When the "My Foods" tab is selected, a list 2006 of foods is displayed. The displayed list 2006 of foods includes, for example, foods that the user has recently selected or foods that the user has indicated as being "favorites". A food item in the "My Foods" list 2006 may be added to the card total for the meal by pressing a button 2005 ("+"). When button 2005 is pressed, the carb content of the selected food is added to the food carb total 2008 displayed below the list. The food carb total 2008 includes both the number of items selected and the sum of the carbs for each of the selected food items. Once the user has completed the selection of foods, a user selection of button 2010 ("Add To Calculator") will add the food carb total 2008 to the carb field 1102 of the bolus calculator shown in FIG. 11*a*.

Figure 20B:
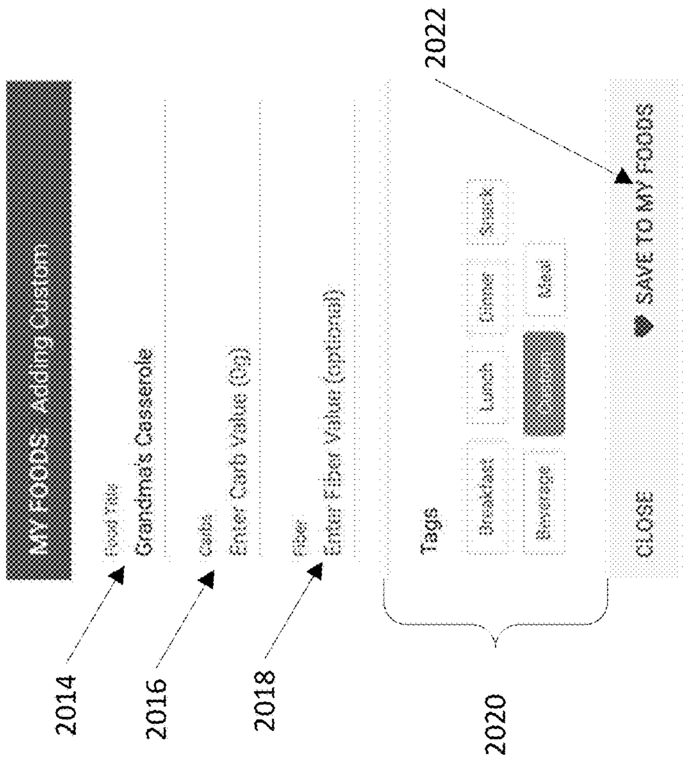

The "My Foods" screen also includes a button 2004 ("Add Custom Foods") which allows the user to add a customized food choice, for example, in the event that the food does not currently exist in the food library. Selection of button 2004 will cause the bottom portion of the "My Foods" screen to be replaced with the screen shown in FIG. 20*b*, which allows the user to enter details about the custom food. In field 2014, the user is able to provide a name for the food. Selection of field 2014 will cause a modal alphanumeric keyboard to appear which user may use to enter the name of the custom food. When the modal alphanumeric keyboard is dismissed, the name of the food will be transferred to field 2014. In field 2016, the user is able to enter the carb value of the foods via a modal numerical keyboard, and, in field 2018 user is (optionally) able to enter the fiber content of the custom food via a modal numerical keyboard. In area 2020 of the screen the user is able to select various tags to the custom food. Once the user has entered all of the details of the custom food, a selection of button 2022 ("Save To My Foods") causes a custom food to be added to the list in "My Foods" list 2006 shown in FIG. 20*a*.

Figure 20D:
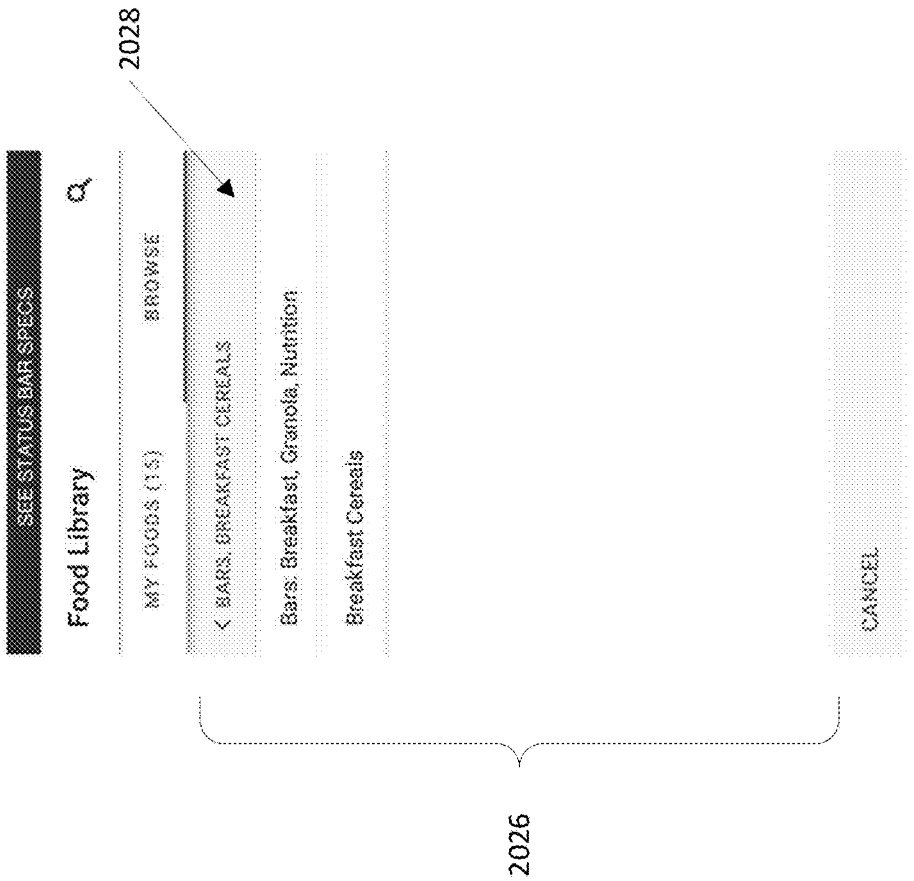
Figure 20C:
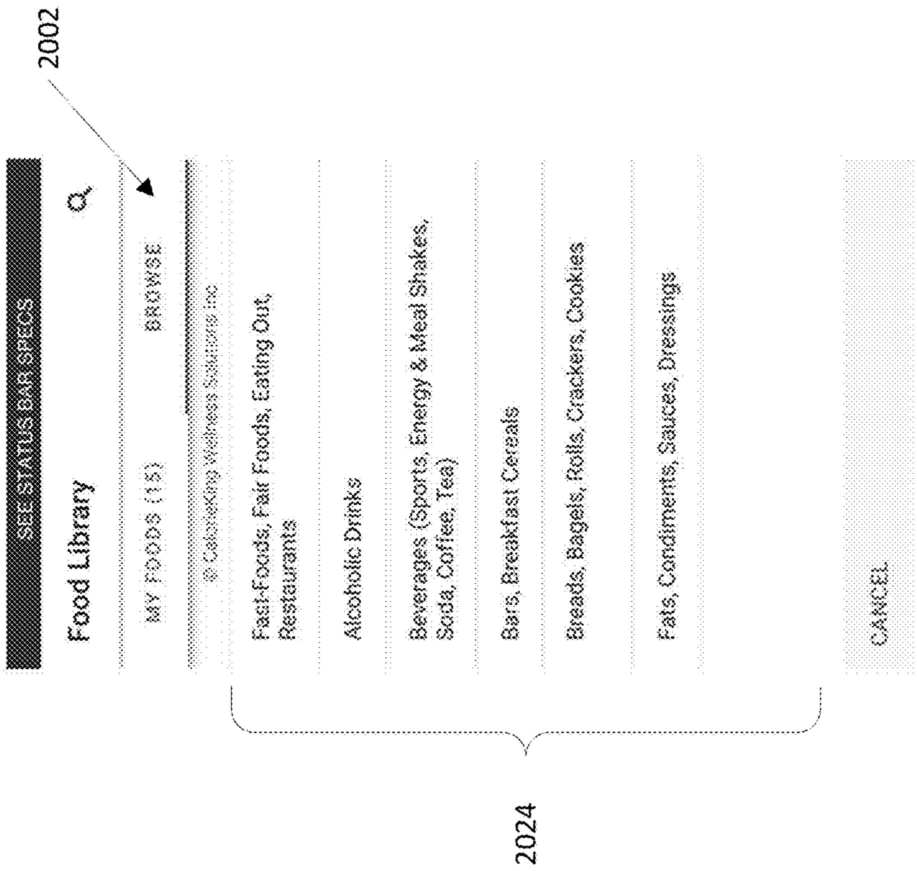

When the "Browse" tab is selected from tab bar 2002, the user is able to browse the food library by category. An initial list of categories is shown in list 2024. When one of the categories is selected, for example, the "bars, breakfast cereals" tab, the secondary categorization is shown in FIG. 20*d* as list 2026. Repeated selection of categories will eventually lead to individual food items which the user may select to add to the carb total for the meal and/or add to the "My Foods" list 2006. The user may return to previously viewed categories by pressing a button 2028 which will cause the screen shown in FIG. 20*c* to be displayed. Each of the screens in the food library is configured with a button 2009 ("Cancel") which, when selected, will return the user to either the home screen 400 or to the bolus calculator screen shown in FIG. 11*a*.

First-Time Setup Screens

Figure 21B:
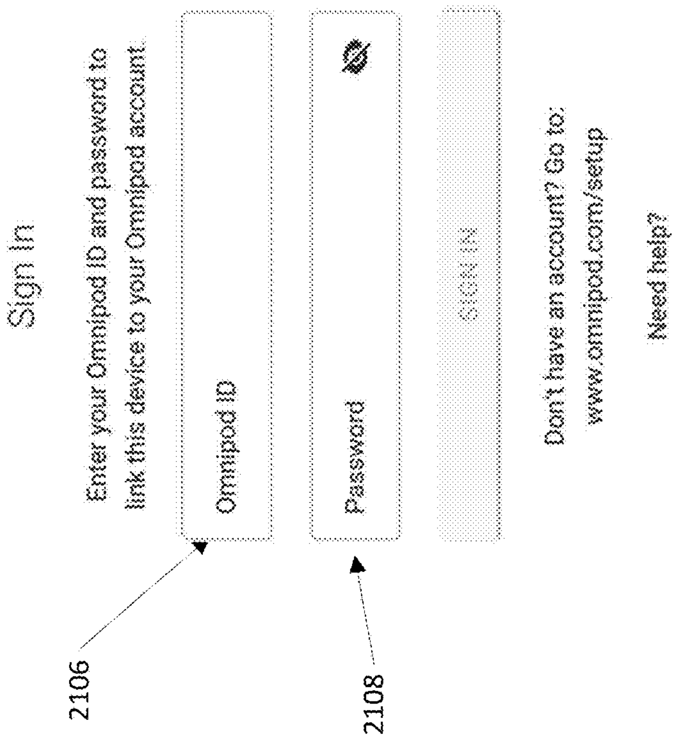
FIGS. 21(*a-g*) show examples of screens used for the initial set up of the user application.
Figure 21A:
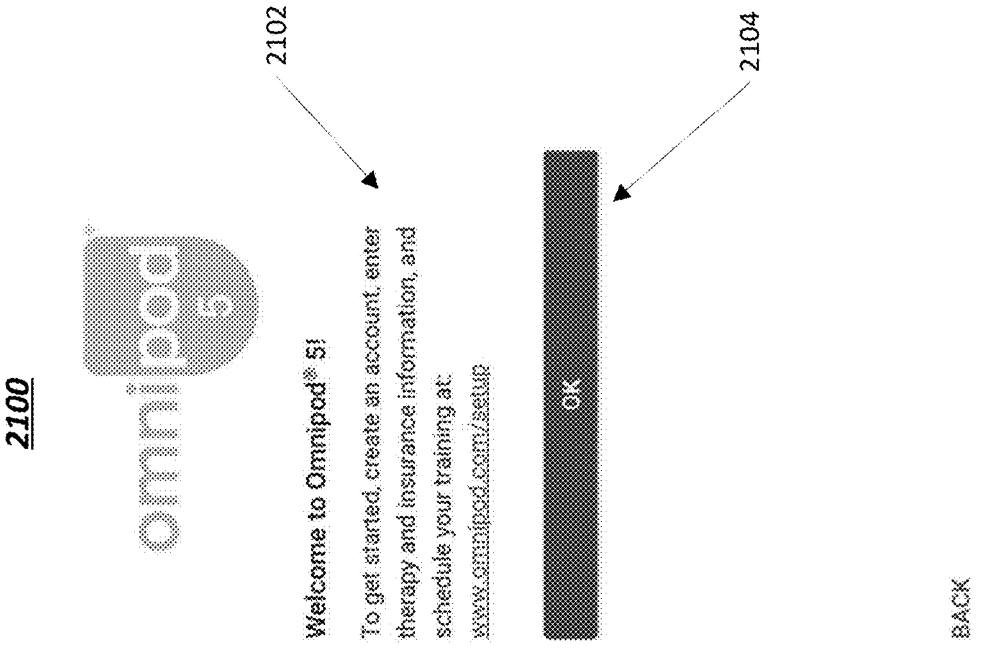

User app 160 provides a series of screens allowing the user to perform first-time setup of user app 160. The functions provided by the screens are to be performed one time only, typically, the first time the user starts user app 160. Upon starting user app 160 for the first time, the user may be provided with a "Welcome" screen 2100 similar to that shown in FIG. 21*a*. The welcome screen 2100 may include a welcome message 2102 and a button 2104 ("OK") which allows users to move on to the next screen. As part of the setup, a user may be required to enter certain information online. FIG. 21*b* shows a screen that allows the user to login to an online facility where the user can input certain information required to operate the wearable drug delivery device 102. To access the user's account on the online facility, the user may be required to enter a username 2106 and password 2108.

Figure 21D:
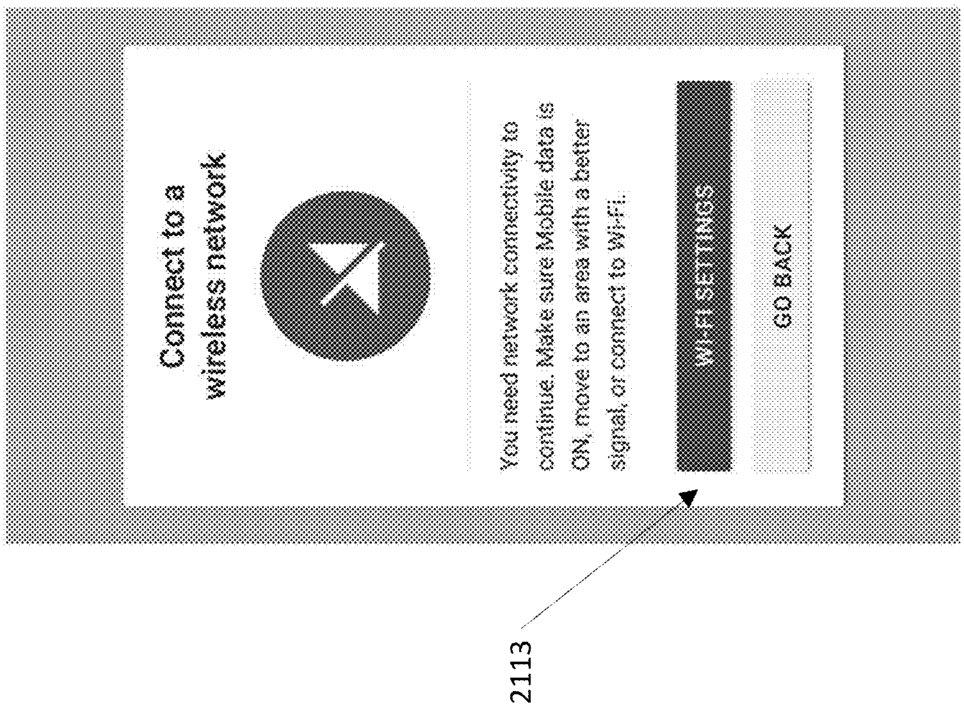
Figure 21C:
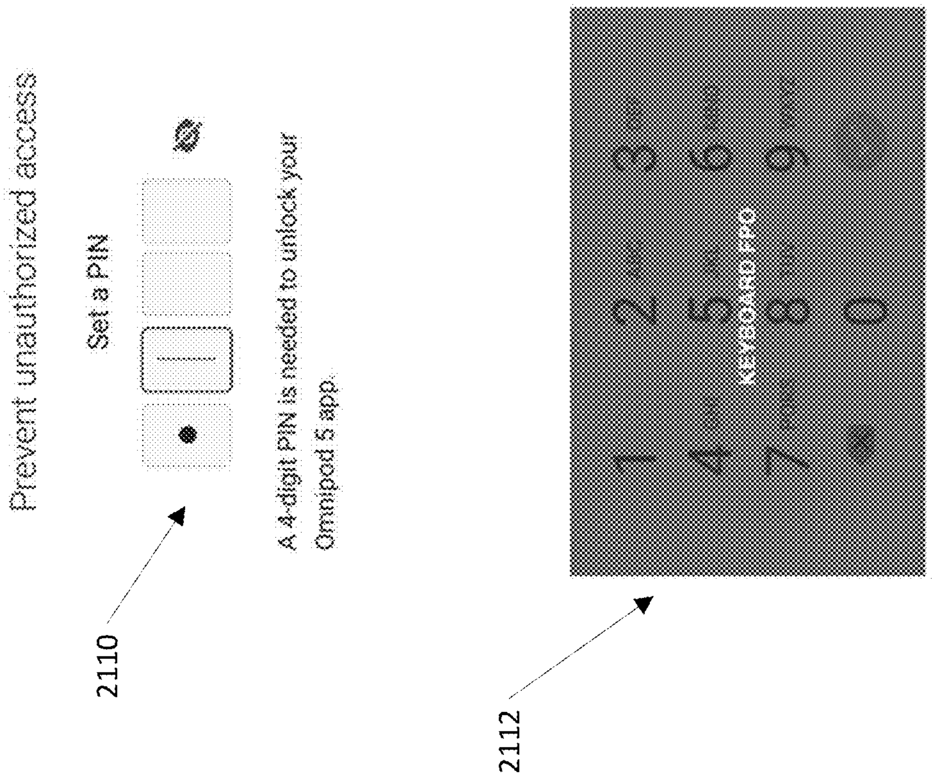

Certain aspects of the setup of user app 160 may be performed locally. As an example, FIG. 21*c* shows a screen where the user is able to set a security PIN 2110 to limit access to user app 160. The user may be provided with a modal keyboard 2112 which allows entry of the pin. An additional screen may follow that which allows user to certify the entry of the pin by re-entering the PIN. FIG. 21*d* shows a screen which allows the user to enter Wi-Fi settings which allow connection to a wireless access point to provide access to the Internet. The user may access a screen where the Wi-Fi settings may be entered (not shown) by providing a user selection of button 2113. In some cases, the selection of button 2113 may take the user to the native Wi-Fi settings screen for the user device 105 on which user app 160 is executing. In some cases, the user device 105 on which user app 160 is executing may already be connected to a wireless access point, in which case, the screen shown in FIG. 21*d* may not be necessary.

Figure 21E:
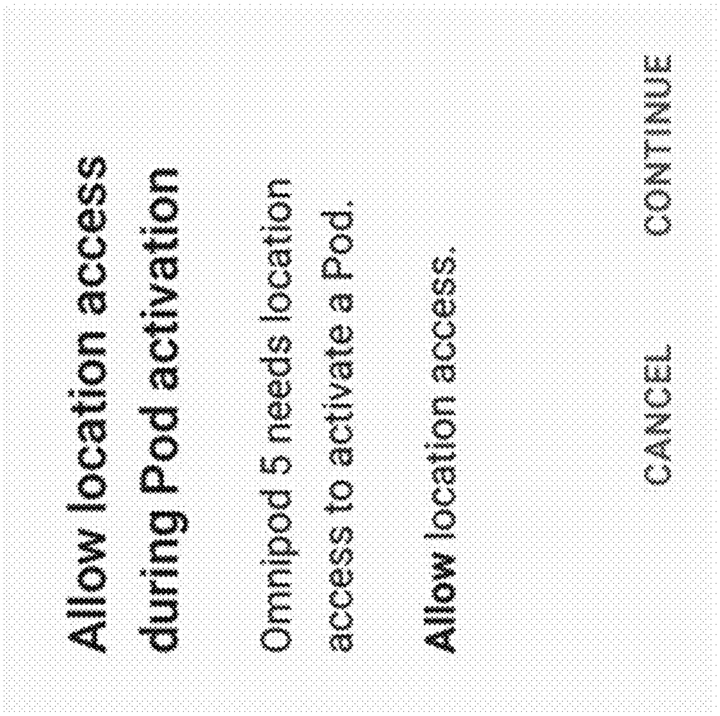

During the setup process, user app 160 may determine that access to the location information of user device 105 is necessary. For example, user app 160 may wish to track the current location of user device 105 to determine in which time zone user device 105 is currently located and to adjust the time zone as the user moves between time zones. The time zone may be used as the basis from which the times for the insulin delivery are calculated. The user may be presented with the modal screen shown in FIG. 21*e*, which allows the user to grant access to the location information of user device 105 to user app 160. The screens shown in FIGS. 21(*a*-*e*) are exemplary in nature and, as would be realized, many other setup screens could be provided allowing the user to set up various other aspects of the user app 160. For example, the user may set up a message to be displayed when user app 160 is locked, for example, identifying the user's contact information and may be used in the event that user device 105 is lost. In addition, the user may be able to set up a personalized background which displays on the lock screen. Many other user-settable features may be available to the user.

Figure 21F:
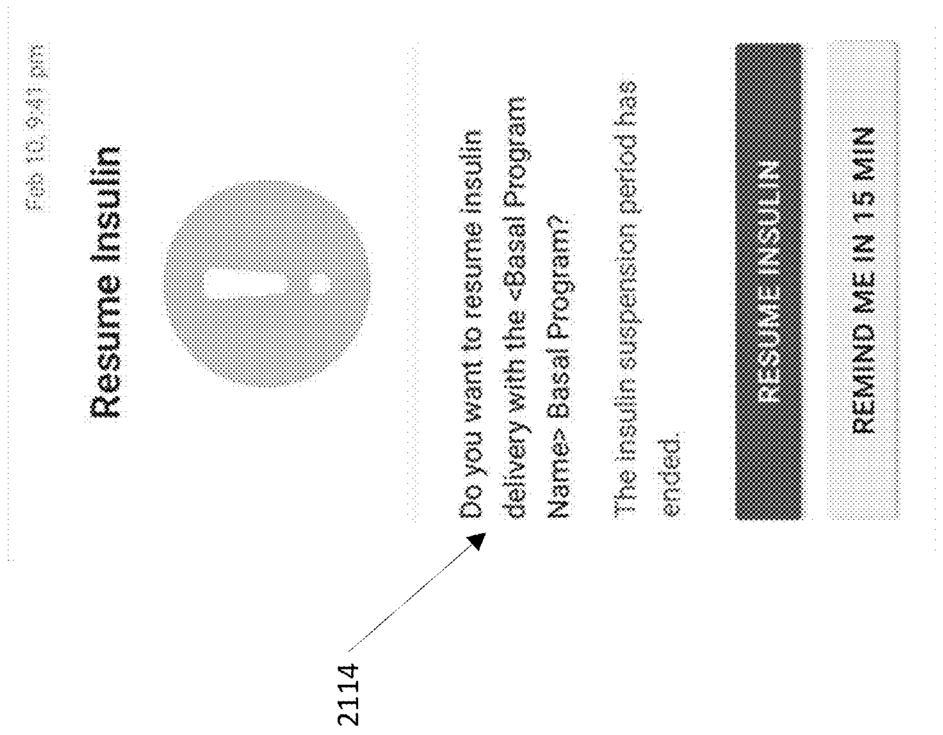
Figure 21G:
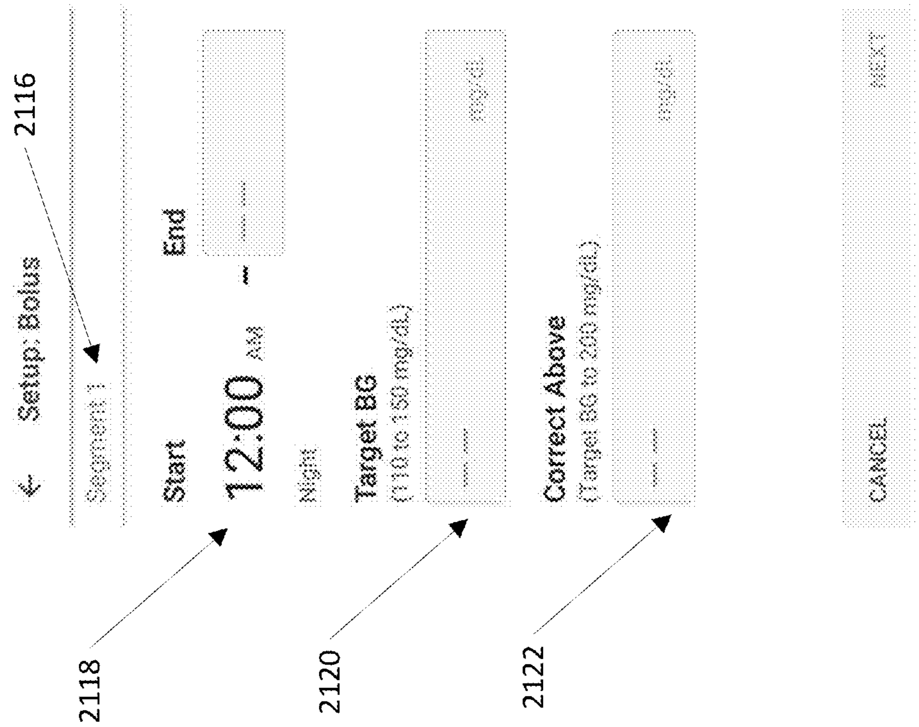

In addition to the general set up items, the user may be prompted to set up parameters for the delivery of both basal and bolus doses of the liquid drug. As an example, the user may set up a basal profile. FIG. 21*f* shows an exemplary screen which allows user to set a maximum basal rate by entering the units per hour in field 2114. FIG. 21*g* shows an exemplary screen allowing the user to set up a bolus. Field 2116 shows the name of the bolus while field 2118 allows the user to generate start and end times for the bolus. The user may also enter a target blood glucose level in field 2120 and a "Correct Above" value in field 2122. Many other parameters for the basal and bolus delivery of the liquid drug may be entered in other screens, similar to those already discussed above with respect to the bolus and basal doses of the liquid drug.

Alarm and Alert Screens

Figure 22A:
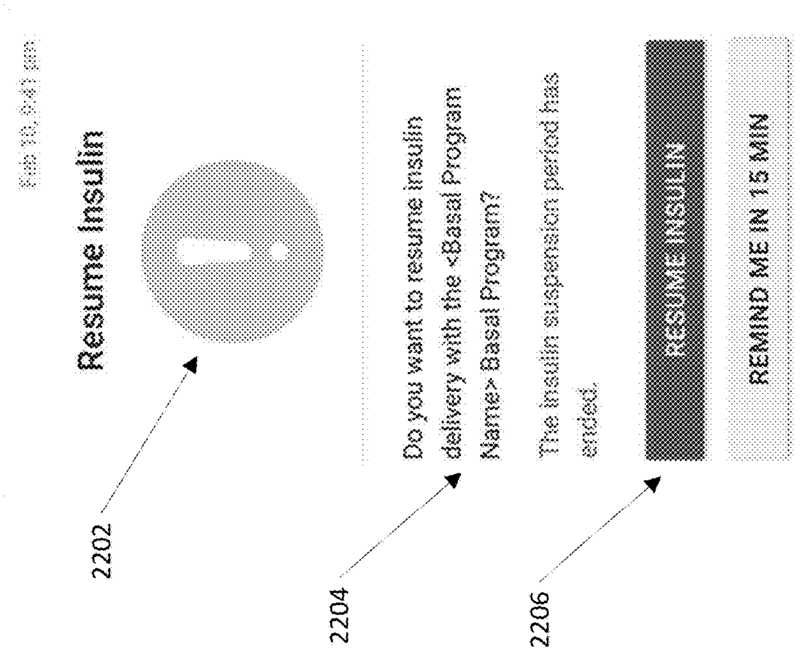
FIGS. 22(*a-c*) show examples of informational and error screens displayed by the graphical user interface.
Figure 22B:
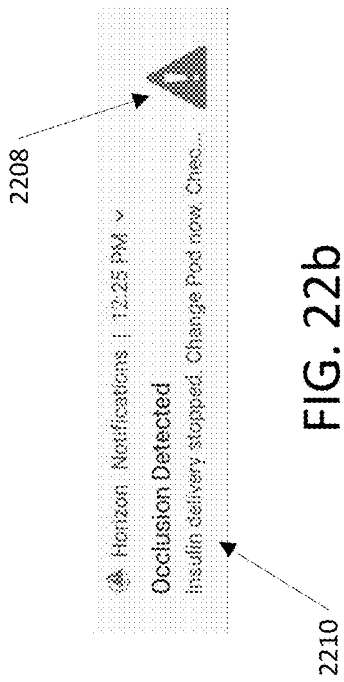
Figure 22C:
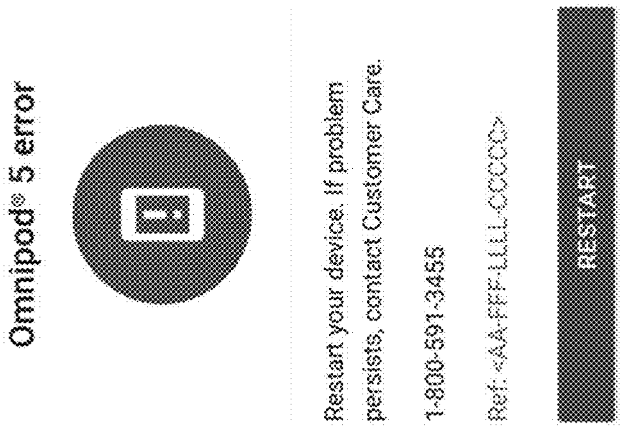

User app 160 may, at various points in its operation, provide screens showing alarms, alerts, and/or error screens to the user. In some instances, an alarm or alert may be accompanied by an exclamation point ("!") icon which may provide the icon on a background of a certain color, for instance, a yellow background as an example of which is shown as icon 2202 in FIG. 22*a*. The particular screen shown in FIG. 22*a* alerts the user that insulin delivery should be resumed. A message 2204 indicating the cause of the alert may be displayed as well as one or more buttons 2006 allowing the user to take an action in response to the alert. More serious errors or alerts may be provided by an icon showing, for example, an excavation point on a red background, as shown in FIG. 22*b* as icon 2208. In addition, a message describing the error and actions the user should take to resolve the error may be provided, as shown by message 2210 in FIG. 22*b*. Alerts and errors may be provided as full screens, as shown in FIG. 22*a*, or as modal pop-ups as shown in FIG. 22*b*. FIG. 22*c* shows yet another example of a general error.

History Screens

Figure 23A:
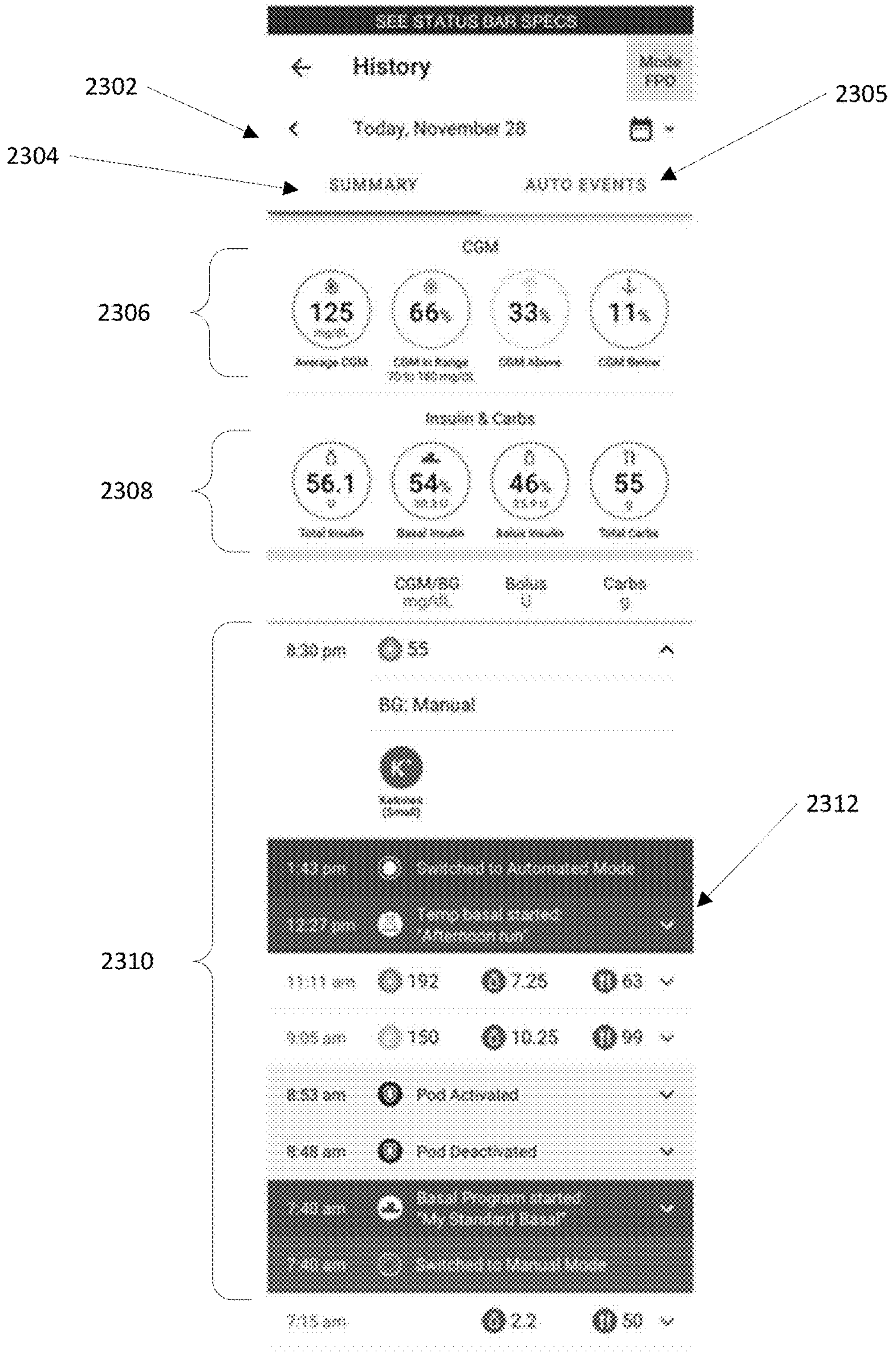
FIGS. 23(*a-c*) show examples of screens showing the history of the operation of the user application and the medication delivery device.

User app 160 has the capability to show the history of its operation. The history information may be accessed by user selection of button 1314 ("History Detail") in menu 1300. The default history screen appears as a vertical modal pop-up 2300, as shown in FIG. 23*a*, overlaying or replacing menu 1300. By default, the history screen shows the history information for the current day. However, the history information for other days may be shown by a user selection of button 2302 ("<"). History screen 2300 contains a tab button containing two tabs, a "Summary" tab 2304 and an "Auto Events" tab 2305. The screen showing the display when the summary tab 2304 is selected as shown in FIG. 23*a*. The display includes a CGM history 2306 that includes information regarding the average CGM reading and the percentage of the time that the user's blood glucose level has been in the user-specified range, above the range, and below the range. Also displayed when the summary tab 2304 is selected are insulin and carbs information 2308. This area of screen 2300 shows the total insulin delivered for the day, the percent delivered as basal insulin, the percent delivered as bolus insulin and the total carbs consumed by the user during the day.

Figure 23B:
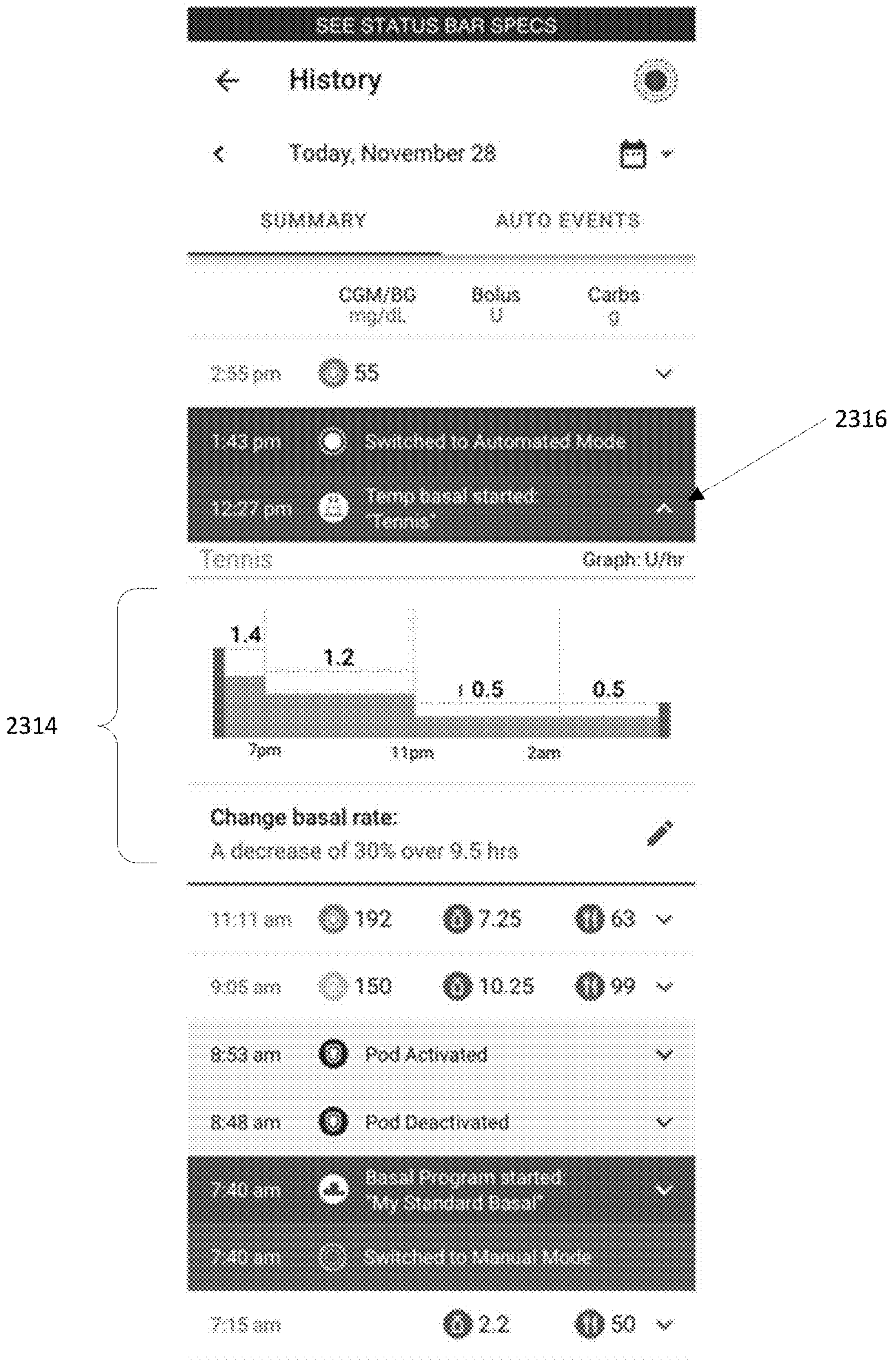

Area 2310 of history screen 2300 shows a timeline showing individual events and the time that those individual events happen. Further details about each individual event may be displayed by selecting, for example, down arrow 2312, which will cause the area to be expanded to display details regarding individual timeline events. As shown in FIG. 23*b*, the graph shown in area 2314 is displayed as a result of user selection of down arrow 2312 on the "Temp Basal Started" area of the timeline 2314. Different types of information may be shown when different timeline events are expanded. The timeline event may be collapsed by selecting button 2316, which would cause the graph shown in area 2314 to disappear.

Figure 23C:
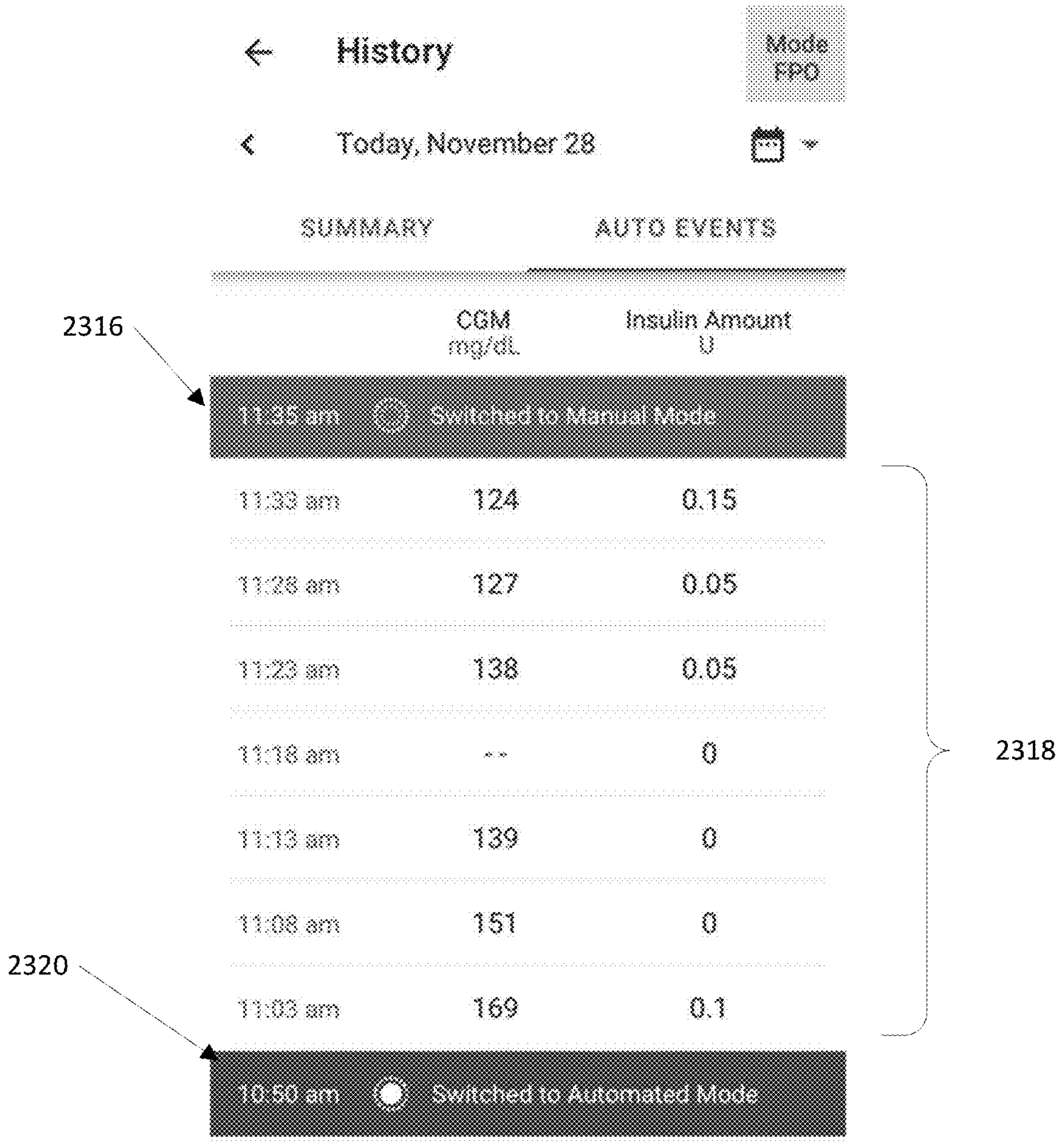

A selection of the "Auto Events" tab 2305, results in display of the screen shown in FIG. 23*c*. this screen shows event banners and data rows. Event banners 2316, 2320 show mode switch events and time zone switch events. Event banners 2316, 2320, may be displayed in different colors, for example, a purple banner may be displayed when automated mode begins in a blue banner may be displayed when automated mode ends. This screen also data rows 2318 which show CGM readings and delivered micro-bolus doses.

Settings Screens

All user-settable options and settings of user app 160 may be accessed from button 1316 ("Settings"), as shown in FIG. 13*a*. Button 1316 may be expanded to show expanded settings menu 1318. FIG. 13*a* shows the settings menu in expanded form.

Figure 24A:
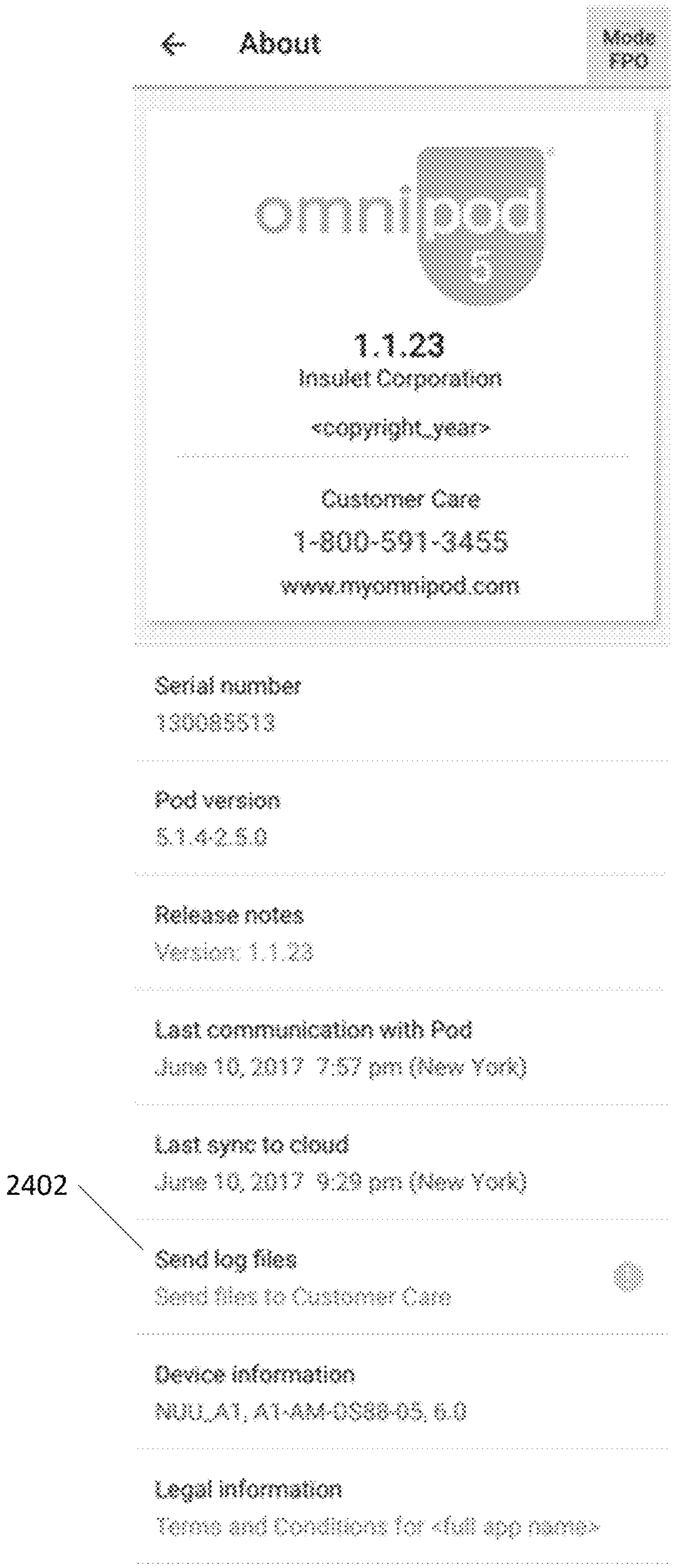
FIG. 24*a* shows an example of a screen showing information about the user application and related devices.

Upon a user selection of button 1320 ("About"), main menu 1300 is replaced by a screen showing information about user app 160, shown in FIG. 24. Available here is various information, for example, the serial number, the version number of wearable drug delivery device 102, information about the last communication to the wearable drug delivery device 102 or to the cloud 111, etc.

In some embodiments, user app 160 is provided with a facility allowing the user to send log files to a customer care center for analysis. By selecting button 2402 ("Send Files To Customer Care"), the user has the ability to send log files to the customer service center. These may be useful, for example, in diagnosing problems encountered by the user during operation of the device. The warning icon ("!") indicates that the log files are in the process of being sent, but the sending process has not yet completed.

Figure 24B:
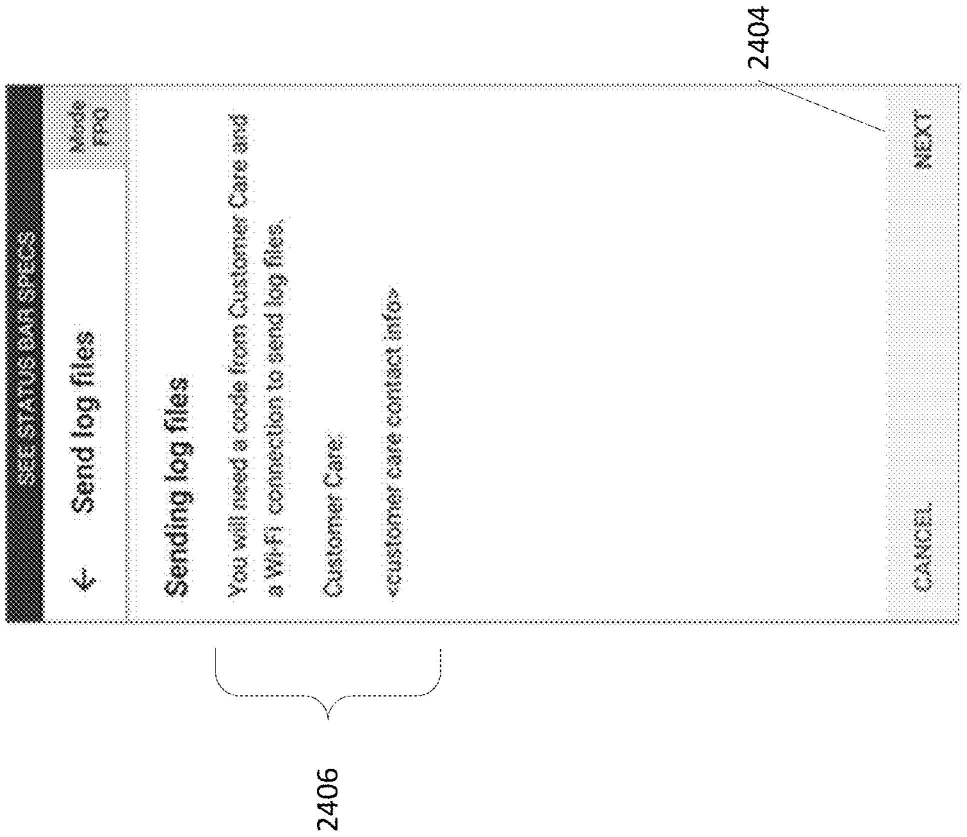
FIGS. 24(*b-c*) show screens used to send log files to a customer care center.
Figure 24C:
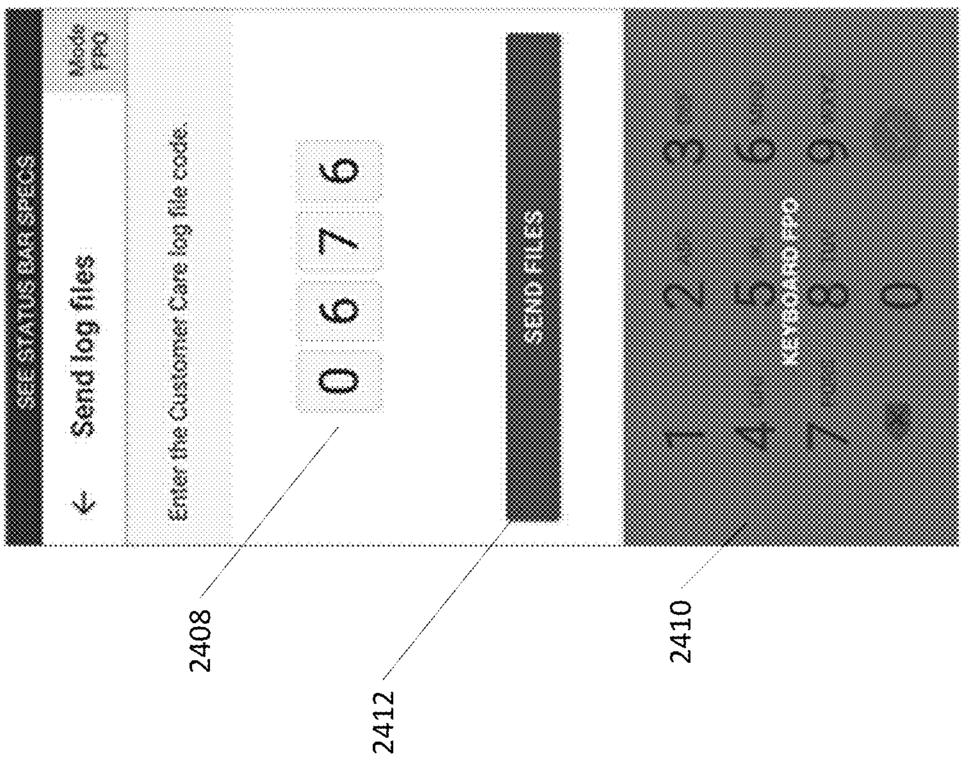

When button 2402 is selected, the screen shown in FIG. 24*b* is displayed. In some embodiments, the user must have a personal identification number (PIN) to send the log files.

As such, the screen shown in FIG. 24*b* may also include instructions for obtaining the PIN 2406. The user may receive the PIN, for example, via a communication through user app 160 or a communication independent of user app 160. If the user already has a PIN, the user may select button 2404 ("Next") which will cause the screen in FIG. 24*c* to be displayed. The user then enters the PIN in field 2408 using keypad 2410 and, when completed, selects button 2412 ("Send Files") to initiate the sending of the log files to the customer care center. Upon selection of button 2412, the screen shown in FIG. 24*c* will be removed and control will return to the previously displayed screen.

Figure 25A:
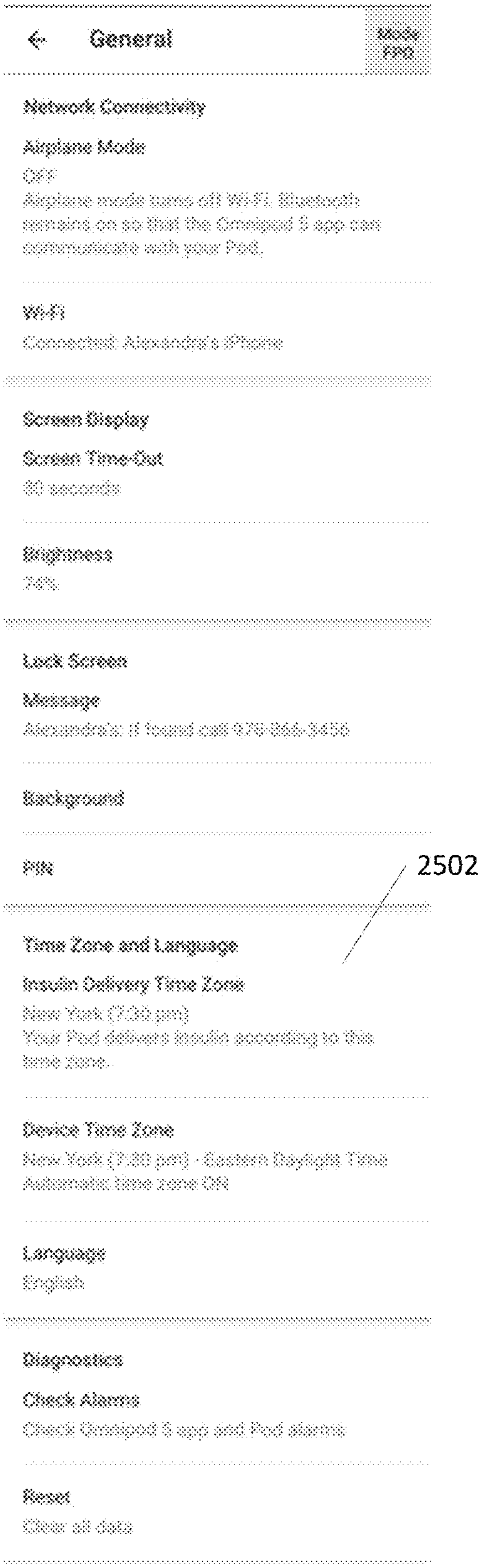
FIG. 25(*a*) shows a menu for providing general set up of the application.

A user selection of button 1322 ("PDM Settings") from main menu 1300 will cause the main menu 1300 to be replaced by the menu shown in FIG. 25*a*, which allows the user to set various aspects of the operation and appearance of the user device 105 on which user app 160 is executing. For example, the user may switch airplane mode on or off, change the Wi-Fi settings, the screen timeout, the screen brightness, the lock screen message, the background image and the security pin, etc.

Figure 25C:
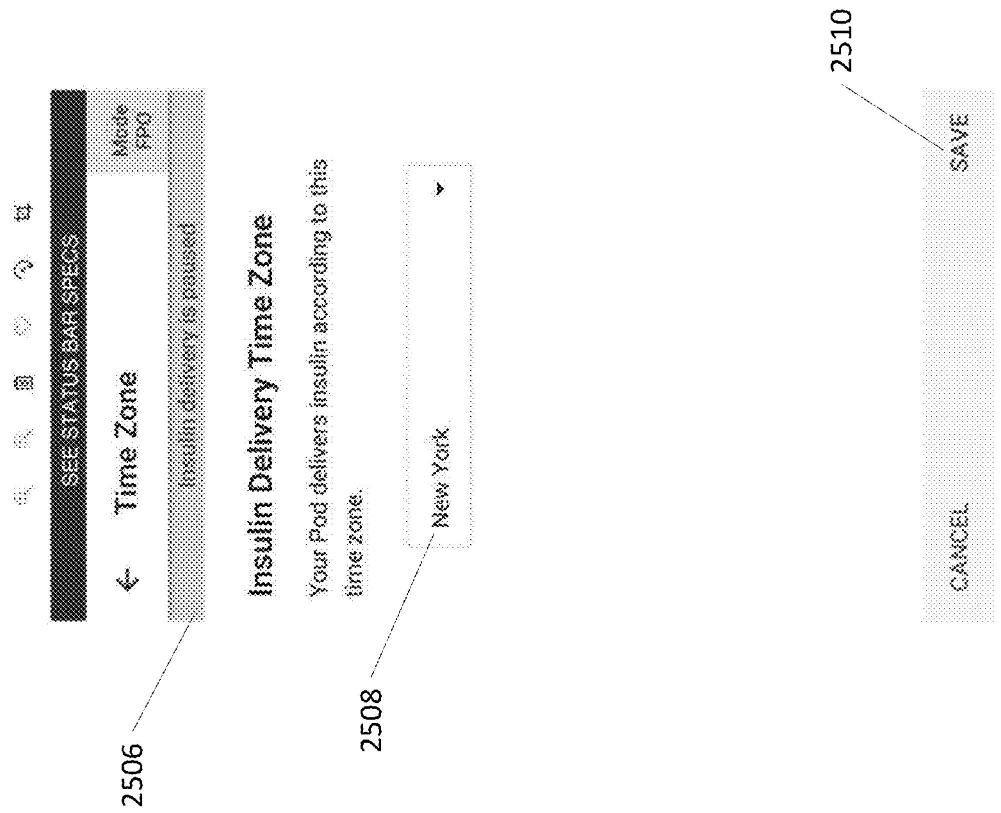
Figure 25B:
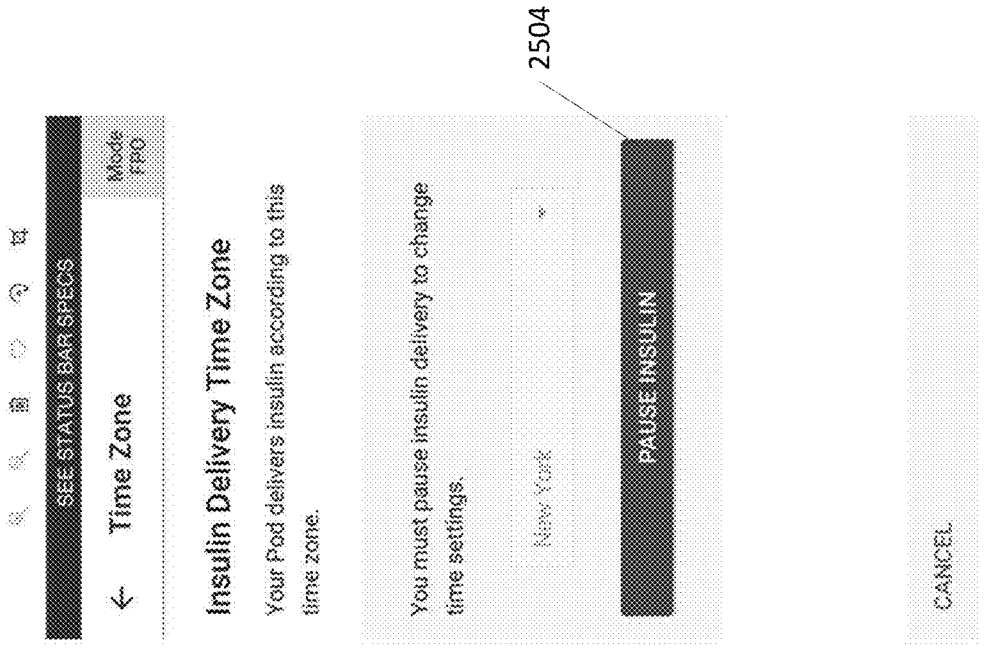

In addition, the user may also set a default time zone and language and a time zone from which the times for the insulin delivery are calculated by selecting button 2502 in FIG. 25*a*. This causes the screen shown in FIG. 25*b* to appear, which first warns the user that the insulin delivery must be paused before the time zone can be changed. When the user pauses insulin delivery by pressing button 2504 ("Pause Insulin"), the screen changes as shown in FIG. 25*c*, showing banner 2506 indicating that insulin delivery is paused, and enabling selection menu 2508, which the user may use to select the time zone. Once the time zone is selected, the user may select button 2510 ("Save"), which will save the selection of the time zone, dismiss the screen shown in FIG. 25*c* and restart insulin delivery if paused. When the user has allowed access to the device's location information during set-up, the time zone may automatically change as the user moves between time zones, and the user may be notified that the time zone has been updated, or the user may be asked to confirm whether to update the time zone in which the user is now located. Periodically, the system may confirm that the time zone in which the user is currently located is the same as the time zone currently being used by the system for drug delivery. If there is a mismatch in time zones, the user may be alerted and queried whether the time zone should be updated. If the time zone is updated, corresponding changes to insulin delivery will result. For example, the basal profiles, which may deliver different amounts or rates of insulin at different times of day, may now correspond to the updated time zone. In addition, rather than the user having to set a time zone (default or otherwise), the user device 105 may automatically detect and/or provide the time and time zone to the user app 160 and/or the wearable drug delivery device 102, such that the user does not need to enter the time or time zone. Moreover, if the time and/or time zone of user device 105 updates automatically (for example, in a smartphone), then the time and/or time zone used by user app 160 and wearable drug deliver device 102 may also be updated automatically. User app 160 may periodically query user device 105 to determine whether the time and/or time zone has been changed by the user or updated automatically by user device 105, for example, upon traveling to a new location.

In addition, the user may select the language, run diagnostics or reset user app 160. The selection of any menu item on the "PDM Settings" menu may result in other screens being displayed to set the specific settings. Some options may or may not be available, depending upon the current mode in which user app 160 is executing.

Pause Insulin Screens

Figure 26A:
FIGS. 26(*a-b*) show examples screens allowing the user to pause and start delivery of the medication.
Figure 26B:
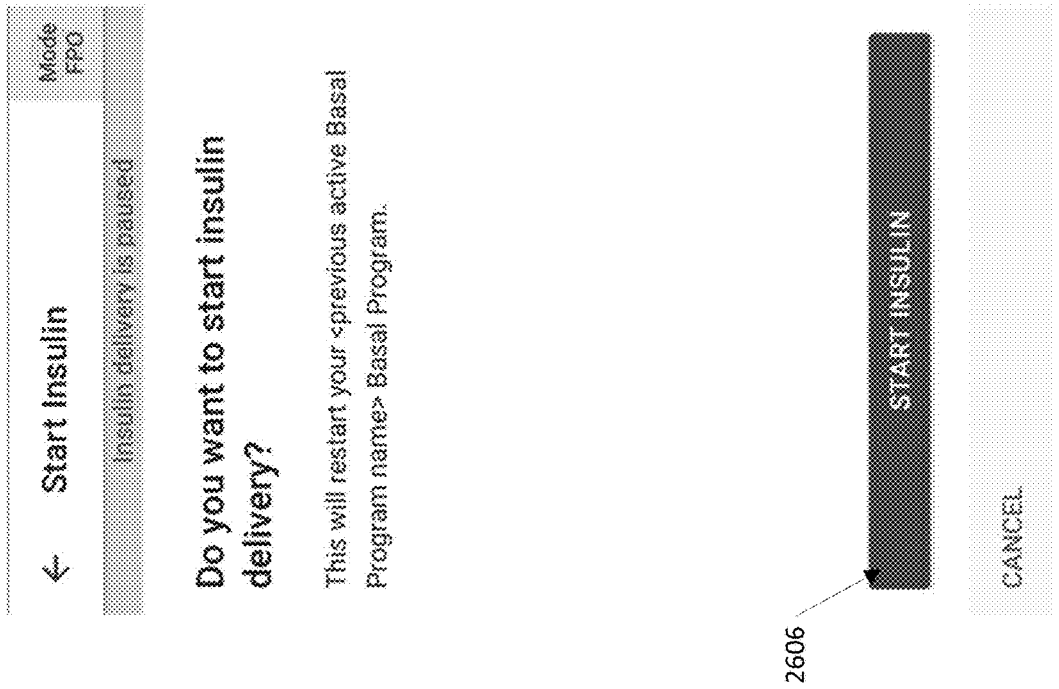

A user selection of button 1310 ("Pause Insulin") from main menu 1300, shown in FIGS. 13(*a-b*), allows the user to suspend delivery of insulin for a specified time. Note that button 1310 may only be available if certain conditions are met. For example, button 1310 may be disabled if there is a temp basal profile or an extended bolus program running. Upon selection of button 1310, the screen shown in FIG. 26*a* may be displayed, where the user is able to specify the length of the pause in the delivery of insulin. In some embodiments, upon selection of field 2602, the user may be presented with a modal keypad which allows a manual entry of the time. In other embodiments, upon selection of field 2602, the user may be provided with a menu from which a time period menu item may be selected. Upon dismissal of the modal screen, the specified time for pause is transferred to field 2602. The user may start the pause by pressing button 2604. Once the delivery of insulin has been paused, button 1310 in main menu 1300 may change from "Pause Insulin" to "Start Insulin" which, when selected, will allow the user to restart the delivery of insulin. A user selection button 1310 ("Start Insulin") will cause the screen in FIG. 26*b* to appear, which allows the user to resume the delivery of insulin with the last active basal program. A user selection of button 2606 will cause the restart. Once the delivery of insulin has been resumed, button 1310 in menu 1300 will revert to displaying the text "Pause Insulin" and will be enabled if all other conditions are met.

HypoProtect™ Mode Screens

Figure 27A:
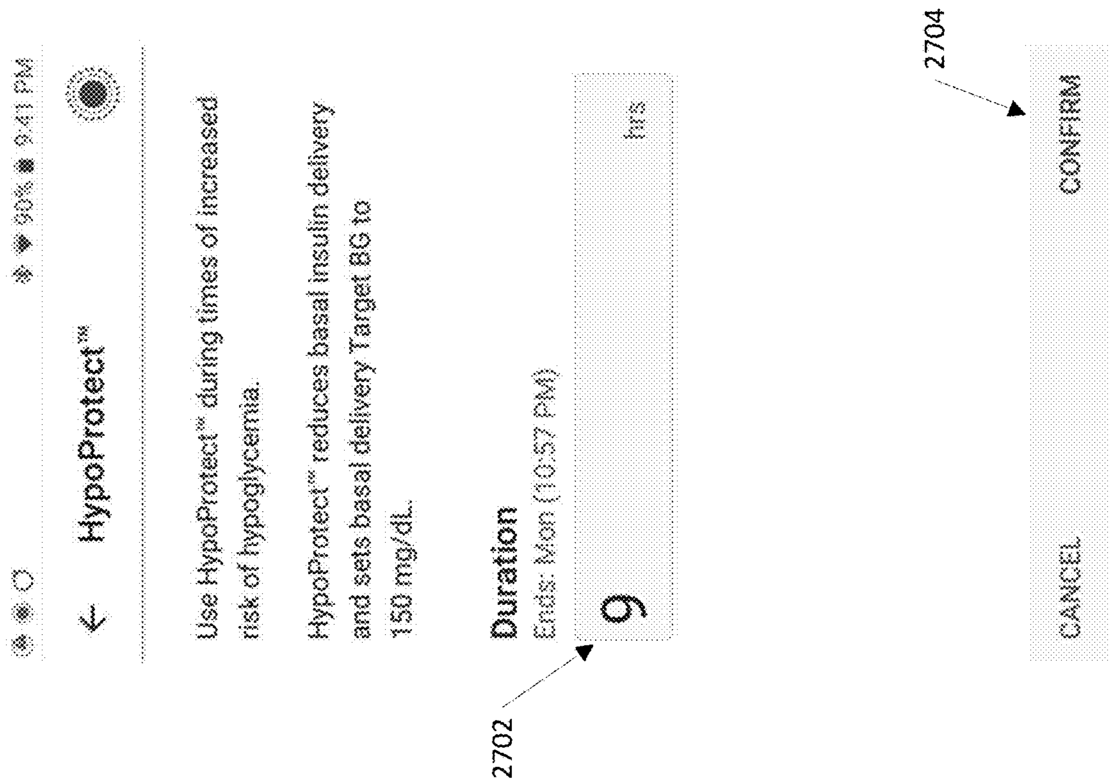
FIGS. 27(*a-b*) show examples screens allowing the user to in initiate and cancel HypoProtect™ mode.
Figure 27B:
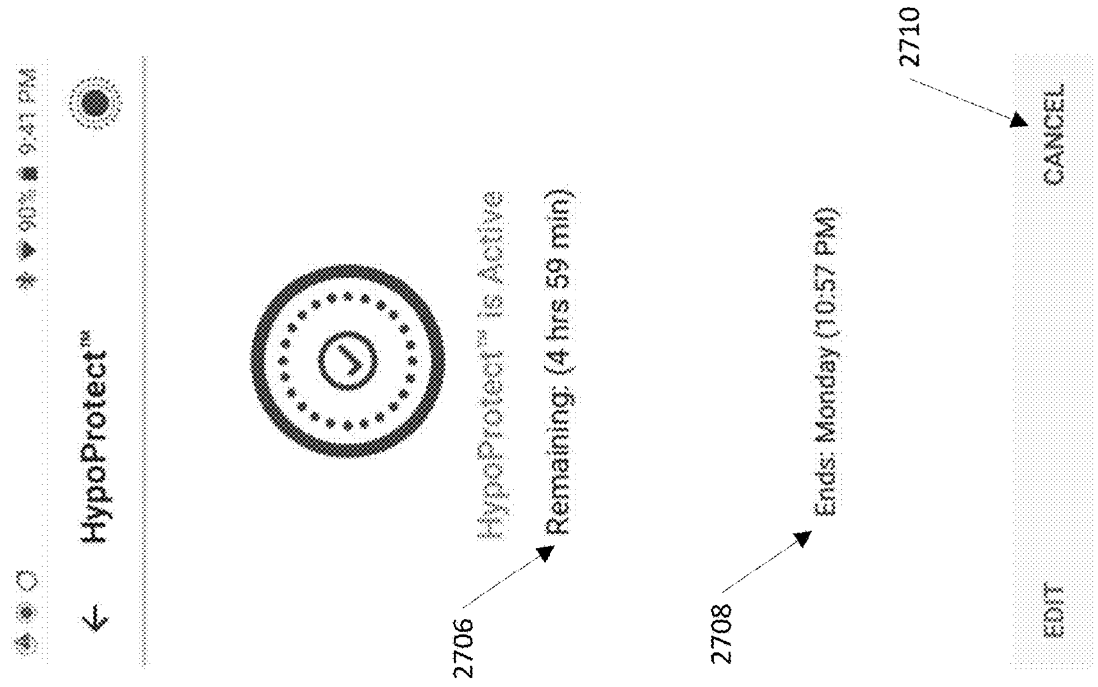

A user may initiate "HypoProtect™ Mode" by a user selection of button 1308 on main menu 1300, shown in FIGS. 13(*a-b*). HypoProtect™ mode stops, or in some embodiments, may reduce by 25-95% (such as 50% or 75%), the basal insulin delivery and sets the basal delivery target blood glucose level to a predetermined amount (e.g., in the range of 150-200 mg/dL, such as 200 mg/dL). HypoProtect™ mode is used typically during times of increased risk of hypoglycemia, such as during exercise or during sleeping hours or when first waking up in the morning. Upon selection of button 1308, the screen shown in FIG. 27*a* will appear, which allows user to set the duration of HypoProtect™ mode. Upon selection of field 2702, the user may be presented with a modal keypad which allows a manual entry of the time. In other embodiments, upon selection of field 2702, the user may be provided with a menu from which a time period menu item may be selected. Upon dismissal of the modal screen, the specified time for the duration of HypoProtect™ mode is transferred to field 2702. Upon selection of button 2704 ("Confirm"), HypoProtect™ mode is initiated, and the screen shown in FIG. 27*b* is displayed. This screen shows the remaining time 2706 that HypoProtect™ mode will run and the exact day and time when HypoProtect™ mode will end at 2708. The user may cancel HypoProtect™ mode and any time by a selection of button 2710 ("Cancel"). When in HypoProtect™ mode, informational area 404 of home screen 400 may appear as shown in FIG. 6*f*.

Switch Mode Screens

Figure 28A:
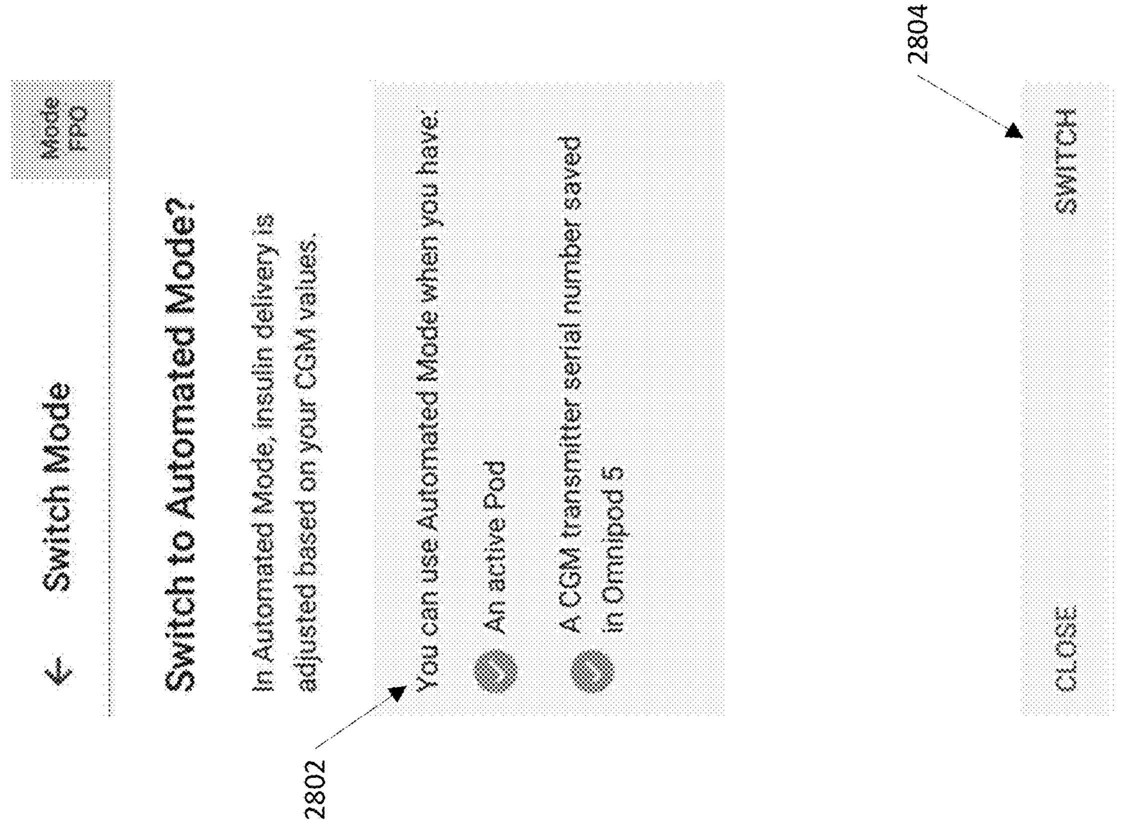
FIGS. 28(*a-b*) show examples screens allowing the user to switch operation of the user application between automated mode in manual mode.
Figure 28B:
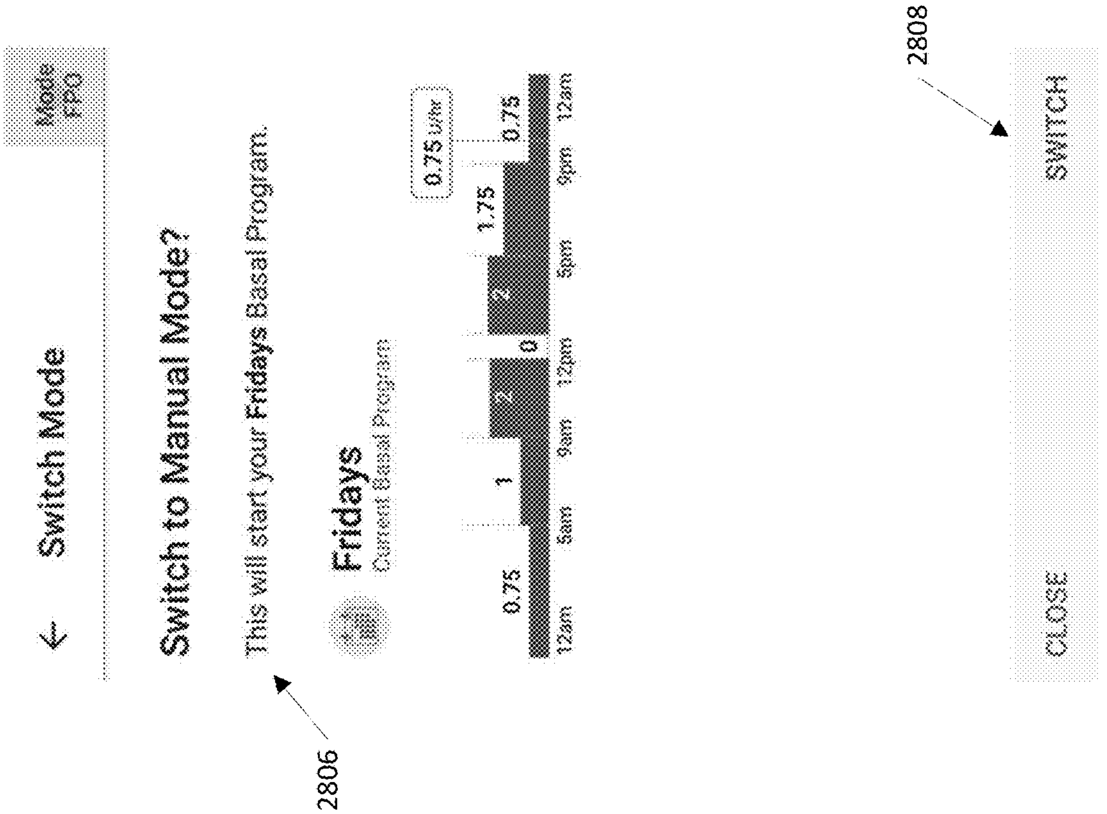

Button 1324 ("Switch Mode") on main menu 1300, as shown in FIGS. 13(*a-b*), allows the user to switch between Automated and Manual modes. If the user is currently in Manual mode, a user selection of button 1324 will cause the screen shown in FIG. 28*a* to display. Shown on the screen is an informational block 2802 showing the user when automated mode may be entered, with green checkmark showing that the indicated conditions have been met. If any condition is not been met, a red "X" may be shown next to that condition. If all conditions are met, the user may enter automated mode by a selection of button 2804 ("Switch"). If user app 160 is currently in Automated mode, a selection of button 1324 will cause the screen shown in FIG. 28*b* to appear, allowing the user to switch to Manual mode. The screen shows an informational block 2806 which informs the user of the basal program that will be executed when the switch is made. The user may confirm the switch by pressing button 2808 ("Switch").

CGM Transmitter Screens

Figure 29B:
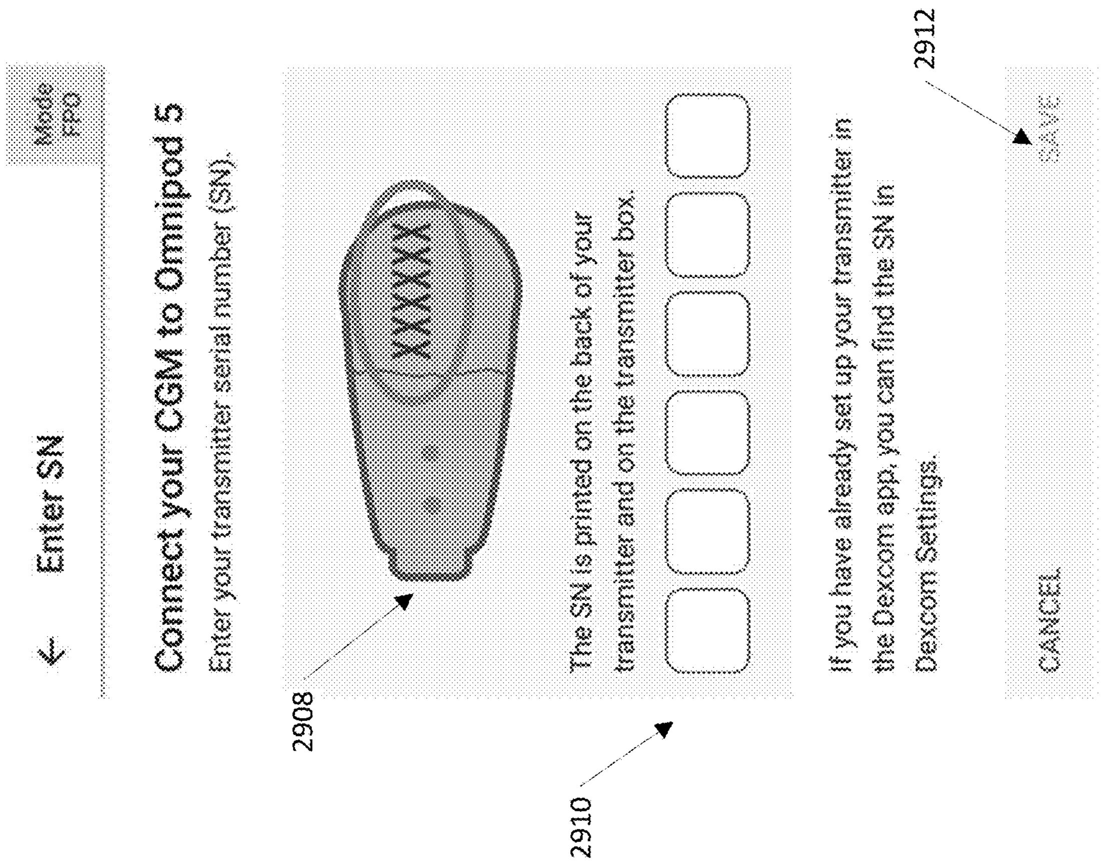
FIGS. 29(*a-b*) show examples screens allowing the user to connect a new medication delivery device with the user application.
Figure 29A:
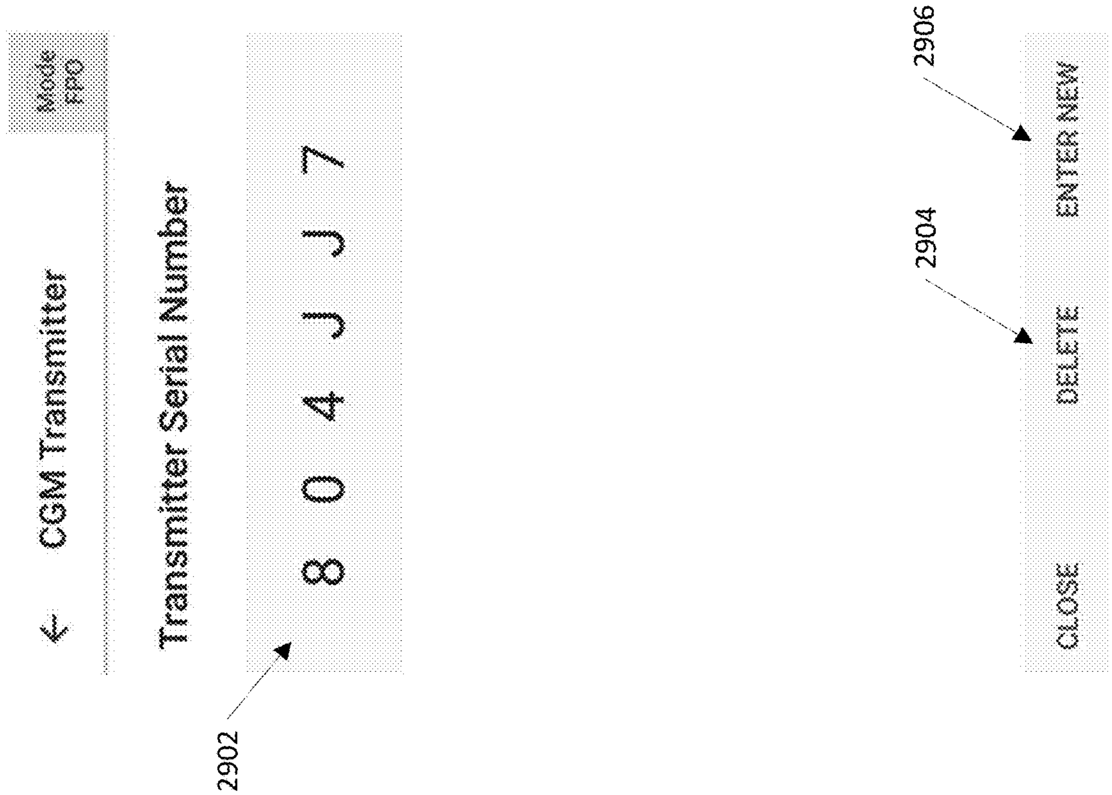

A selection of button 1326 from a menu 1300 shown in FIGS. 13(*a-b*) allows the user to view and/or change the serial number of CGM 108. The figure shown in FIG. 29*a* is initially shown upon selection of button 1326. Serial number 2902 is displayed. In certain instances, if the CGM has expired, the serial number may be displayed in red and the indicia "Expired" may also be displayed on the screen. The user may use buttons 3204 and 3206 to enter the serial number of a new CGM. Upon selection of button 2906, the screen shown in FIG. 29*b* will be displayed. This screen shows an informational block 2908 showing the user where to locate the serial number on the CGM 108. In addition, upon selection of field 2910, a modal keyboard is presented to the user, allowing the user to enter the serial number from CGM 108. When the user is finished entering the serial number, the user may save the serial number by a user selection of button 2912 ("Save"), which will cause a reversion to the screen shown in FIG. 29*a* and the new serial number to be transferred to field 2902.

Reminders Screens

Figure 30B:
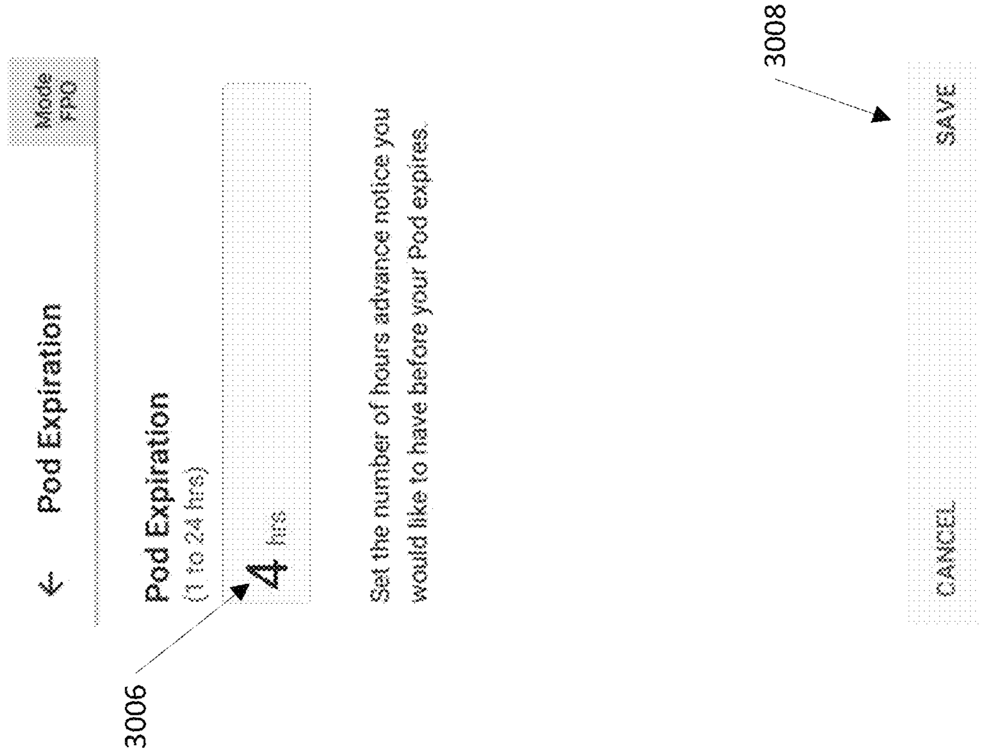
FIGS. 30(*a-b*) show examples screens allowing the user to set the parameters of reminders provided by the user application.
Figure 30A:
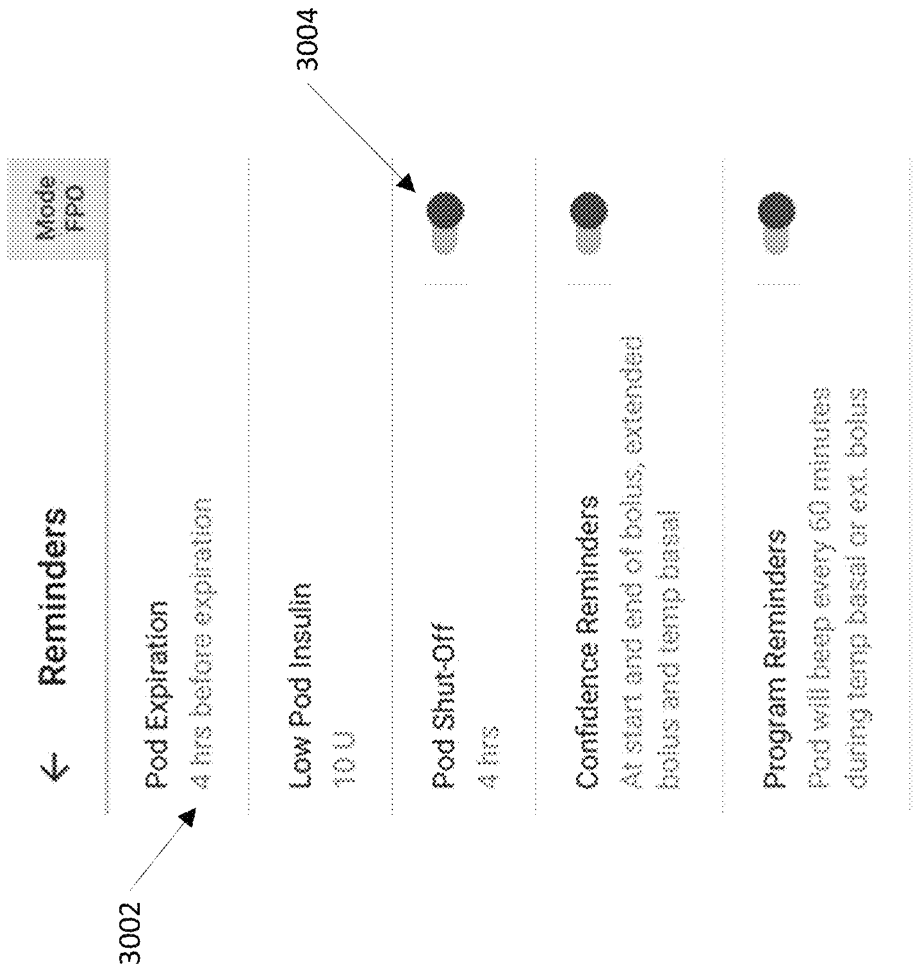

The user may enable/disable and/or set the parameters for when reminders are provided by user app 160. A selection of button 1328 ("Reminders") in the "Settings" submenu in main menu 1300, shown in FIGS. 13(*a-b*), displays the screen shown in FIG. 30*a*. The screen shows a list of the reminders. The current settings 3002 for each reminder is shown under the name of the reminder. For example, in the exemplary screen showed in FIG. 30*a*, the user has set the "Pod Expiration" reminder to four hours before expiration of drug delivery device 102, which indicates that the user will be provided with a reminder from user app 160 four hours prior to the expiration of the drug delivery device 102. Certain reminders may be enabled or disabled by user selection of slider 3004. A tap on slider 3004 will cause the state to switch between "on" and "off". The exemplary screen shows the three reminders being enabled. FIG. 30*b* shows an example of a screen that may be used to set the parameters of one of the reminders. In the exemplary screen, the "Pod Expiration" reminder is being set. In certain embodiments, a user selection of field 3006 will cause a modal numerical keyboard to appear, allowing the user to type in the number of hours before expiration that the reminder will be displayed. In other embodiments, a modal menu may appear having menu items for various numbers of hours. Upon dismissal of the modal menu, the specified number of hours will be transferred to field 3006. The user may save the setting by user selection of button 3008.

Viewers Screens

User app 160 may be provided with a feature that allows designated people to view the data generated by user app 160. To view a list of the viewers having permission to view the user data, the user may select button 1330 ("Viewers") from main menu 1300 shown in FIGS. 13(*a-b*). When button 1330 is selected, the screen shown in FIG. 31*a* is displayed, showing a list of viewers 3102. The list of viewers having permission to view the user's data may be kept on a cloud-based service 111 and may be downloaded to user device 105 upon selection of button 1330. Each viewer in list 3102 is accompanied by a modal options menu 3105 which, when selected, displays various menu items. For example, the menu may contain options to edit or delete the viewer. If the user wishes to edit a viewer, the "Edit" menu selection may be selected from modal menu 3105 and the screen shown in FIG. 31*e* will be displayed, allowing editing of the viewer's information, as explained below.

Figure 31B:
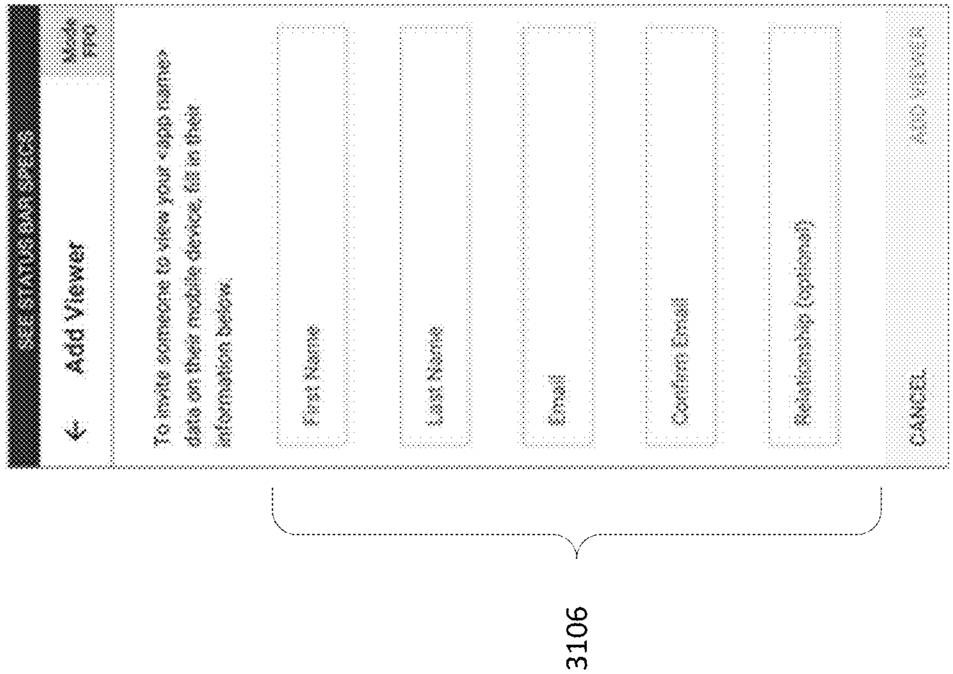
FIGS. 31(*a-f*) show examples of screens displaying a list of people ("viewers") authorized to view data generated by user app 160 and allowing the user to add new viewers to the list.
Figure 31A:
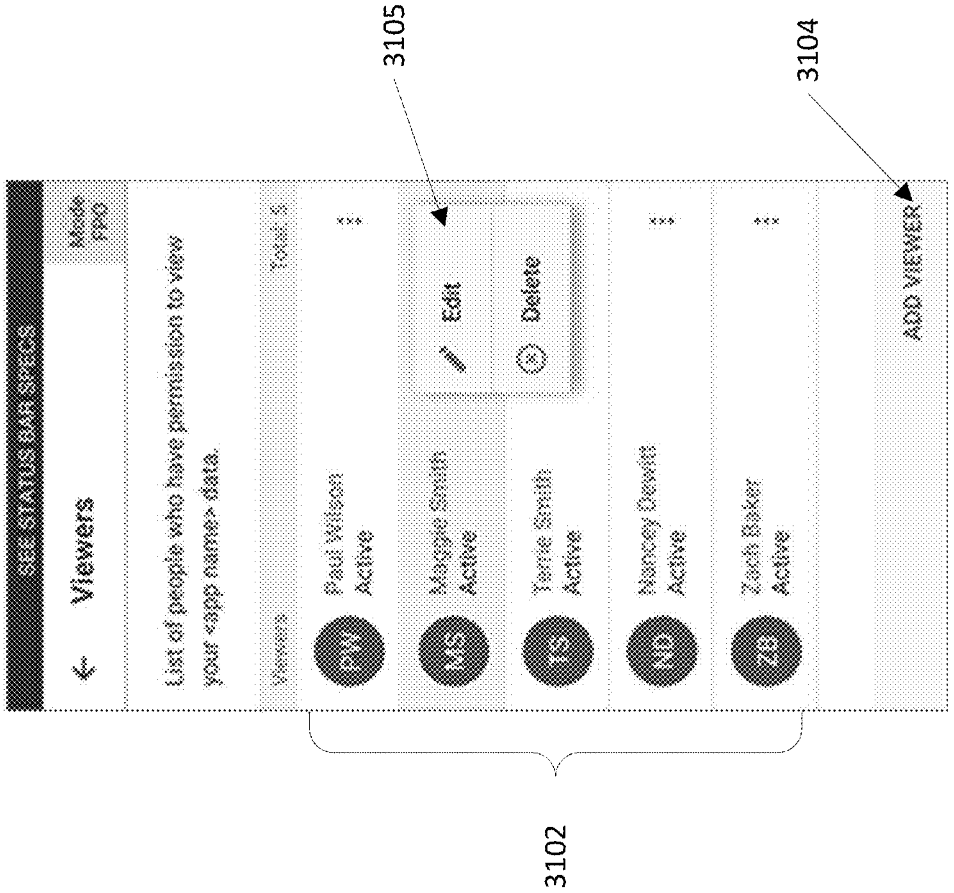

A new viewer may be added by pressing button 3104 ("New Viewer"), which will cause the screen in FIG. 31*b* to be displayed. This screen provides fields 3104 into which the user can input various required or optional information about the new viewer, for example, first name, last name, email address and relationship to the user. In various embodiments, other fields may also be required or desired to identify the new viewer.

Figures 31C, 31D:
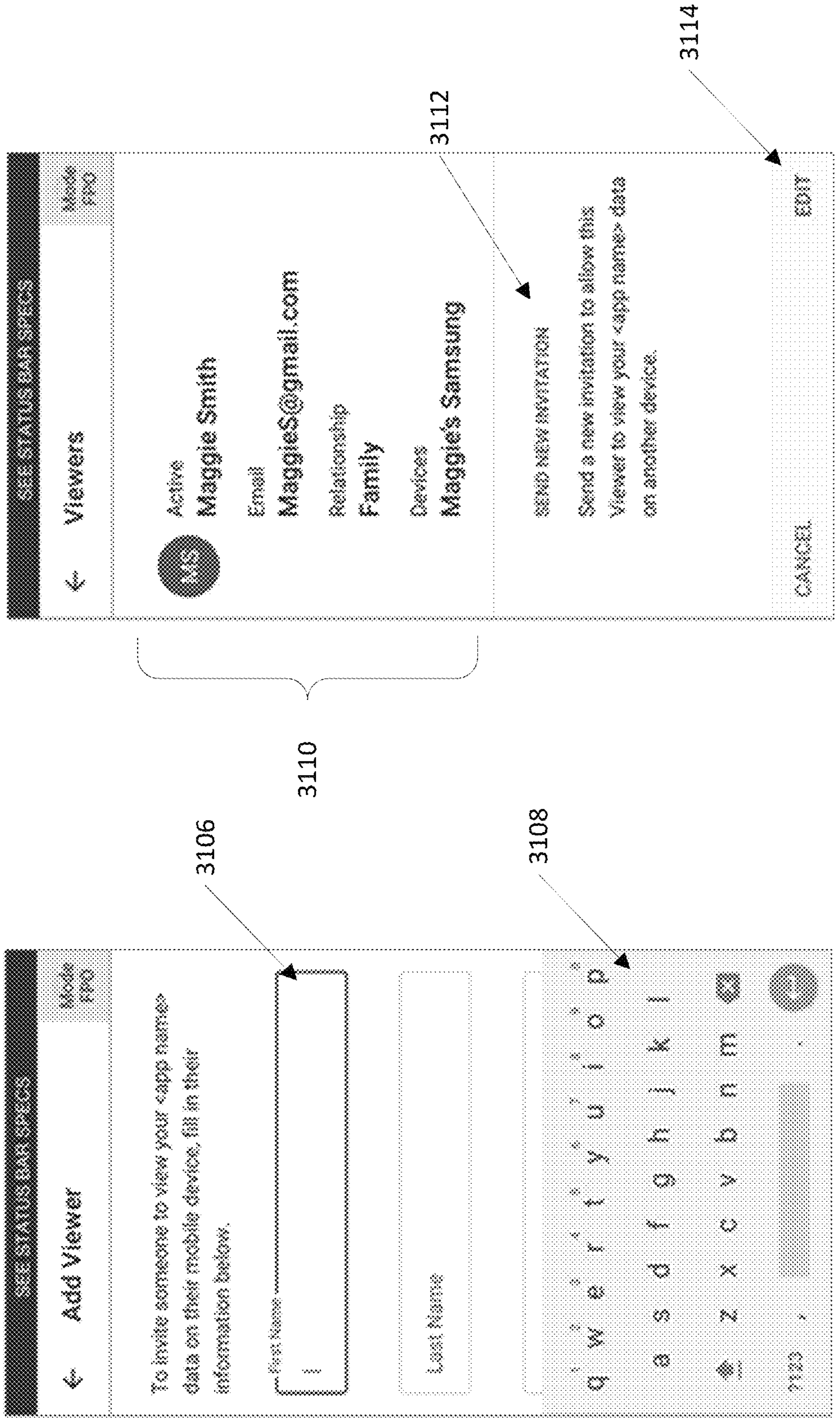
Figure 31F:
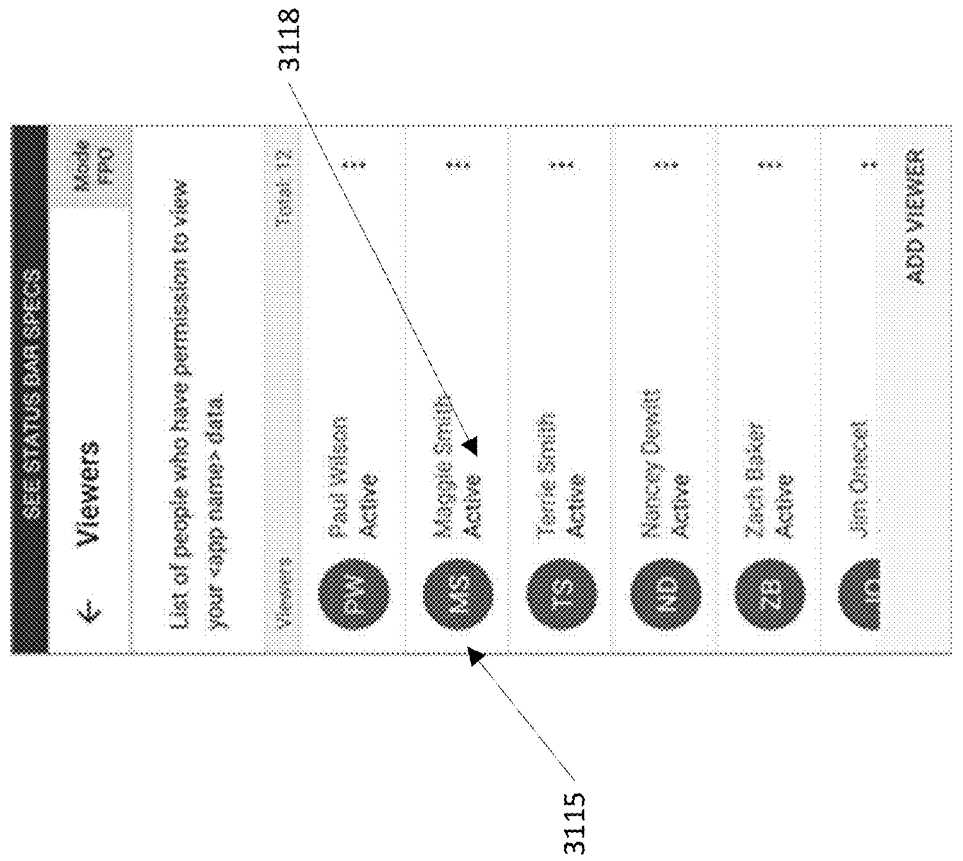
Figure 31E:
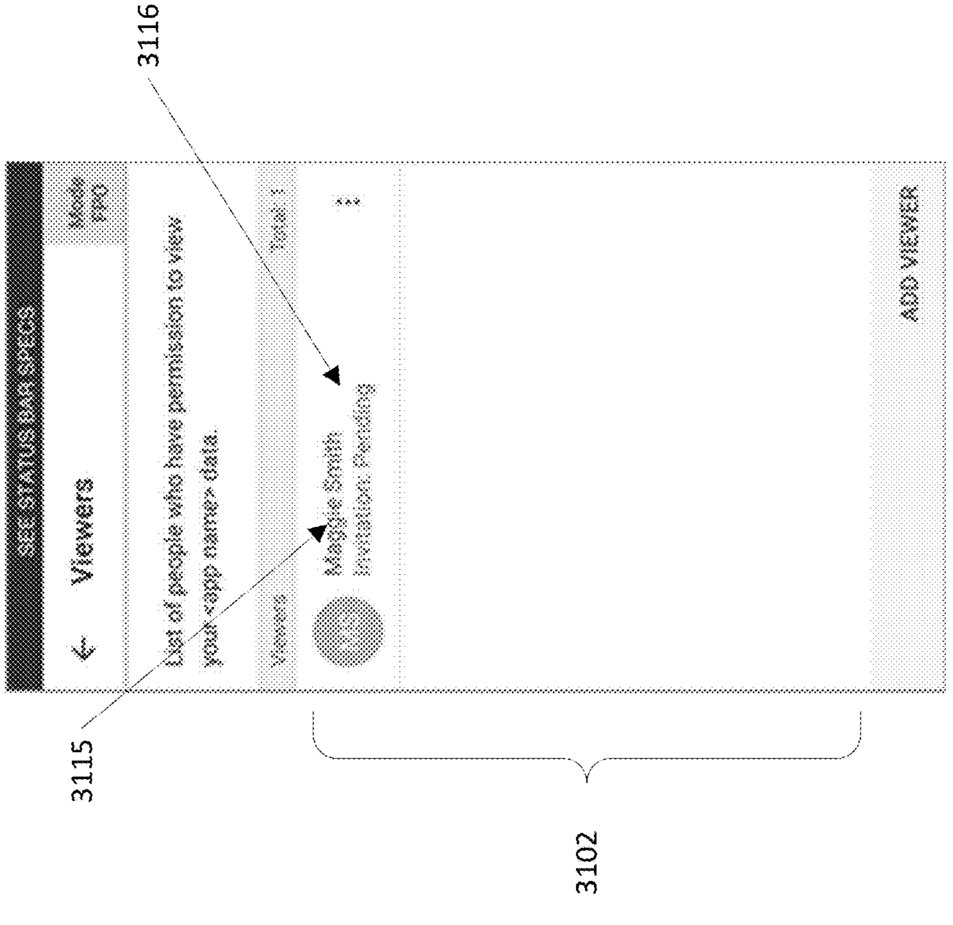

Upon selection of one of fields 3106, a modal keyboard 3108 will be displayed over the screen as shown in FIG. 31*c* to allow the user to enter the required information about the new viewer. Once all of the required fields are filled, the screen shown in FIG. 31*d* is displayed showing a summary of the new viewer's information. To correct any errors in the new viewer's information, the user may select button 3114 ("Edit"), which will return the user to the screen shown in FIG. 31*b*. Note that the screen shown in FIG. 31*d* may also be reached by selecting the "Edit" button from the modal menu 3105 beside a viewer from list 3102 shown in FIG. 31*a*. This allows the user to edit the information of already-existing viewers, for example, to change the viewer's email address. An invitation to view the user's data is sent to the new viewer upon selection of button 3112 ("Send New Invitation"). Once the invitation has been sent, the screen shown in FIG. 31*e* will be displayed. This screen is the same screen as shown in FIG. 31*a*, however, the new user 3115 has been added to the list and is shown as being "Pending" as indicated by status indicator 3116. Upon acceptance of the invitation by the new viewer, the screen shown in FIG. 31*f* will be displayed showing the new user 3115 having an "Active" status as indicated by status indicator 3118. Note that this is the same screen as shown in FIG. 31*a*, with new user 3115 added.

As would be realized by one of skill in the art, the user interface is comprised of many screens, providing a wide range of functionality, the majority of which are not shown herein. An exemplary selection of the screens comprising the user interface have been presented herein to show the various features of user app 160. The invention is not meant to be limited by the exact depiction of each individual screen, including, for example, the specific text displayed on each screen, the placement of features on each screen, the colors in which various features on the screens are displayed, and the flow from one screen to the next. As would be realized, any of these aspects of the user interface may vary while still providing the same functionality. Instead, the intended scope of the invention is captured in the claims which follow.

The invention claimed is:

1. A medication delivery system comprising:
   - a drug delivery device;
   - a user device in wireless communication with the drug delivery device; and
   - a user application having a graphical user interface, executing on the user device, the user application controlling delivery of a medication by the drug delivery device;
   - wherein the graphical user interface of the user application includes:
     - a default screen displayed on startup of the user application, the default screen comprising:
     - an informational area displaying a most-recent blood glucose level of a user,
     - a trend indicator, showing a trend of the blood glucose level of the user indicated by a plurality of previous blood glucose readings and an indicator of the estimated insulin on board;
     - a bolus display area comprising an indicator of a most recent bolus delivered by the drug delivery device;
     - a CGM area that, when selected, displays a graph of blood glucose readings within a user-selectable time period; and
     - a mode indicator, indicating whether the user application is operating in a manual mode in which the drug delivery device delivers the medication using pre-programmed dosing parameters or an automated mode in which the drug delivery device adapts the dosing parameters over time; and
   - a viewers screen allowing the viewing of a list of people authorized to view data generated by the user application controlling the delivery of the medication and allowing the adding of new authorized people, wherein each person on the list of the viewers screen is associated with a status indicator indicating whether the person is an active viewer or pending approval; and
   - wherein a request to add a view is sent via the user application, and the status indicator is updated based on information received at the user device.

2. The system of claim 1 wherein the startup screen further comprises:
   - a tab bar comprising a dashboard tab, an insulin tab and a pod info tab;
   - wherein, when insulin tab is selected, the informational area displays a graphical representation of a basal program currently being run by the user application and the CGM area displays the most-recent blood glucose level of the user; and
   - wherein, when the pod info tab is selected, the informational area displays status information about the drug delivery device including a number of units of medication remaining in the drug delivery device and the CGM area displays the most-recent blood glucose level of the user.

3. The system of claim 1 wherein, when the bolus display area of the default screen is selected by the user, the graphical user interface displays an indication of an estimate of the insulin on board in the bolus display area.

4. The system of claim 1 wherein the startup screen further comprises a bolus button that, when selected by the user, initiates the delivery of a bolus dose of the medication.

5. The system of claim 4 wherein selection of the bolus button causes the graphical user interface to display a bolus calculator screen for calculating a total bolus dose of the medication to be delivered based on a quantity of carbohydrates ingested by the user, the most-recent blood glucose reading of the user and the estimate of the insulin on board.

6. The system of claim 4 wherein the user may initiate delivery of the bolus dose as an immediate bolus dose or as an extended bolus dose.

7. The system of claim 6 wherein the graphical user interface includes a screen allowing the user to specify parameters of the extended bolus delivery of the medication.

8. The system of claim 6 wherein, when a bolus dose or extended bolus dose is being delivered, the graphical user interface displays status of the bolus or extended bolus dose in the informational area of the default screen.

9. The system of claim 2 wherein, when insulin tab is selected, the graphical user interface displays a list of basal programs.

10. The system of claim 9 wherein the basal programs define timing and quantity of delivery of basal doses of the medication for the current day.

11. The system of claim 9 wherein the graphical user interface provides a screen allowing the user to create a new basal program.

12. The system of claim 11 wherein the screen allowing the user to create a new basal program comprises a graphical representation indicating one or more ranges of hours and a basal rate for delivery of the medication during each range of hours.

13. The system of claim 9 wherein the list of basal programs includes one or more temporary basal programs specifying timing and quantity of delivery of basal doses for a portion of the current day, the temporary basal programs increasing or decreasing the quantity of the medication specified by a currently executing basal program.

14. The system of claim 1 wherein the graphical user interface further comprises a menu button that, when selected, displays a menu comprising a plurality of menu items overlayed on the currently displayed screen of the graphical user interface.

15. The system of claim 14 wherein one of the menu items, when selected, initiates a HypoProtect mode that suspends delivery of the medication for a user-specified duration.

16. The system of claim 15 wherein, when HypoProtect mode is enabled, the graphical user interface displays a HypoProtect mode indicia in the informational area of the default screen.

17. The system of claim 1 wherein the graphical user interface includes screens providing instructions for replacing the drug delivery device.

18. The system of claim 1 wherein the graphical user interface includes screens providing an interface to a food library containing at least a quantity of carbohydrates contained in individual foods in the food library.

19. The system of claim 1 wherein access to the user application requires entry of a user PIN and further wherein the graphical user interface includes screens allowing the user to set and enter the PIN.

20. The system of claim 14 wherein one of the menu items, when selected, causes the graphical user interface to display a history of the delivery of the medication and a timeline of events.

21. The system of claim 14 wherein one of the menu items, when selected, causes the graphical user interface to display screens allowing the user to switch between the automated mode and the manual mode.

22. The system of claim 1 further comprising:

a continuous glucose monitor in wireless communication with the user device, the continuous glucose monitor providing periodic blood glucose readings from the user.

23. The system of claim 1, the user application generating one or more log files, wherein the graphical user interface includes a screen allowing the sending of the one or more log files to a customer care facility.

* * * * *